US 9,884,164 B2
(12) United States Patent
Tass

(10) Patent No.: US 9,884,164 B2
(45) Date of Patent: *Feb. 6, 2018

(54) APPARATUS AND METHOD FOR THE CONDITIONED DESYNCHRONIZED NON-INVASIVE STIMULATION

(75) Inventor: Peter Alexander Tass, Munich (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 990 days.

This patent is subject to a terminal disclaimer.

(21) Appl. No.: 13/640,826

(22) PCT Filed: Feb. 16, 2011

(86) PCT No.: PCT/DE2011/075025
§ 371 (c)(1),
(2), (4) Date: Dec. 19, 2012

(87) PCT Pub. No.: WO2011/127918
PCT Pub. Date: Oct. 20, 2011

(65) Prior Publication Data
US 2013/0090519 A1    Apr. 11, 2013

(30) Foreign Application Priority Data

Apr. 12, 2010  (DE) ................. 10 2010 016 404

(51) Int. Cl.
*A61M 21/00*  (2006.01)
*A61M 21/02*  (2006.01)
(Continued)

(52) U.S. Cl.
CPC ........... *A61M 21/02* (2013.01); *A61B 5/4082* (2013.01); *A61H 23/00* (2013.01); *A61M 21/00* (2013.01);
(Continued)

(58) Field of Classification Search
CPC ............. A61N 1/36014; A61N 5/0622; A61M 2230/10; A61H 2230/10
(Continued)

(56) References Cited

U.S. PATENT DOCUMENTS 3,780,724 A * 12/1973 John ........................... 600/544
2005/0143617 A1 * 6/2005 Auphan ....................... 600/26
(Continued)

FOREIGN PATENT DOCUMENTS

CN          1774279 A      5/2006
DE     102005014383 A1    9/2006
(Continued)

OTHER PUBLICATIONS

Benninghoff, et al., Der funktionelle Bau der Teile, Lehrbuch der Anatomi des Menschen Dargestellt unter Bevorzugung funktioneller Zusammenhänge, 3. Bd. Nervensystem, Haut und Sinnesorgane, [Textbook of Human Anatomy, Presented With Emphasis on Functional Relationships, 3rd. vol., Nervous Sustem, Skin and Sensory Organs] pp. 126-137, Urban and Schwarzenberg, Munich 1964. (w/concise explanation).
(Continued)

*Primary Examiner* — Charles A Marmor, II
*Assistant Examiner* — Shannon McBride
(74) *Attorney, Agent, or Firm* — Arent Fox LLP

(57) ABSTRACT

A device with a non-invasive first stimulation unit configured to generate first stimuli which, when administered to a patient, suppress a pathologically synchronous activity of neurons in at least one of the brain and the spinal cord of the patient, with a non-invasive second stimulation unit configured to generate at least one of optical, acoustic, tactile, vibratory, and thermal second stimuli, and with a control unit configured to control the first and second stimulation units, wherein the generation of the first and second stimuli takes
(Continued)

place optionally in a first or a second operating mode, and the control unit is configured to control the first and second stimulation units in such a way that, in the first operating mode, the generation of at least 60% of the second stimuli is coupled in time to the generation of the first stimuli and, in the second operating mode, the generation of at least 60% of the second stimuli takes place without the generation of the first stimuli.

17 Claims, 35 Drawing Sheets

(51) Int. Cl.
| | |
|---|---|
| *A61H 23/00* | (2006.01) |
| *A61N 1/36* | (2006.01) |
| *A61B 5/00* | (2006.01) |
| A61B 5/0484 | (2006.01) |
| A61N 5/06 | (2006.01) |
| A61B 5/04 | (2006.01) |
| A61B 5/0482 | (2006.01) |
| A61H 5/00 | (2006.01) |
| A61H 23/02 | (2006.01) |

(52) U.S. Cl.
CPC ...... *A61N 1/36025* (2013.01); *A61B 5/04001* (2013.01); *A61B 5/0482* (2013.01); *A61B 5/0484* (2013.01); *A61H 5/00* (2013.01); *A61H 23/0236* (2013.01); *A61H 2023/0227* (2013.01); *A61H 2201/0157* (2013.01); *A61H 2201/0207* (2013.01); *A61H 2201/0214* (2013.01); *A61H 2201/10* (2013.01); *A61H 2201/1604* (2013.01); *A61H 2201/5084* (2013.01); *A61H 2201/5097* (2013.01); *A61H 2230/10* (2013.01); *A61H 2230/60* (2013.01); *A61M 2021/0022* (2013.01); *A61M 2021/0027* (2013.01); *A61M 2021/0044* (2013.01); *A61M 2021/0066* (2013.01); *A61M 2230/10* (2013.01); *A61N 5/0618* (2013.01); *A61N 5/0622* (2013.01); *A61N 2005/0648* (2013.01)

(58) Field of Classification Search
USPC ..................................................... 600/26–28
See application file for complete search history.

(56) References Cited

U.S. PATENT DOCUMENTS

| | | | | |
|---|---|---|---|---|
| 2006/0047324 | A1* | 3/2006 | Tass ..................... | A61B 5/0482 607/45 |
| 2007/0083079 | A1* | 4/2007 | Lee et al. .......... | 600/27 |
| 2008/0319253 | A1* | 12/2008 | Ishiwata et al. ................ | 600/28 |
| 2010/0331912 | A1 | 12/2010 | Tass et al. | |
| 2011/0009921 | A1 | 1/2011 | Tass et al. | |
| 2011/0137373 | A1 | 6/2011 | Tass | |
| 2013/0041296 | A1 | 2/2013 | Tass et al. | |

FOREIGN PATENT DOCUMENTS

| | | |
|---|---|---|
| DE | 102008012669 A1 | 9/2009 |
| DE | 102008015259 A1 | 9/2009 |
| DE | 102010000390 A1 | 8/2011 |
| EP | 2103288 A2 | 9/2009 |
| WO | WO-2009/136931 A1 | 11/2009 |

OTHER PUBLICATIONS

International Search Report issued in corresponding application PCT/DE2011/075025, dated Aug. 22, 2011.
Wandell, et al., "Visual Field Maps in Human Cortex", Neuron 56, Oct. 25, 2007, pp. 366-383.
Bilecen, et al., "Tonotopic organization of the human auditory cortex as detected by BOLD-FMRI", Hearing Research 126, 1998, pp. 19-27.
Langers, et al., "Representation of lateralization and tonotopy in primary versus secondary human auditory cortex", NeuroImage 34, 2007, pp. 264-273.
Mühlnickel, et al., "Reorganization of auditory cortex in tinnitus", Proc. Natl. Acad. Sci. USA 95, 1998, pp. 10340-10343.

* cited by examiner

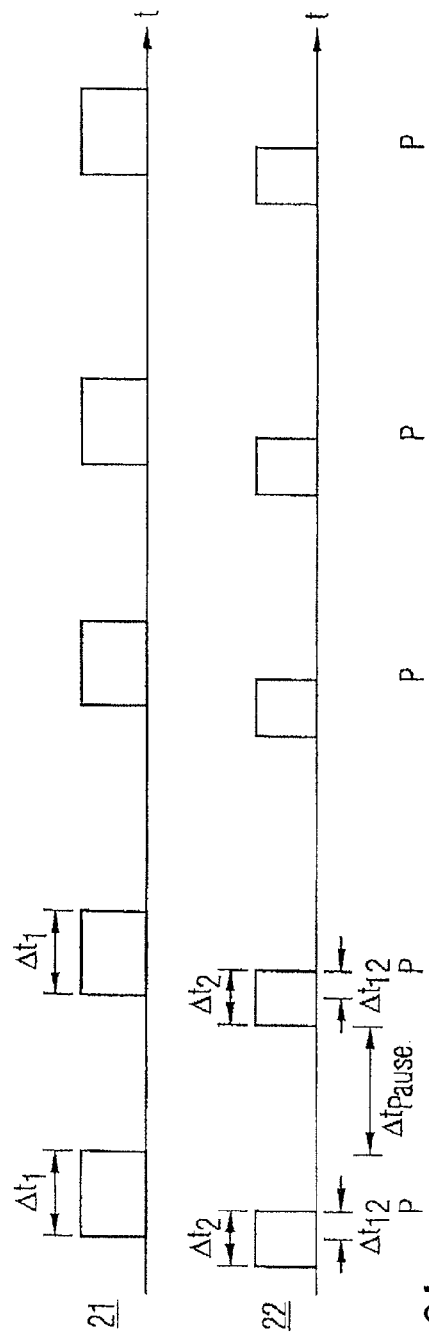
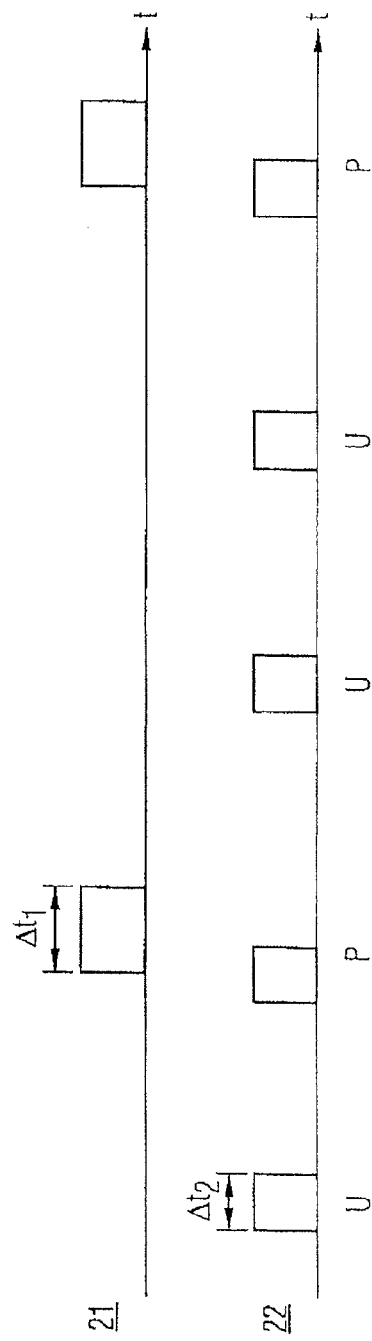
Fig. 2A
Fig. 2B

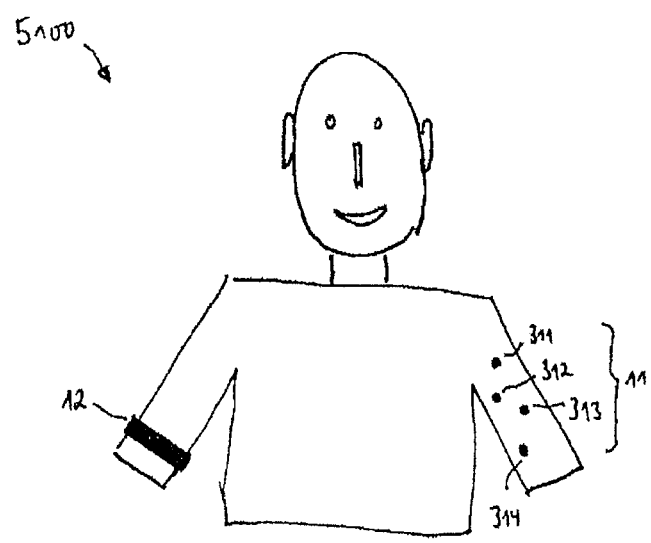

APPARATUS AND METHOD FOR THE CONDITIONED DESYNCHRONIZED NON-INVASIVE STIMULATION

TECHNICAL FIELD

The invention relates to an apparatus and to a method for the conditioned desynchronized non-invasive stimulation.

BACKGROUND

Groups of neuronal cells in localized regions of the brain, for example of the thalamus and the basal ganglia, are pathologically active, for example, excessively synchronously active in patients with neurological or psychiatric illnesses, for example, Parkinsons's disease, essential tremors, dystonia or obsessive compulsive disorders. In this case a large number of neurons form synchronous action potentials, this means that the concerned neurons trigger excessively synchronously. In contrast to this the neurons of healthy patients trigger qualitatively differently in these brain regions, for example, in an uncorrelated manner.

For Parkinsons's disease the pathologically synchronous activity changes the neuronal activity in different brain regions, for example, in areas of the cerebral cortex, such as the primary motor cortex. In this respect the pathological synchronous activity in the region of the thalamus and the basal ganglia, for example, force their rhythm onto the cerebral cortex regions, so that muscles controlled by these regions finally develop the pathological activity, for example, a rhythmic tremor.

Neurological and psychiatric diseases with excessively strongly pronounced neuronal synchronization have up until now been treated—on failure of drug therapy—by means of electrical brain stimulation.

SUMMARY

In view of this background, apparatuses and method are provided for the conditioned desynchronized non-invasive stimulation.

According to an exemplary aspect, an apparatus is provided that includes a first non-invasive stimulation unit configured to generate first stimuli during first periods of time, which, on administration to a patient, suppress a pathologically synchronous activity of neurons in at least one of the brain and the spinal cord of the patient; a second non-invasive stimulation unit configured to generate at least one of optical, acoustic, tactile, vibratory, and thermal second stimuli during second periods of time; and a measurement unit configured to record measurement signals that reproduce the pathologically synchronous activity of the neurons. Moreover, the apparatus includes a control unit configured to: control the first and second stimulation units to generate the first and second stimuli selectively in a first and a second mode of operation with the second mode of operation being subsequent to the first mode of operation, control the first and second stimulation units such that at least 60% of the second periods of time of the second stimuli overlap in time with the first periods of time of the first stimuli in the first mode of operation, and such that at least 60% of the second periods of time of the second stimuli do not overlap with the first periods of time of the first stimuli in the second mode of operation, increase a number of the first stimuli, during the second mode of operation, that overlap the generation of the second stimuli if the measurement signals exceed a predetermined first threshold value, and change from the second mode of operation to the first mode of operation if the measurement signals exceed a predetermined second threshold value being greater than the predetermined first threshold value.

BRIEF DESCRIPTION OF THE DRAWINGS

The invention will be described in detail in the following in an exemplary manner with reference to the drawing. In this is shown:

FIGS. 2A and 2B schematic illustrations of two different modes of operation of the apparatus illustrated in FIG. 1;

FIGS. 26 to 30 schematic illustrations of acoustic stimulation methods;

FIG. 51 a schematic illustration during the operation of an apparatus for the conditioned desynchronized non-invasive stimulation in accordance with a further embodiment.

DETAILED DESCRIPTION

Figure 1:
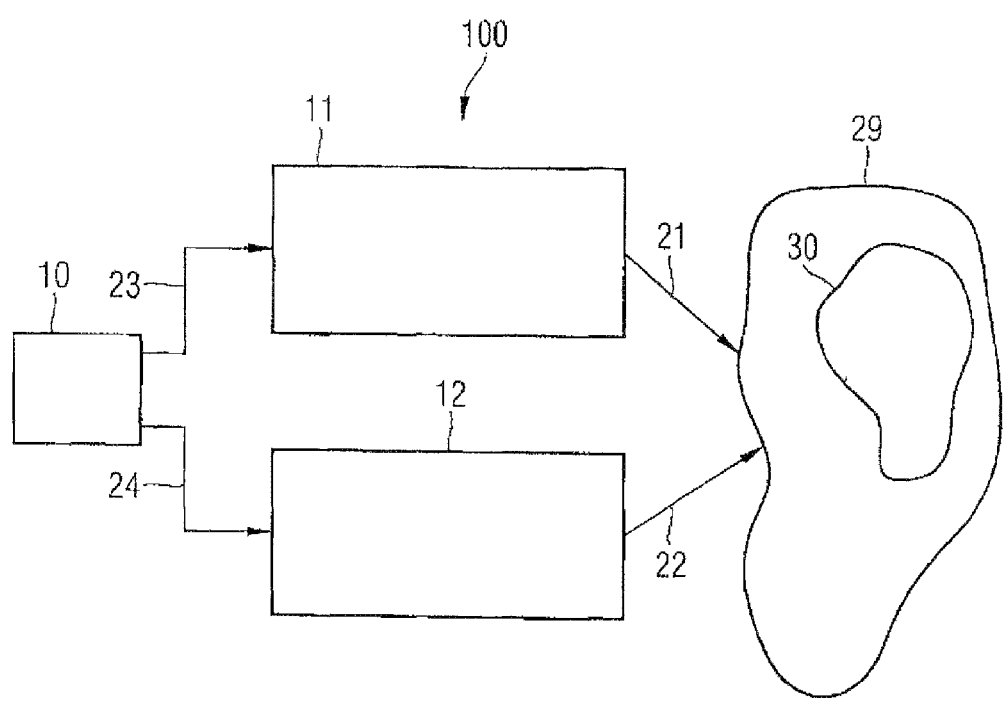
FIG. 1 a schematic illustration during the operation of an apparatus for the conditioned desynchronized non-invasive stimulation in accordance with an embodiment.

An apparatus 100 for the condition desynchronized non-invasive stimulation is schematically illustrated in FIG. 1. The apparatus 100 is composed of a control unit 10, a first stimulation unit 11 and a second stimulation unit 12. The first stimulation unit 11 generates first stimuli 21 and the second stimulation unit generates second stimuli 22. Both the first stimulation unit 11 as well as the second stimulation unit 12 are non-invasive units, this means that during the operation of the apparatus 100 they are present outside of the body of the patient and are not implanted into the body of the patient by means of operation. The first and second stimuli 21, 22 can respectively be stimuli selected from the group comprising optical stimuli, acoustic stimuli, tactile stimuli, vibratory stimuli and thermal stimuli. The first and/or second stimuli 21, 22 can intentionally be perceptible by the patient. The control unit 10 serves for the control of the two stimulation units 11 and 12 by means of control signals 23 or 24.

It can indeed be provided that the individual components of the apparatus 100, in particular the control unit 10, the first stimulation unit 11 and/or the second stimulation unit 12, are separated from one another from a construction point of view. For this reason the apparatus 100 can also be viewed as a system.

The apparatus 100 can, in particular be used for the treatment of neurological or psychiatric diseases, for example, Parkinsons's disease, essential tremors, dystonia, epilepsy, tremors as a result of Multiple Sclerosis as well as other pathological tremors, depression, movement disorders, diseases of the cerebellum, obsessive compulsive disorders, Tourette syndrome, functional disorders following a stroke, spastics, tinnitus, sleep disorders, schizophrenia, irritable colon syndrome, addictive disorders, personality disorders, attention deficit disorder, attention deficit hyperactivity syndrome, gaming addiction, neuroses, eating disorders, burn-out syndrome, fibromyalgea, migraine, cluster head ache, general head-aches, neuronalgia, ataxy, tic disorder or hypertension, and also for the treatment of other diseases.

The aforementioned diseases can be caused by a disorder of the bioelectric communication of groups of neuronal cells which are connected to one another in specific circuits. Hereby, a neuron population generates a continuous pathological neuronal activity and a pathological connectivity (network structure) possibly associated therewith. In this respect a large number of neurons form synchronous action potentials, this means that the concerned neurons trigger excessively synchronously. In addition to this the pathological neuron population has an oscillating neuronal activity, this means that the neurons trigger rhythmically. In the case of neurological or psychiatric diseases, the mean frequency of the pathological rhythmic activity of the concerned groups of neurons approximately lies in the range of 1 to 30 Hz can, however, also lie outside of this range. In contrast to this the neurons of healthy people trigger qualitatively differently, for example, in an uncorrelated manner.

In FIG. 1 the apparatus 100 is illustrated during its intended mode of operation. At least one neuron population 30 has a pathological synchronous neuronal activity as previously described in the brain 29 or the spinal cord 29 of the patient. The first stimulation 11 administers the first stimuli 21 to the patient such that the first stimuli 21 are received via the eye, the ears or the skin of the patient, depending on the modality, and are guided from their via the nerve system to the pathologically active neuron population 30 in the brain 29 and/or the spinal cord 29. The first stimuli 21 are adapted so that they suppress the pathological synchronous activity of the neuron population 30. A suppression of the synchronous activity can mean that the rate of coincidence of the neurons is reduced or that the neuron population 30 is indeed desynchronized. A reduction of the rate of coincidence of the neurons brought about by the stimulation can lead to a reduction of the synaptic weights and thus to an unlearning of the tendency to produce the pathological synchronous activity. Since the first stimuli 21 are therapeutically effective sensoric stimuli these are also referred as "specific" stimuli.

The second stimuli 22 generated by the second stimulation unit 12 are likewise received via the eyes, the ears or the skin as well as lower lying tissue of the patient depending on the modality and are guided from there to the nerve system. The second stimuli 22 when taken on their own, this means without the cooperation with the first stimuli 21 in the learning phase described in the following, have no or only a small desynchronizing effect or rate of coincidence lowering effect on the pathological synchronous neuronal activity of the neuron population 30. The second stimuli 22 applied by the second stimulation unit 12 are thus also referred to as "non-specific" stimuli.

On the application of optical (or visual) or acoustic (or auditory) first or second stimuli 21, 22 these are received by the patient via at least one eye or via at least one ear. The tactile, vibratory and thermal first or second stimuli 21, 22 (or touch stimuli, vibration stimuli and thermo stimuli) are received by receptors lying in or beneath the skin and are guided to the nerve system. These receptors include, for example, Merkel cells, Ruffini bodies, Meissner bodies and hair follicle receptors which, in particular act as receptors for the tactile stimuli 21, 22. The vibratory stimuli 21, 22 are primarily intended for depth sensibility. The vibratory stimuli 21, 22 can be received by receptors lying in the skin, the muscles, the subcutaneous tissue and/or the tendons of the patient. The Vater-Pacini bodies are mentioned by way of example as receptors for the vibratory stimuli 21, 22 which convey the perception of vibration and acceleration. The thermal stimuli 21, 22 are received by the thermo receptors of the skin. These are warm receptors (also known as heat receptors, warm sensors or heat sensors) and cold sensors (also known as cooling sensors, cold receptors or cooling receptors). The cold sensors lie towards the surface, the warm receptors a little deeper in the skin of the human.

The apparatus 100 can be operated in two different modes of operation for application of the first and second stimuli 21, 22. The respective mode of operation can, for example, be predetermined or it can be selected by the control unit 10. The control unit 10 controls the two stimulation units 11 and 12 in accordance with the selected mode of operation.

In a first mode of operation, which is also referred to as learning phase, the non-specific second stimuli 22 are administered to the patient, at least partly, closely coupled in time to the application of the specific first stimuli 21, this means that the first and second stimuli 21, 22 are at least partly administered in pairs in the first mode of operation. The nerve system of the patient is hereby conditioned, this means that it learns to react to the non-specific second stimuli 22 in the same way as to the specific first stimuli 21 (or in a slightly attenuated form), also when the specific first stimuli 21 are not administered. This is utilized in that, in the second mode of operation, in the actual stimulation phase, the first and second stimuli 21, 22 are not always administered in pairs; rather also non-specific second stimuli 22 are administered on their own between such pairs of first and second stimuli 21, 22. Since the non-specific second stimuli 22 also achieve therapeutic effects through the conditioning of the nerve system of the patient achieved in the first mode of operation, i.e. in the learning phase, the demand for specific first stimuli 21 is reduced in the second mode of operation.

One can stimulate only with the non-specific second stimuli 22 for longer periods of time for an efficient conditioning, without the first stimulation unit 11, which serves for the administration of the specific first stimuli 21, having to be worn or used by the patient. In contrast to the first stimulation unit 11, the second stimulation unit 12, by means of which the non-specific second stimuli 22 are generated, is generally significantly more comfortable (see e.g. the conditioning clock described in the following).

For the visual stimulation with specific optical first stimuli 21, for example, transmission eyeglasses are used which e.g. temporarily and/or partially darken the viewing field which on carrying out daily activities and, in particular on guiding a vehicle, can be significantly cumbersome and/or dangerous. Whereas a pleasant non-specific vibratory second stimulus 22 is significantly more comfortable and, for example, also more acceptable than an application of specific sequences of tones for hours. As long as the specific first stimuli 21 are applied by means of a plurality of vibration actuators the wearing of the actuators—depending on their spatial positioning—can possibly be difficult and can even be disturbing for everyday tasks.

Through the increased comfort on carrying out the therapy, the willingness of the patient to carry out the therapy (compliance) and thus of the therapeutic result can be increased as a whole.

In FIGS. 2A and 2B the differences between the application of the first and second stimuli 21, 22 in the first and second mode of operation are graphically illustrated by way of example. In FIG. 2A two first sections of time $\Delta t_1$ and second sections of time $\Delta t_2$ are shown beneath one another and are applied against the time during which the first stimuli 21 and/or the second stimuli 22 are generated in the first mode of operation and administered to the patient. The sections of time $\Delta t_1$ and $\Delta t_2$ are respectively illustrated by rectangles. From FIG. 2A it can be seen that the generation and application of the non-specific second stimuli 22 is coupled to the generation and application of the specific first stimuli 21 in the first mode of operation. The sections of time $\Delta t_1$ and $\Delta t_2$ are present pair-wise in the learning phase. Through the paired application of the first and second stimuli 21, 22 the brain 29 and/or the spinal cord 29 of the patient are conditioned, this means that following the learning phase (e.g. already after two or more paired sections of times $\Delta t_1$ and $\Delta t_2$) also a non-specific second stimulus 22, which is applied without an additional specific first stimulus 21 brings about a therapeutic effect like a specific first stimulus 21. Before this learning phase a non-specific second stimulus 22 would not have brought about a therapeutic effect.

The duration of the section of time $\Delta t_1$ in which the specific first stimuli 21 are applied, amounts to e.g. between 30 minutes and 6 hours can, however, also lie outside of this range. The duration of the sections of times $\Delta t_2$ in which the non-specific second stimuli 22 can be administered amounts to e.g. between 10 minutes and 6 hours can, however, also lie outside of this range. The sections of time $\Delta t_1$, for example, overlap with the respectively associated sections of time $\Delta t_2$ in the first mode of operation. This overlap $\Delta t_{12}$ amounts to e.g. at least 10% or 20% or 30% or 40% or 50% or 60% or 70% or 80% or at least 90% or even 100% of the respective section of time $\Delta t_2$. For sections of time $\Delta t_1$ and $\Delta t_2$ associated with one another as is illustrated in FIG. 2, the section of time $\Delta t_2$ can initially start; however, it is alternatively also possible that one starts with the section of time $\Delta t_1$. Pauses are adhered to between subsequent pairs of first and second stimuli 21, 22 whose length $\Delta t_{pause}$ can amount to e.g. between 3 hours and 24 hours. Both the length of the sections of time $\Delta t_1$ and $\Delta t_2$ and also of the overlap time periods $\Delta t_{12}$, as well as the stimulation pauses $\Delta t_{pause}$ can be varied during a stimulation phase. The duration of the learning phase, this means the duration in which the apparatus is operated in the first mode of operation, can be predetermined and can, for example, comprise a predetermined number of paired sections of time $\Delta t_1$ and $\Delta t_2$.

In the following examples for the application of the first and second stimuli 21, 22 during the learning phase will be described. In accordance with an example first stimuli 21 and/or second stimuli 22 can be administered during a section of time $\Delta t_1$ of 6 hours and a section of time $\Delta t_2$ of 6.25 hours, wherein the section of time $\Delta t_2$ starts 15 minutes before the section of time $\Delta t_1$ and both of the sections of time $\Delta t_1$ and $\Delta t_2$ end simultaneously. Following a pause $\Delta t_{pause}$ of e.g. 6 hours this process can be repeated. In order to achieve a rapid learning and/or conditioning of the nerve system the number of the learning events, this means the paired administration of first and second stimuli 21, 22, can be further increased with regard to the aforementioned example. For example, the sections of time $\Delta t_1$ and $\Delta t_2$ can be reduced to e.g. 3 or 3.125 hours, wherein the section of time $\Delta t_2$ starts 7.5 minutes before the section of time $\Delta t_1$. Following a pause $\Delta t_{pause}$ of e.g. 3 hours the coupled stimulation can be carried out again.

A learning effect can possibly already be brought about after two applications of first and second stimuli 21, 22 coupled with one another. In order to design the conditioning of the nerve system as robust as possible and to utilize the conditioning in the actual stimulation phase as long as possible, for example, 10 to 50 pair administrations can be carried out in the learning phase, this means in the first mode of operation.

Each section of time $\Delta t_2$ must not necessarily be associated with a section of time $\Delta t_1$ during the learning phase. For example, a section of time $\Delta t_1$ or a section of time $\Delta t_2$ which is not coupled to an associated section of time $\Delta t_1$ or $\Delta t_2$ can be introduced and during which introduction merely first stimuli 21 or second stimuli 22 are generated and are applied following a certain number of sections of times $\Delta t_1$ and $\Delta t_2$ coupled with one another. For example, at least 50% or 60% or 70% or 80% or 90% or even 100% of the section of time $\Delta t_2$ can be coupled to an associated section of time $\Delta t_1$ in the first mode of operation. Moreover, at least 50% or 60% or 70% or 80% or 90% or even 100% of the sections of time $\Delta t_1$ can be coupled to an associated section of time $\Delta t_2$ in the first mode of operation.

Following the learning phase carried out in the first mode of operation the actual stimulation phase takes place. For this purpose, the control unit 10 switches into the second mode of operation. By way of example the sections of time $\Delta t_1$ and $\Delta t_2$ are applied against the time t below one another in FIG. 2 during which time t the first stimuli 21 or the second stimuli 22 are generated and applied in the second mode of operation.

In the actual stimulation phase the fact is utilized that non-specific second stimuli 22 also have a therapeutic effect due to the conditioning of the nervous system of the patient achieved in the learning phase. For this purpose—in contrast to the learning phase—pairs composed of first and second stimuli 21 and 22 are not primarily applied but rather only second stimuli 22 are also applied during a section of time $\Delta t_2$ which is not coupled to the application of the first stimulus 21. For example, no section of time $\Delta t_1$ is associated with at least 10% to 20% or 30% or 40% or 50%) or 60% or 70% or 80% or 90% of the sections of time $\Delta t_2$ in the second mode of operation, this means that the number of sections of time $\Delta t_1$ is as a whole smaller than the number of the second sections of time $\Delta t_2$ in the second mode of operation. Sections of time $\Delta t_1$ can also be introduced sporadically which are not coupled to a section of time $\Delta t_2$ in accordance with an embodiment. In accordance with a further embodiment, it can also be provided that e.g. no section of time $\Delta t_1$ is associated with sections of time $\Delta t_2$ and that no first stimuli 21 are applied in the second mode of operation in the second mode of operation.

The pairs "P" composed of specific and non-specific stimuli 21, 22 and the non-specific stimuli "U" applied alone can be administered in the second mode of operation, e.g. in periodic sequences, e.g. in the following sequence: P-P-U-U-U-P-P-U-U-U-P-P-U-U-U- . . . . The timely pattern in accordance with which the non-specific second stimuli are present alone, can however, also be selected deterministically or stochastically or mixed deterministic-stochastically, e.g. the following sequence can be selected: P-P-U-U-U-P-P-U-U-U-U-U-P-P-U-U-U-P-P-U-U-P-P-U-U-U-U-P-P-U-U-U- . . . .

On application of pairs "P" of first and second stimuli 21, 22, the first and second stimuli 21, 22 are of different modality in accordance with an embodiment, this means that, for example, the first stimuli 21 are acoustic stimuli and the second stimuli 22 are vibratory stimuli. In accordance with a further embodiment the first and second stimuli 21, 22 applied as a pair "P" have the same modality.

Figure 3:
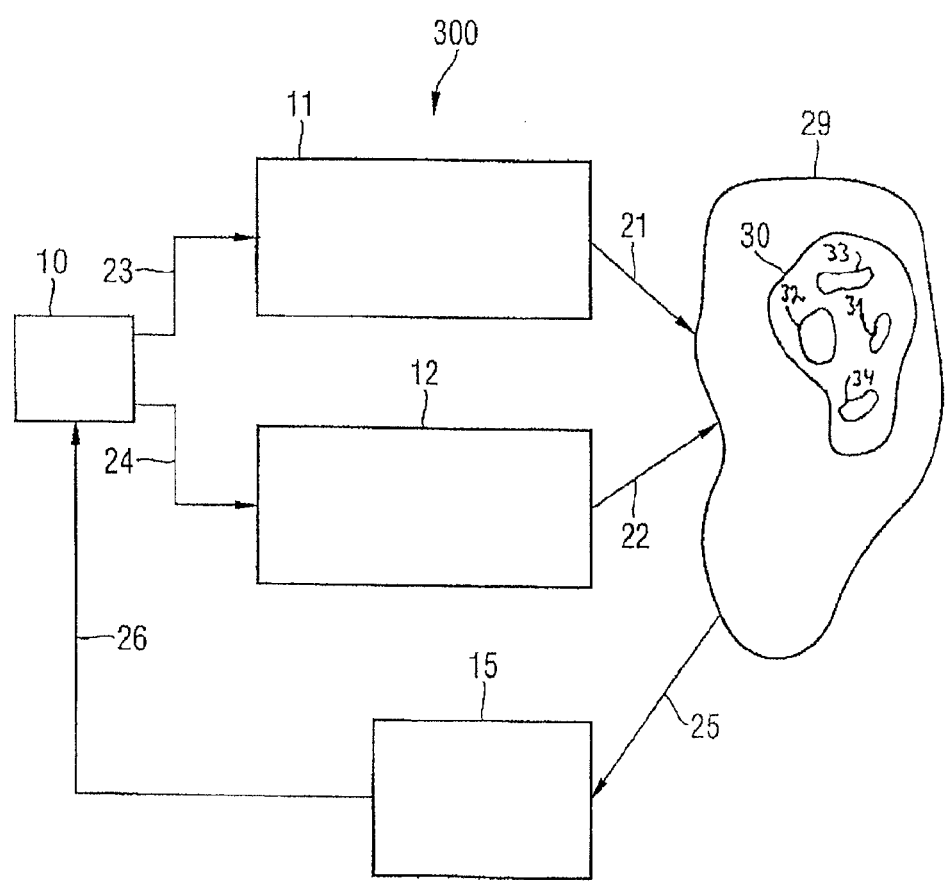
FIG. 3 a schematic illustration during the operation of an apparatus for the conditioned desynchronized non-invasive stimulation in accordance with a further embodiment.

The stimulation effect achieved by means of the apparatus 100 can, for example, be controlled with the aid of a measurement unit. An apparatus 300 which includes such a measurement unit 15 is schematically illustrated in FIG. 3. The remaining components of the apparatus 300 are identical to those of the apparatus 100 shown in FIG. 1. The measurement unit 15 records one or more of the measurement signals 25 measured at the patient, converts these possibly into electrical signals 26 and guides these to a control unit 10. In particular the neuronal activity in the stimulated target region, this means that e.g. the neuronal activity of the neuron population 30 schematically illustrated in FIG. 3, or a region associated with the neuron population 30 can be measured by means of the measurement unit 15.

The measurement unit 15 can be implanted into the body of the patient in the form of one or more sensors. For example, deep brain electrodes, subdural or epidural brain electrodes, subcutaneous EEG electrodes and subdural or epidural spinal cord electrodes can serve as invasive sensors. Furthermore, electrodes to be attached at peripheral nerves can be used as sensors.

The measurement signals 25 can be recorded continuously or in pauses between the administration of the specific first stimuli 21, however, in particular also during or after the subsequent administration of the non-specific second stimuli 22. As long as the neuronal activity of the target population 30 is measured the amplitude of the pathological oscillation can be determined in typical frequency ranges of the local field potentials, thus e.g. for akinetic Parkinson's patients the integral performance can be determined in the beta frequency range between 10 and 30 Hz. This amplitude decreases on an effective stimulation. If the stimulation effect of the non-specific second stimuli 22 applied on their own reduces in the second mode of operation and the measured amplitude exceeds a predetermined threshold value then the next learning phase can take place in the first mode of operation. Thereafter the actual stimulation can be carried out again in the second mode of operation.

The threshold value can be set individually for the respective patient by the doctor. Alternatively, typical values can be selected as a presetting of the threshold value, e.g. the mean value of the amplitude plus twice the standard deviation can be selected in ranges of the frequency spectrum which have no frequency peaks and are above of e.g. 70 Hz.

Also one or more non-invasive sensors can be used as an alternative to the invasive sensors or also in addition to these. The advantage of the use of the exclusively non-invasive sensors is that no single component of the apparatus must be implanted in this case. Non-invasive sensors are e.g. electroenzephalographs-(EEG)-electrodes, magnetoenzephalography(MEG)-sensors and electromyography-(EMG)-electrodes. Moreover, the pathological oscillatory activity can be measured in the tremor frequency range or the lack of movement (in the sense of reduction of the overall movement) can be measured e.g. by an accelerometer. If a predetermined value of the tremor activity is exceeded and/or a critical value of the mean hourly activity (outside of the night times) is undershot then the next learning phase starts in the first mode of operation, for example.

In accordance with an embodiment two threshold values are used for the control of the two modes of operation. For example, two threshold values $A_L$ and $A_S$ can be provided by means of which e.g. the amplitude measured by the measurement unit 15 is compared to a symptom. The threshold value $A_L$ can be larger than the threshold value $A_S$ and can illustrate the coarser of the two threshold values. If the amplitude of the symptom exceeds the value $A_L$, then a switch is made from the second mode of operation into the first mode of operation and a learning phase is carried out again.

If the amplitude of the symptom exceeds the finer threshold value $A_S$ during the second mode of operation then a switch into the first mode of operation is not made, but the apparatus 300 remains in the actual stimulation phase; however, pairs "P" of specific first stimuli 21 and non-specific second stimuli 22 are applied in an increasing manner. For this purpose, for example, a partial sequence composed only of non-specific stimuli "U" (-U-U-U-U-U-) can be skipped and a skip is made to the next section in the sequence which has the pairs "P" of specific and non-specific stimuli 21, 22. As long as it is provided that, for example, a certain percentage of the second stimuli 22 are applied together with the first stimuli 21 in the second mode of operation then this percentage of the pairs "P" can be increased on exceeding the threshold value $A_S$ by a specific percentage number. It shall now be considered as an example that 30% of the second stimuli 22 are applied as pairs "P" together with the first stimuli 21 in the second mode of operation. On exceeding the threshold value $A_S$ this percentage can, for example, be increased by 20% to 50%. As soon as the measured amplitude of the symptom then again undercuts a further predetermined threshold value one can revert again to 30% provided by way of example in the second mode of operation.

E.g. the beta band activity of the neuron population 30 measured by an invasive sensor can be utilized as a measurement value whose amplitude is compared to the threshold values $A_L$ and $A_S$. The mean amplitude of the tremor activity measured by an accelerometer can, for example, be used as a measurement value for a non-invasive sensor.

Moreover, the movement of the patient measured by the accelerometer can be utilized as a comparison value. In this case, the coarser threshold value $A_L$ is, however, smaller than the threshold value $A_S$. An increased amount of pairs "P" of specific first stimuli 21 and non-specific second stimuli 22 are applied in the second mode of operation as long as the mean amplitude of the movement of the patient undercuts the finer threshold value $A_S$. If the mean amplitude of the movement undercuts the value $A_L$ then a switch is made from the second mode of operation into the first mode of operation and a learning phase is once again carried out. This treatment can in particular be used for akinetic Parkinson's patients.

The transition from the second mode of operation into the first mode of operation can also be controlled by the patient through an external patient programming device. This means that the patient has the possibility of pressing a button on a small manageable external device when he does not feel satisfactorily treated i.e. when his tremor or his immovability is too strong, for example. Following a predefined mode the control unit 10 then switches from the second mode of operation into the first mode of operation, i.e. into an afresh learning phase. The predefined mode in this context means that this transition into the first mode of operation is e.g. already executed through the first push of a button by the patient. The apparatus 100 and/or 300 can, however, also be set by the doctor so that the transition into the first mode of operation only takes place after a small number of such pushes of the buttons during a predefined time interval, e.g. after three pushes of the button per half an hour. Moreover, two threshold values $A_L$ and $A_S$ can also be used in this embodiment. Should the number of pushes of the button per patient within a predetermined time interval exceed the finer threshold value $A_S$ during the second mode of operation then an increased amount of pairs "P" of specific first stimuli 21 and non-specific second stimuli 22 are applied. A switch is made into the learning mode if the number of pushes of the button exceeds the threshold value $A_S$.

For therapy control the apparatus 100 and/or 300 registers the number and the points in time of the pushes of the button. This information can then be read out by the doctor by means of a external programming device designed for the doctor.

It can furthermore be provided that a change is again made from the second mode of operation into the first mode of operation, i.e. into the learning phase, after a predefined duration of time. A therapy control with the aid of the measurement unit 15 is not necessarily required for this change of mode, this means that this change of mode can be implemented both in the apparatus 100 and also in the apparatus 300.

The second stimulation unit 12 can include e.g. a loudspeaker, a light source (e.g. an image source), a vibrator and/or a thermo element for the generation of the non-specific second stimuli 22. Generally speaking, the second stimuli should be strong enough so that they can be intentionally perceived by the patient. They should, however, neither be considered to be e.g. uncomfortably strong nor interfering or even distracting. For example, a dialing tone, a humming noise or a melody can be used as acoustic second stimuli 22 which are generated by the loudspeaker during the section of time $\Delta t_2$. As long as optical signals should be used as second stimuli 22 these can e.g. be abstract or representational patterns which change either statically or change in time during the sections of time $\Delta t_2$, e.g. a blossom which moves in the wind, a fish which swims in water, a bird which flies, a sun which rises, etc. Tactile and/or vibratory second stimuli 22 can be vibrations with frequencies perceptible by the patient which are generated by a mechanic vibrator during the sections of time $\Delta t_2$. Perceptible vibration stimuli can have frequencies in the range of 10 to 160 Hz or also above these, while tactile stimuli have significantly lower frequencies which are e.g. smaller than 1 Hz. Mixed forms of tactile and vibratory stimuli can also be used. The tactile and/or vibratory second stimuli 22 can e.g. be selected by the patient himself as comfortable. A soft, comfortable massaging effect can moreover be carried out at the skin of the patient during the sections of time $\Delta t_2$ by means of the vibrator. Heat stimuli or also cooling stimuli can be used as thermal second stimuli 22. Although cooling stimuli have a better resolution in time (which is however not required for the non-specific stimuli) the heat stimuli are preferred, since cooling stimuli are perceived by the patient as less comfortable (apart from during the high summer).

The non-specific second stimuli 22 can be administered continuously to the patient from the start to the end of each respective section of time $\Delta t_2$. Alternatively also pauses in application can be maintained during the sections of time $\Delta t_2$, for example, the second stimuli 22 can be administered in certain time intervals with application pauses lying there between during the sections of time $\Delta t_2$. This pattern in time can also be varied, e.g. stochastically or deterministically or mixed stochastic-deterministically. It can be provided that the second stimuli 22 are applied during 60% or 70% or 80% or 90% of the duration of time of a respective section of time $\Delta t_2$.

Optical stimuli, acoustic stimuli, tactile stimuli, vibratory stimuli and/or thermal stimuli are used as specific first stimuli 21 which have a desynchronizing effect or at least bring about a reduction of the rate of coincidence of the pathological neurons. It is described in the following that it is possible to stimulate different regions of the brain 29 or spinal cord 29 separately by means of the stimulation unit 11, in that the applied first stimuli are guided to different target regions, which lie in the brain 29 and/or in the spinal cord 29, via nerve lines. The target regions can be stimulated during the stimulation period of time $\Delta t_1$ with possibly different first stimuli 21 and/or time-shifted first stimuli 21.

In accordance with an embodiment, first stimuli 21 are administered to the neuron population 30 which has a pathological synchronous and oscillatory activity which brings about a reset, a so-called setting back, of the phase of the neuronal activity of the stimulated neurons. The phase of the stimulated neurons is set independently from the current phase value to a certain phase value, e.g. of 0°, through the reset. Thus, the phase of the neuronal activity of the pathological neuron population 30 is controlled by means of a targeted stimulation. Since it is moreover possible to stimulate the pathological neuron population 30 at different positions, the phase of the neuronal activity of the pathological neuron population 30 can be reset at the different stimulation positions to different points in time. As a result the pathological neuron population 30, whose neurons were previously synchronously active and active with the same frequency and phase, can be divided into a plurality of sub-populations which are schematically illustrated in FIG. 3 and are referred to with the reference numerals 31, 32, 33 and 34 (by way of example four sub-populations are illustrated in this example). Within one of the sub-populations 31 to 34 the neurons are still synchronous and also still fire with the same pathological frequency after a reset of the phase; however, each of the sub-populations 31 to 34 has the phase which is imposed thereon by the stimulation stimulus with regard to its neuronal activity. This means that the neuronal activity of the individual sub-populations 31 to 34 still has an approximately sinusoidal extent with the same pathological frequency after their reset; however, with different phases.

The state with at least two sub-populations brought about by the pathological interaction between the neurons generated by the stimulation is instable and the overall neuron population quickly approximates to a state of complete desynchronization in which the neurons fire in an uncorrelated manner. The desired state this means the state of complete desynchronization is thus not immediately present after the application of the first stimuli 21, but is rather typically set within a few periods or even in less than a period of the pathological frequency.

A theory for the explanation of the stimulation success is based thereon that the finally desired desynchronization is only enabled by the pathologically increased interaction between the neurons. Hereby a self-organization process is utilized which is responsible for the pathological synchronization. The same causes a desynchronization to follow a splitting up of an overpopulation 30 into sub-populations 31 to 34. In contrast to this no desynchronization would take place without an increased pathological interaction of the neurons.

Furthermore, a new organization of the connectivity of the disordered neuronal networks can be achieved through the electrical stimulation with the apparatus 100 and/or 300 so that sustainable therapeutic effects of long duration can be brought about. The achieved synaptic conversion is of large importance for the effective treatment of neurological or psychiatric diseases.

Stimulation Units for the Generation of Non-Specific Stimuli

Figure 4A:
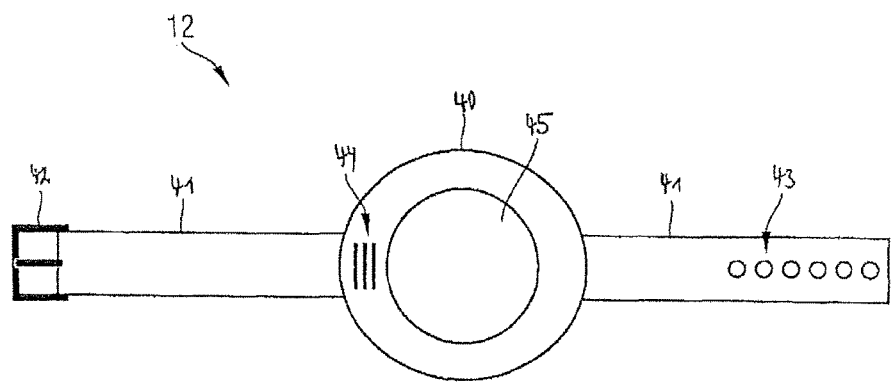
FIGS. 4A and 4B schematic illustrations of a stimulation unit for the generation and application of non-specific optical, acoustic, tactile, vibratory and/or thermal stimuli in accordance with an embodiment.
Figure 4B:
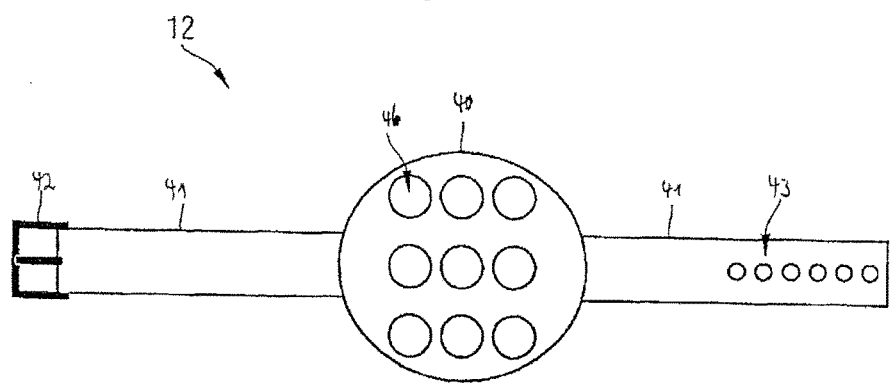
Figure 5:
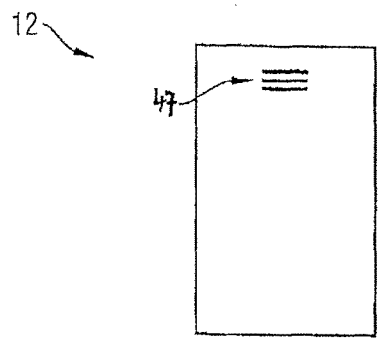
FIG. 5 a schematic illustration of a stimulation unit for the generation and application of non-specific acoustic stimuli in accordance with a further embodiment.

Embodiments of the non-invasive second stimulation unit 12 for the generation of the non-specific second stimuli 22 are illustrated in the FIGS. 4A, 4B and 5. In the embodiment shown in the FIGS. 4A and 4B, the second stimulation unit is designed as a so-called "conditioning clock" which is comfortable to wear for the patient. The front view of the conditioning clock 12 is shown in FIG. 4A, the rear view of the conditioning clock 12 is shown in FIG. 4B. The conditioning clock 12 is composed of a middle part 40, arm bands 41, a closure part 42 and associated holes 43. Alternatively also a hook and loop fastener or any other type of closure on par therewith can be used. The middle part 40 includes a loudspeaker 44 for the generation of non-specific acoustic stimuli 22, e.g. a melody or a comfortable ring tone, as well as a display 45 for the generation of a comfortable, non-blinding, non-specific optical stimulus 22, e.g. a blossom moving in the wind or an abstract light pattern with light and warm colors. The conditioning clock 12 can moreover be equipped with one or more vibrators 46 which generate the non-specific tactile and/or vibratory stimuli 22. The vibrators can be operated, e.g. with a frequency of less than 1 Hz, for the generation of tactile stimuli 22. In particular the movable parts of the vibrators 46 can be aligned in this case so that the pressure stimuli can be better realized, this means that the main movement direction of the vibrators 46 should be directed into the skin. The tactile stimuli 22 can moreover also be generated by pressure actuators or elements which move slowly relative to the skin, which can e.g. be integrated into the conditioning clock. As long as vibratory stimuli 22 should be generated by means of the vibrator 46, vibration frequencies in the range of 10 to 160 Hz or there above can be used. In this case the movable parts of the vibrator 46 can have a pronounced movement direction substantially parallel to the skin surface. Movements perpendicular to the skin surface are likewise possible. The vibrators 46 can also be operated so that they simultaneously generate tactile and vibratory stimuli 22.

In accordance with an embodiment a thermo stimulator is arranged at the backside of the conditioning clock 12 with which the thermal second stimuli 22 can be administered to the skin of the patient.

The conditioning clock 12 can also be designed so that it only generates one non-specific stimulus 22 of a sense modality, e.g. only one optical stimulus. The current supply of the condition clock 12 takes place through a battery and/or solar cells and/or a mechanical fly wheel in the interior of the conditioning clock 12.

For the control of the stimulation effect the conditioning clock 12 can additionally include an accelerometer with which the pathological oscillatory activity, e.g. of pathological tremors or, however, the mean activity level of the patient can be measured. The mean activity level of the patient represents the slowing down and/or degradation of the movement and/or of the movement capability of the patient (this means the Bradykinesia, hypokinesia and akinesia).

A further embodiment of the non-invasive second stimulation unit 12 is schematically illustrated in FIG. 5. In this respect it can, for example, be a cell phone-shaped stimulator, which can be carried e.g. in the shirt pocket or trouser pocket of the patient and which generates non-specific acoustic stimuli 22 by means of a loudspeaker 47.

An external programming device can moreover be provided for the doctor with which the parameters of the control unit 10, the specific stimulation unit 11 and/or the non-specific physiological stimulation unit 12 can be set. Furthermore, an external programming device can likewise be provided for the patient, with which the patient can switch off the stimulation device and/or modify parameters of the stimulation units 11 and 12 in narrow boundaries predefined by the doctor. Moreover, the programming device designed for the patient can include the functionality already described above by means of which the patient can autonomously bring about a switch from the second mode of operation into the first mode of operation, i.e. into the learning phase e.g. through the actuation of a button when the patient does not feel treated sufficiently, this means that e.g. when his tremor or his immovability are too strong. The programming device can, for example, communicate via radio communication with the respective components of the stimulation device.

Stimulation Units for the Generation of Specific Optic Stimuli:

In the following embodiments of the non-invasive first stimulation unit 11 for the generation of optical first stimuli 21 will be described. Such stimulation units can also be found in the German patent application no. 10 2008 012 669.1 having the title "Apparatus and method for the visual stimulation" which was filed at the German Patent and Trademark Office on Mar. 5, 2008. The overall content of disclosure of the German patent application no. 10 2008 012 669.1 is hereby incorporated into the disclosure of the present application.

Reference will only be made in the following to the generation of the optical first stimuli 21. It is naturally understood that these specific first stimuli 21 are applied in combination with the non-specific second stimuli 22 as was described above, for example, in connection with the FIGS. 1 to 5.

Figure 6:
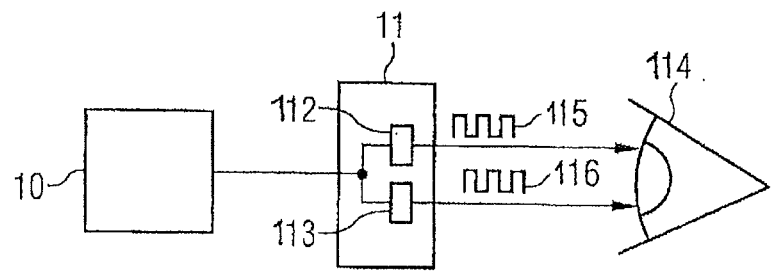
FIG. 6 a schematic illustration of a stimulation unit for the generation and application of specific optical stimuli in accordance with an embodiment.

FIG. 6 schematically shows an embodiment of the first stimulation unit 11 which includes a plurality of stimulation elements. In the present embodiment the stimulation unit 11 has two stimulation elements 112 and 113 which are controlled by the control unit 10. An eye 114 of a patient is further illustrated in FIG. 6.

During the operation of the first stimulation unit 11 the stimulation elements 112 and 113 generate optical first stimuli 115 and/or 116 which are received by the patient via one or both eyes 114 and are guided to neuron populations in the brain via the optical nerves. The control unit 10 controls the stimulation elements 112 and 113 in this respect such that the optical first stimuli 115 and 116 are generated e.g. displaced in time.

Instead of a time shifted application of the optical first stimuli 115 and 116 these can also be applied with different phases or with different polarities. Moreover, also mixed forms are plausible, this means that the optical first stimuli 115 and 116 can e.g. be shifted in time and have different polarities. The first stimulation unit 11 can be designed so that, for example, only one of the previously mentioned stimulation variants can be carried out therewith or the first stimulation unit 11 can alternatively be designed so that one or more of the mentioned stimulation variants can be carried out therewith.

The optical first stimuli 115 and 116 can be based on a variation of the light strength and/or brightness (or variation of the light intensity or of the light strength), for example, they can be applied as a pulse or as a sequence of pulses with varying light strength and/or brightness. The optical first stimuli 115 and 116 can, depending on the design of the first stimulation unit 11, be administered as light strength modulated natural optical stimuli, administered e.g. by means of homogenous or segmented transmission eyeglasses, as a modulated optical stimulus present in addition to a naturally present optical stimulus, administered e.g. by means of partially transparent light eyeglasses, or as an artificial optical brightness stimulus, administered e.g. by means of non-transparent light eyeglasses. If the patient receives the optical first stimuli 115, 116 via both eyes 114, the respective optical first stimuli 115, 116 of both eyes 114 can be correlated and/or coordinated.

The optical first stimuli 115, 116 generated by the stimulation elements 112, 113 are designed such that, when they are received by the retina and are guided to a neuron population with a pathologically synchronous and oscillatory activity, via the optical nerve they can bring about a reset of the phase of the neuronal activity of the stimulated neurons in the neuron population.

Figure 7:
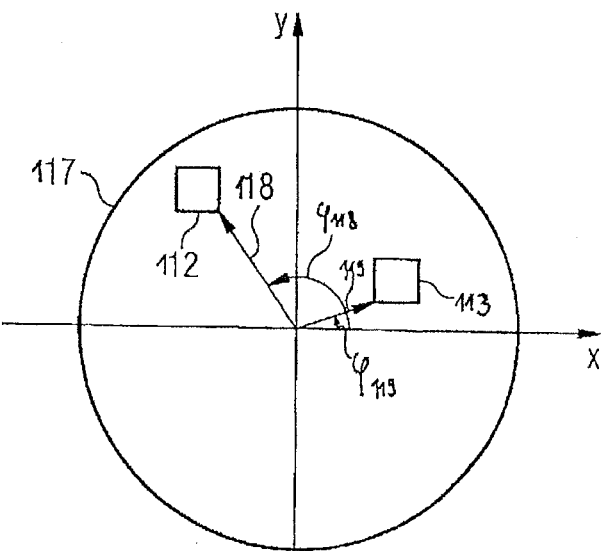
FIG. 7 a schematic illustration of the viewing field of a patient.

The viewing field 117 of a patient is schematically illustrated in FIG. 7. The space which is seen by an eye without eye movement is referred to as the viewing field. A viewing field 117 is illustrated in FIG. 7 for reasons of simplicity in circular shape. Typically the viewing field has a rather more ovally bulged shape. The precise size and shape of the viewing field in this respect underlies individual fluctuations and is also dependent on age. Points in the viewing field 117 can e.g. be described with the aid of their polar coordinates. The spatial positions of the stimulation element 112 and 113 in the viewing field 117 is illustrated by way of example in FIG. 7. For reasons of simplicity a respective edge point of the stimulation elements 112 and 113 is referred to with a vector 118 or 119. The vectors 118 and 119 can be described in the polar coordinate system via their amount and their angle $\varphi_{118}$ and/or $\varphi_{119}$, with which they enclose the x-axis.

Different points in the viewing field 117 are imaged via the lens of the eye at different positions at the retina. The different positions at the retina in turn are connected to different neurons in the brain via the optical nerve. This means that stimulation elements 112 and 113 arranged at the different spatial positions can respectively stimulate different neurons. Accordingly the stimulation elements 112 and 113 as well as possible further stimulation elements can be arranged spatially within the viewing field 117 of the patient so that optical stimuli received by the retina are guided to different target regions in the brain. According to this, different sub-populations of a pathological neuron population can be specifically stimulated with the stimulation elements 112 and 113 and a time displaced reset of the phases of these sub-populations can be carried out as is described above in connection with FIG. 3.

The association of the region of the viewing field with corresponding regions of the brain is, for example, described in the article "Visual Field Maps in Human Cortex" by B. A. Wandell, S. O. Dumoulin and A. A. Brewer, published in Neuron 56, October 2007, pages 366 to 383.

Figure 8:
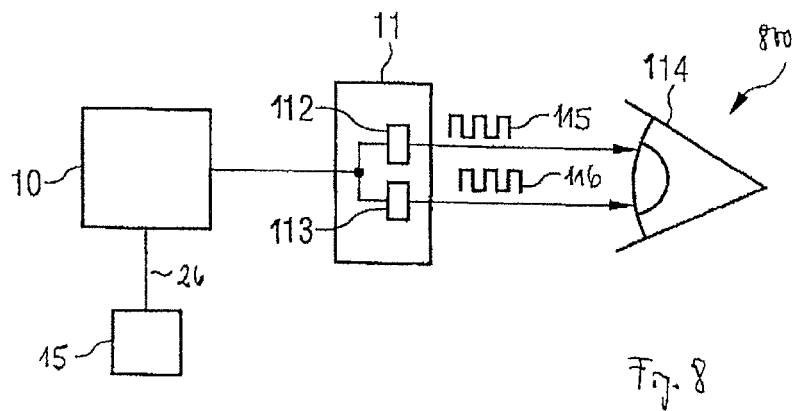
FIG. 8 a schematic illustration of a stimulation unit for the generation and application of specific optical stimuli in accordance with a further embodiment.

The first stimulation unit 11 can, for example, be operated in a so-called "open loop"-mode in which the control unit 10 controls the stimulation unit 11 such that the stimulation elements 112, 113 generate predetermined optical first stimuli 115, 116. Furthermore, the first stimulation unit 11 together with the control unit can also be further developed to a "closed loop" system as is schematically illustrated in FIG. 8. In this embodiment a measurement unit 15 is additionally provided which provides the measurement signals recorded at the patient and guides these to the control unit 10. The measurement unit 15 can be non-invasive or invasive sensors (cf. the above description in connection with FIG. 3).

Different designs are plausible with regard to the cooperation between the control unit 10 and the measurement unit 15. For example—as described above—a change is made between the first mode of operation, the learning phase, and the second mode of operation, the actual stimulation phase, by means of the measurement signals. Moreover, parameters of the optical first stimuli 115, 116, such as for example, the strength (amplitude) of the stimuli or the frequency of the stimulation or the pauses between the stimulation sequences can be set by the control unit 10 on the basis of the extent of the pathological features.

Furthermore, it can be provided that the measurement signals recorded by the measurement unit 15 are directly, or possibly following one or more processing steps, transformed into optical first stimuli and are applied by the first stimulation unit 11. For example, the measurement signals can be introduced as control signals at the control inputs of the stimulation elements 112, 113 in an amplified manner and possibly following a mathematic calculation (e.g. following a mixture of the measurement signals) with a time delay and linear and/or nonlinear processing steps. The calculation mode is in this respect selected so that the pathological neuronal activity is counteracted and the stimulation signals likewise decrease with decreasing pathological neuronal activity or are at least significantly reduced in their strength.

Figure 9:
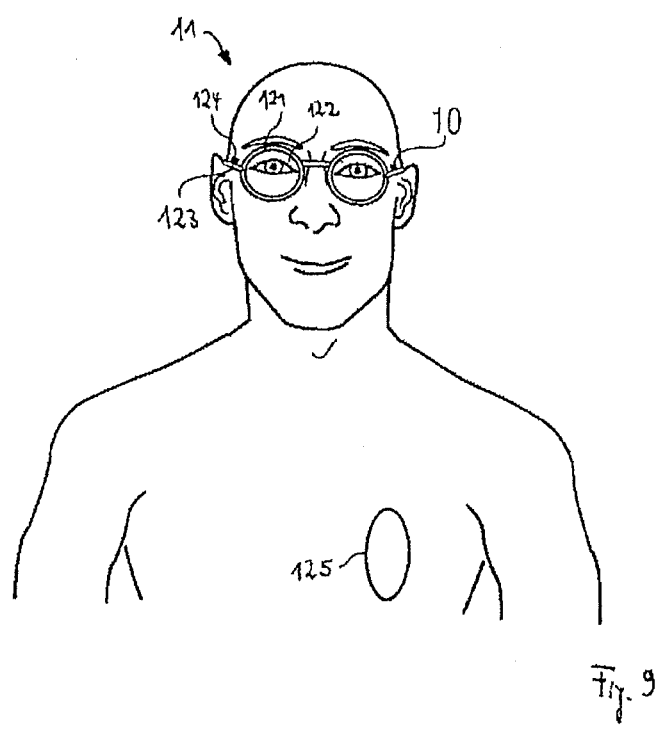
FIG. 9 a schematic illustration of a stimulation unit for the generation and application of specific optical stimuli in accordance with a further embodiment.

An embodiment of the first stimulation unit 11 as transmission eyeglasses is schematically shown in FIG. 9 which transmission eyeglasses are composed of the following components: (i) two mounting parts 121 each with a transmission modulated glass lens 122 (individually for each eye), (ii) two ear clips 123 with which the eyeglasses can be mechanically held behind the ear of the patient, and (iii) the control unit 10 which controls the transmission of the transmission modulated glass lenses 122 of the eyeglasses. Also one of the different eyeglasses described in the following, such as for example, partially transparent or non-transparent light eyeglasses, can be used as stimulation eyeglasses instead of transmission eyeglasses. A battery or a storage battery for current supply of the electrical components can be installed in the control unit 10 or can be arranged in or at the eyeglasses also structurally separate from a control unit 10. The eyeglasses can be switched on by the patient by means of an operating unit 124 (e.g. switch-on button and/or rotary switch). For example, the maximum stimulation strength can be set with the rotary switch. A control medium 125 can be provided in addition to the aforementioned components which, for example, is telemetrically connected to the control unit 10 or is connected to the control unit 10 via a connection cable. In the case of a connection on the basis of a cable plug connectors can be used for connecting and/or disconnecting.

Moreover, also a further control medium (not illustrated) can e.g. be provided which is to be operated by the doctor and which is telemetrically connected to the control unit 10 or is connected to the control unit 10 via a connection cable. In the case of a connection via a cable plug connectors can be used for connecting and/or disconnecting.

Furthermore, one or more sensors can be provided, e.g. EEG electrodes or an accelerometer, for registering and/or documenting the stimulation result and for investigation by the doctor.

Figure 10:
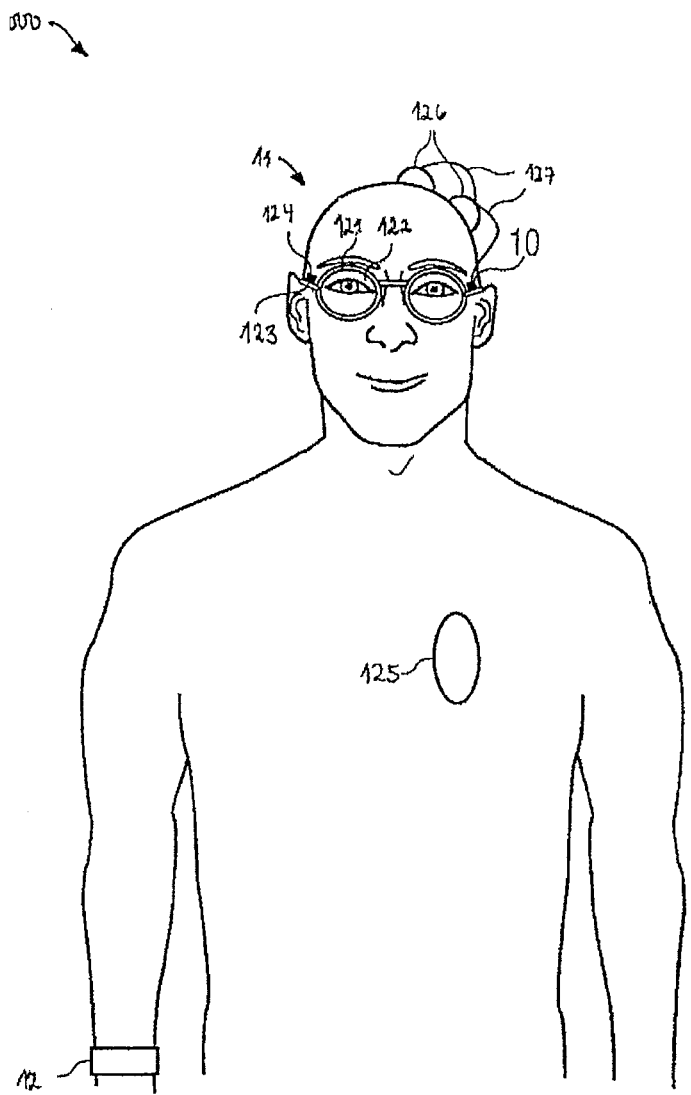
FIG. 10 a schematic illustration during the operation of an apparatus for the conditioned desynchronized non-invasive stimulation in accordance with a further embodiment.
Figure 11:
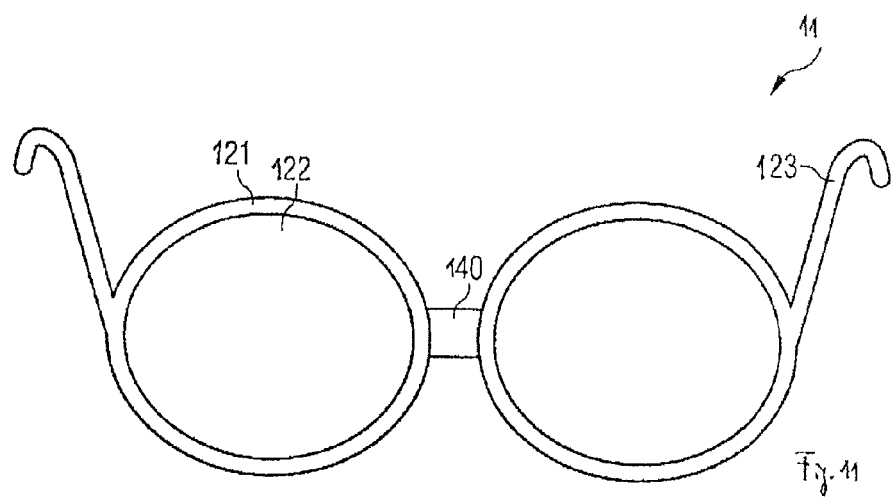
FIGS. 11 and 12 schematic illustrations of transmission eyeglasses.

FIG. 10 schematically shows an apparatus 1000 which has a first stimulation unit 11 adapted like that shown in FIG. 9, a measurement unit composed of EEG electrodes 126 as well as a second stimulation unit 12 for the application of the second, non-specific stimuli. All units of the apparatus 1000, this means the first and second stimulation unit 11, 12 as well as the measurement unit, are non-invasive units which do not have to be implanted into the body of the patient by means of an operation. The EEG electrodes 126 are epicutaneous, this means that they are attached at the skin of the patient and are connected to the control unit 10 via connection cables 127. The control unit 10 uses the measurement signals delivered by the EEG electrodes 126, e.g. for setting the mode of operation. The control unit 10 can, for example, also amplify the potential difference measured by means of the EEG electrodes 126 and use this signal following an optional linear or non-linear calculation for controlling the transmission modulated glass lenses 122 of the transmission eyeglasses. The EEG electrodes 126 can also be wireless, this means telemetrically connected to the control unit 10 as an alternative to the connection cables 127. This has the advantage that the patient is not hindered by the connection cable and can e.g. not get caught at barriers. The apparatus 1000 has the conditioning clock shown in FIGS. 4A and 4B as a second stimulation unit 12. The second non-specific stimuli can alternatively also be generated by means of a differently designed second stimulation unit 12.

Transmission eyeglasses 11 with homogeneous transmission glass lenses 122 are schematically illustrated in FIG. 1 as a first stimulation unit. The transmission eyeglasses 11 further comprise ear clips 123 for mechanical attachment of the patient head, a web 140 which connects the two transmission glass lenses 122, and mount parts 121 in which the transmission glass lenses 122 are mounted. The transmission glass lenses 122 are homogeneous, this means that they are not divided into segments differing from one another. The transmission of the right and the left transmission glass lens 122 can be regulated separately, this means that the transmission glasses 122 can be used as transmission elements 112 and 113 in the sense of the design illustrated in FIG. 6. Both eyes of the patient can be respectively stimulated with different optical first stimuli by means of the transmission eyeglasses 11.

Figure 12:
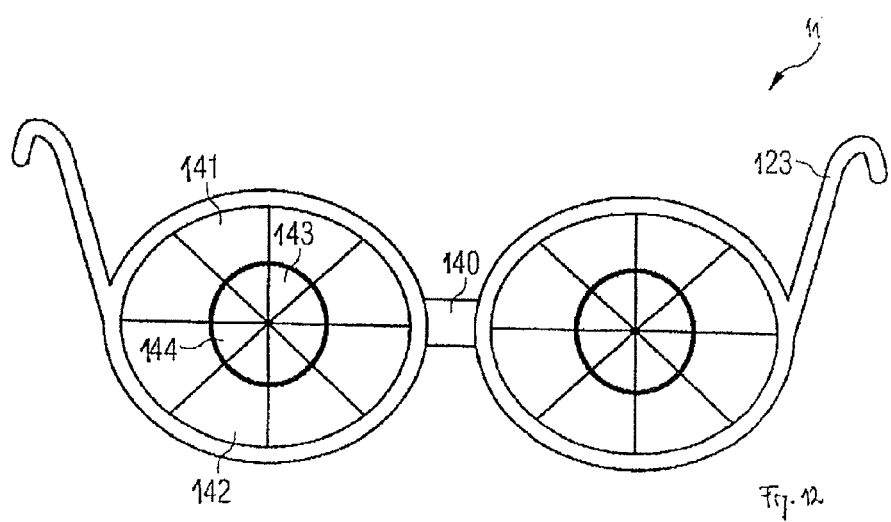

Transmission eyeglasses 11 with segmented transmission glass lenses are illustrated in FIG. 12. The transmission glass lenses are respectively divided into different segments whose transmission can be controlled separately. The segmentation can, for example, be radially and/or circular (both is shown in FIG. 12). The design of segmented transmission eyeglasses 11 shown in FIG. 12 is to be understood merely by way of example. The number of segments as well as the geometric shape of the individual segments can also be selected differently.

The segments of the transmission eyeglasses 11 correspond to the stimulation elements shown in FIG. 6. Four of the segments are referred to with reference numerals 141, 142, 143 and 144 by way of example in FIG. 12.

It shall be explained in the following by way of example how a desynchronization of the overall neuron population can be achieved through a time displaced reset of the phases of sub-populations of a pathological synchronous and oscillatory neuron population with reference to the segments 141 to 144. The segments 141 to 144 are selected so that the optical first stimuli generated thereby are respectively preferably received by a specific part of the retina of the patient, from where the stimuli are guided to specific regions of the brain, so that the above-described division of a pathological neuron population into sub-populations is enabled. So that sub-populations with different phases can be formed, the optical first stimuli can be generated by the segments 141 to 144, for example, displaced in time. A phase-shifted generation of the stimuli which likewise results in a time-shifted reset of the phases of the different sub-populations is of equal importance to the time displaced generation of the stimuli.

Figure 13:
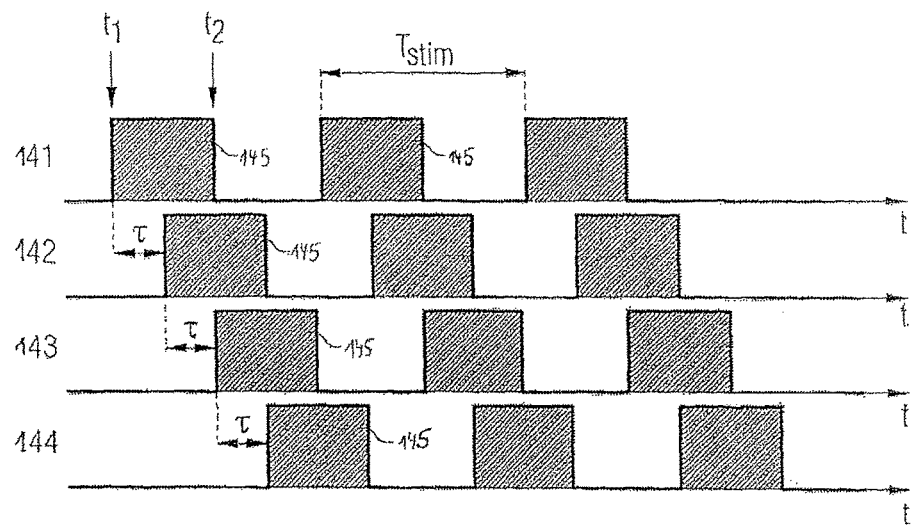
FIGS. 13 to 16 schematic illustrations of specific optical stimuli generated by means of transmission eyeglasses.

A stimulation method suitable for the above-described purpose which can, for example, be carried out with the previously described transmission eyeglasses 11 is schematically illustrated in FIG. 13. The optical first stimuli 145 applied by means of the segments 141 to 144 are shown beneath one another in FIG. 13 applied against the time t. For the embodiment shown in FIG. 13 it is assumed that only the segments 141 to 144 of the transmission eyeglasses 11 generate optical first stimuli 145, this means that only the transmission of these segments is modulated by the control unit 10. Naturally this should only be understood by way of example. For alternative embodiments other types of segments can be used for the generation of the optical stimuli instead of the segments 141 to 144. It is possible, like in FIG. 13, to only use a selection of the segments, or also all of the segments, of the transmission eyeglasses 11 for stimulation.

Each of the segments 141 to 144 periodically applies the optical first stimulus 145 in the method illustrated in FIG. 13. The stimulus 145 is applied three times per segment 141 to 144 in the present example. Alternatively, the stimulus 145 could, for example, also be repeated one to five times per sequence. The frequency $f_{stim}=1/T_{stim}$, with which the stimulus 145 can be repeated per segment 141 to 144, can lie in the range of 1 to 30 Hz, and, in particular in the range of 5 to 20 Hz can, however, also take on smaller or larger values. Such sequences of optical stimuli are suitable to reset the neuronal phase of a stimulated pathological sub-population of neurons.

The frequency $f_{stim}$ can, for example, lie in the range of the mean frequency of the pathological rhythmic activity of the target network. For neurological and psychiatrical illnesses the mean frequency typically lies in the range of 1 to 30 Hz can, however, also lie outside of this range. In this respect it must be noted that the frequency with which the pathological neurons synchronously fire is typically not constant, but by all means can be varied and can furthermore show individual deviations for each patient.

For determining the frequency $f_{stim}$, for example, the mean peak frequency for the pathological rhythmic activity of the patient can be determined. This peak frequency can then be used as the stimulation frequency $f_{stim}$ or can also be varied, for example, in a range of $f_{stim}-3$ Hz to $f_{stim}+3$ Hz. However, alternatively, a frequency $f_{stim}$ can be selected in the range of 1 to 30 Hz without a previous measurement and this can, for example, be varied during the stimulation until the frequency $f_{stim}$ is found with which the best stimulation result can be achieved. A literature value known for the respective illness can be utilized as a further alternative for the stimulation frequency $f_{stim}$. This value can possibly still be varied until, for example, ideal stimulation results are achieved.

The structure of an individual optical first stimulus 145 shall be explained in the following with reference to the first stimulus 145 generated by the segment 141. At the point in time $t_1$ the segment 141 is controlled by the control unit 10 in this example such that the transmission, this means the light permeability of the segment 141 becomes minimal. At the point in time $t_2$ the control unit 10 switches the transmission of the segment 141 to the maximum value. In other words this means that the segment 141 is less transparent when it is stimulated. Correspondingly the patient perceives a reduced brightness of the surrounding light in the region of the segment 141 during the stimulation.

Alternatively, it is also possible to switch the transmission of the segment 141 to a maximum at the point in time $t_1$ and to a minimum at the point in time $t_2$, so that the segment 141 becomes more transparent during the stimulation.

Principally it is plausible to select a maximum transmission of 100%, this means that the surrounding light is not attenuated at all through the respective segment in this case. Such a high transmission can, however, frequently not be achieved due to technical limitations so that smaller transmission values can be selected in the range of 60% to 100% for the maximum transmission. The minimum transmission can take on a value in the range of 0% to 30%. However, stimulation results can also still be achieved with transmission values which lie outside of the provided ranges.

The duration of an optical first stimulus 145, this means the time spam between the point in time $t_1$ and $t_2$ can, for example, amount to $T_{stim}/2$. In this case the time span during which it is stimulated and the subsequent stimulation pause can be of equal length. However, it is also possible to select different durations of stimulation, for example, in the range of $T_{stim}/2-T_{stim}/10$ up to $T_{stim}/2+T_{stim}/10$. Also other durations of stimulation are possible and can, for example, be experimentally determined.

The administration of the optical first stimuli 145 takes place via the individual segments 141 to 144 of the transmission eyeglasses 11 with a delay in time between the individual segments 141 to 144 in accordance with the embodiment shown in FIG. 13. For example, the start of the stimuli 145 applied following one another in time and applied by different segments 141 to 144 can be delayed by a time τ.

In the case of N stimulation elements and/or segments, which are used for the stimulation, the delay in time τ between two respective stimuli 145 following one another can, for example lie in the range of an N-th of the period $T_{stim}=1/f_{stim}$. In the embodiment shown in FIG. 13 (N=4), the delay in time τ thus corresponds to $T_{stim}/4$. From the provision that the delay in time τ between respective stimuli 145 following one another respectively amounts to $T_{stim}/N$ can be deviated from to a certain degree. For example, it can be deviated from the value $T_{stim}/N$ for the delay in time τ by up to ±10%, ±20% or ±30%. For such deviations stimulation results were still achieved, this means that a desynchronized effect could still be observed.

The square waveform of the individual pulse 145 illustrated in FIG. 13 represents an ideal shape. Depending on the quality of the electronic generating the individual pulses 145 and of the transmission glass lenses 122 a deviation from the ideal square wave shape is also present. However,—e.g. depending on the basic illness of the patient, as well as individual psycho-physical conditions, e.g. sensitivity to blending—stimuli with less sharp edges, e.g. smoother extents can also be used.

Figure 14:
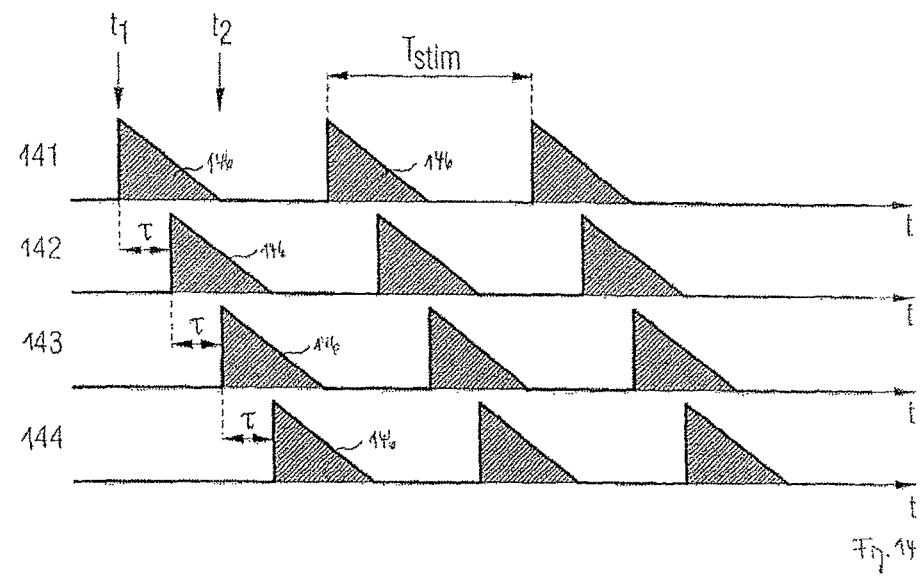
Figure 15:
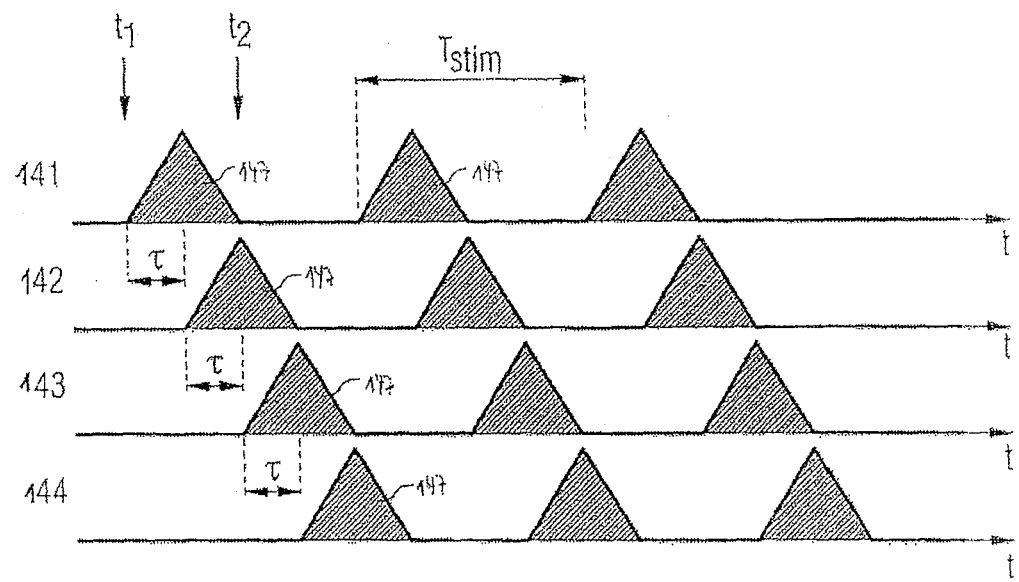
Figure 16:
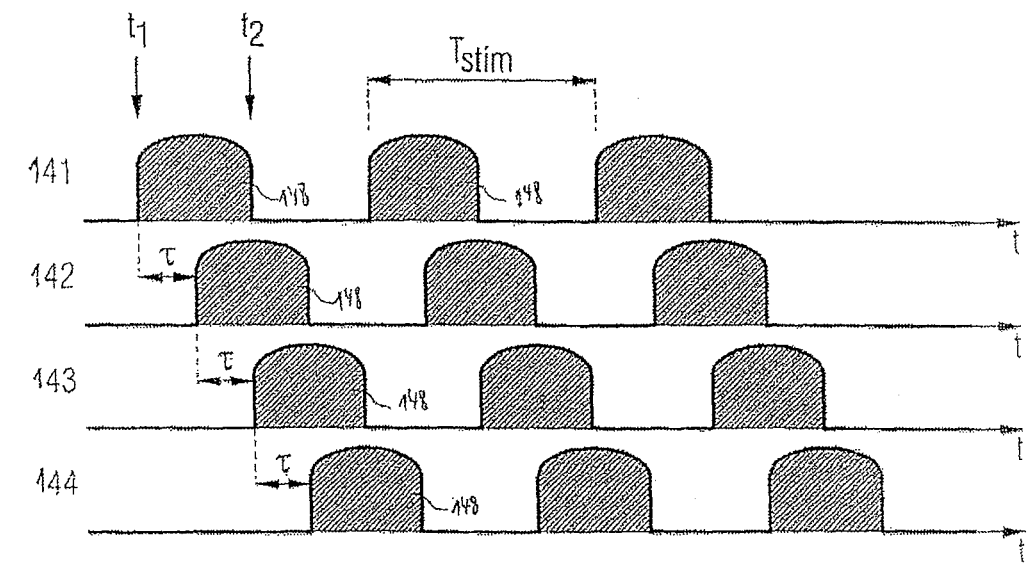

Instead of square wave shaped stimuli 145 the control unit 10 can, for example, generate optical first stimuli of different design, as are illustrated by way of example in FIGS. 14 to 16. Triangular-shaped first optical stimuli 146 are shown in FIG. 14. At the point in time $t_1$, for example, a switch is made to the minimum transition and the transmission continuously increases to the maximum value up until the point in time $t_2$. It can alternatively be provided that the transmission is at a maximum at the start of the stimulus 146 and subsequently decreases to the minimum value.

Triangular optical first stimuli 147 having an increasing edge and a decreasing edge are shown in FIG. 15. Starting at the point in time $t_1$ the transmission is, for example increased and on achieving a maximum is reduced again until the point in time $t_2$.

It can moreover be provided that the increasing and decreasing edges of the stimuli are "rounded" (e.g. exponentially). This is shown in FIG. 16 with reference to rounded square wave shaped optical first stimuli 148. Furthermore, the stimuli can also be displaced into a simple sinusoidal shape.

The above described signal shapes and their parameters are to be understood only by way of example. It is by all means possible to deviate from the above provided signal shapes and their parameters.

It can be deviated from the strongly periodic stimulation pattern shown in FIGS. 13 to 16 in different ways and manners. For example, the delay in time τ between two stimuli 145, 146, 147 and 148 following one another does not necessarily have to be of equal size. It can be provided that the distance in time between the individual stimuli 145, 146, 147 and/or 148 is selected in a different manner. The delay times can moreover also be varied during the treatment of a patient. The delay times can also be adjusted with regard to the physiological signal running times.

Furthermore, pauses can be provided during the application of the stimuli 145, 146, 147 and/or 148 during which pauses no stimulation takes place. The pauses can be selected of arbitrary length and, in particular amount to an integer multiple of the period $T_{stim}$. The pauses can be maintained after an arbitrary number of stimulations. For example, a stimulation can be carried out during N periods of the length $T_{stim}$ following one another and a stimulation pause can subsequently be maintained during M periods of the length $T_{stim}$, wherein N and M are small integers, e.g. in the range of 1 to 15. This scheme can either be periodically continued or be modified stochastically and/or deterministically, e.g. chaotically.

A further possibility for deviating from the strongly periodic stimulation pattern shown in FIGS. 13 to 16 exists therein in varying the separation in time between stimuli 145, 146, 147 and/or 148 following one another per segment 141 to 144 stochastically or deterministically or mixed stochastic-deterministically.

Furthermore, the sequence in which the segments 141 to 144 apply the stimuli 145, 146, 147, 148 can be varied per period $T_{stim}$ (or in different time steps). This variation can take place stochastically or deterministically or mixed stochastic-deterministically.

Moreover, the same sequence of the segments 141 to 144 can be selected within N associated stimulation periods which is, however, varied between different blocks within N stimulation periods for the stimulation pattern, in which the N stimulation periods are followed by M periods of pause and are repeated as a cycle. This variation can place stochastically or deterministically or mixed stochastic-deterministically.

Furthermore, only a specific number of the segments 141 to 144 can be used for the stimulation and the segments involved in the stimulation can be varied in each time interval per period $T_{stim}$ (or in a different time interval). Also this variation can take place stochastically or deterministically or mixed stochastic-deterministically.

Instead of the pulse-shaped and time-displaced stimuli 145 to 148 shown in FIGS. 13 to 16 also optical stimuli having other signal shapes can be used. For example, each of the segments 141 to 144 can generate a sinusoidal signal (e.g. a continuous sinusoidal signal) in which the phases of the sinusoidal signal generated by the different segments 141 to 144 are displaceable with regard to one another. The mean frequency of the sinusoidal signal can in this respect be the same. The phase displacement between the individual sinusoidal signal can either be predetermined, e.g. the phase displacement between two of N respective stimulation signals amounts to $2\pi/N$ which corresponds to a time shift of $T_{stim}/N$, or the phase displacement can be varied e.g. chaotically and/or stochastically. Moreover, the optical stimuli can have different polarities. In the case of a sinusoidal signal as an optical stimulus, for example, the sinusoidal signal of two segments can be applied at the same time is, however, applied with inverse polarity (which corresponds to a phase shift of π).

Furthermore, it is possible that each of the segments 141 to 144 applies a sinusoidal signal with a respectively different frequency. For example, one of the segments can apply a sinusoidal signal with 5 Hz and the other three segments apply sinusoidal signals with 4 Hz, 3 Hz and/or 2 Hz (this means that in the case of transmission eyeglasses the transmission of the respective segments 141 to 144 changes with the corresponding frequency). Instead of sinusoidal signals also other (oscillating) signal shapes, e.g. square wave signals, with the corresponding base frequency can be used. The signals need not be applied displaced in time, but the segments 141 to 144 can rather also simultaneously generate the optical stimuli. The optical stimuli can be applied continuously over a longer period of time, however, also pauses can be maintained during the application.

The application of optical stimuli with different frequencies does not necessarily lead to a quick reset of the phase of the neuronal activity in the respective stimulated sub-population, however, the sub-population stimulated through the respective stimulation with these signals has a respective phase forced thereupon for a certain period of time dependent on stimulation frequency. This finally also leads to a desynchronization of the overall neuron population.

Figure 17:
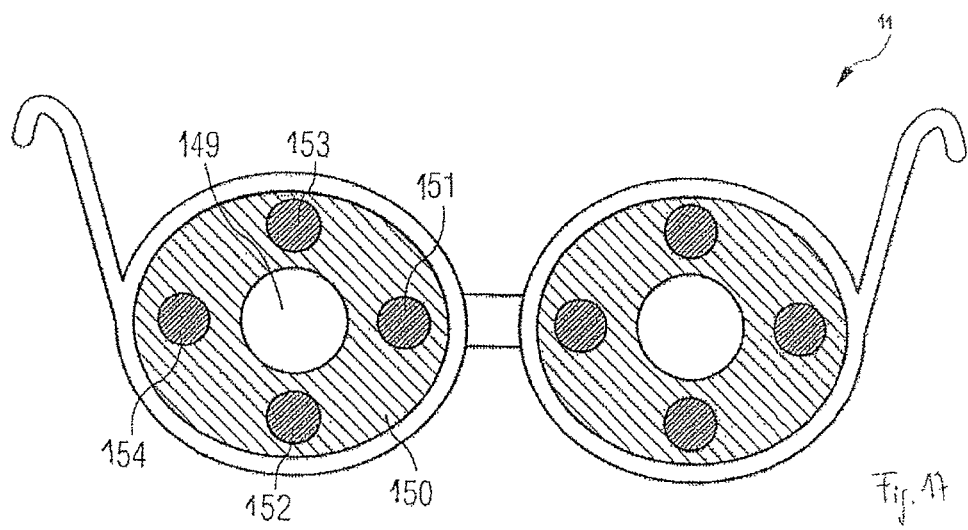
FIGS. 17 and 18 schematic illustrations of light eyeglasses.

Partially transparent light eyeglasses 11 are schematically illustrated in FIG. 17 as a further embodiment of the first stimulation unit. For the partially transparent light eyeglasses 11 no glass is used whose transmission can be varied. Rather more only a part 149 of each eyeglass is permeable while the remaining part 150 of the eyeglasses is non-transparent. A light source is arranged at at least one position per eyeglass. The light source can, for example, be a light emitting diode or a fiber glass cable which e.g. guides the light of a light emitting diode or of a different light medium arranged at a different position to this point in the glass lens. The light eyeglasses 11 illustrated in FIG. 17 have four light sources 151, 152, 153 and 154 per glass lens. The light eyeglasses 11 can, however, also have any different number of light sources which can be arranged in an arbitrary geometry. Moreover, the transparent part 149 can also be of a design different from that illustrated in FIG. 17.

The patient can only look through the transparent part 149 of the glass lenses. The patient is forced to hold his eye relative to the eyeglass at a constant position when this part is small in comparison to the overall glass lens. The light sources 151 to 154 only stimulate the retina of the patient while they do not visually stimulate an observer on the other side of the eyeglasses. The different light sources 151 to 154, for example, stimulate certain part regions of the retina of the patient. The intermediate space between the boundary of the eyeglasses and the face can be closed off light-tight (not illustrated).

Figure 18:
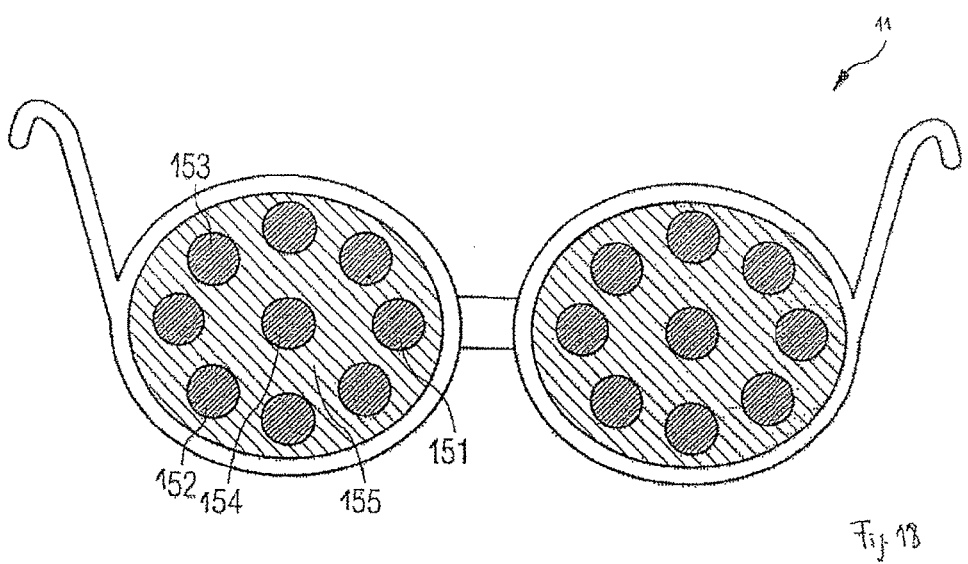

Non-permeable light eyeglasses 11 are schematically illustrated in FIG. 18 as a further embodiment of the stimulation unit. The glass lens 155 is completely non-transparent for the non-transparent light eyeglasses 11. A light source is attached at at least one position of each pair of light glass lenses 155. The light sources can be designed identical to the partially transparent light eyeglasses, thus e.g. as light-emitting diodes or fiber glass cables. In the example shown in FIG. 18 each of the glass lenses has nine light sources. Four of these light sources are provided with the reference numerals 151 to 154. The light eyeglasses 11 can, however, also have any other number of light sources which can be arranged in an arbitrary manner.

The patient cannot look through the glass lenses, but is rather exclusively visually stimulated through the light sources. The light sources stimulate—like with the partially permeable light eyeglasses—only the retina of the patient. The different light sources stimulate certain part regions of the retina of the patient. The intermediate space between the boundary of the eyeglasses and the face can be sealed off light-tight (not illustrated).

The non-permeable light eyeglasses 11 can include a fixation target which the patient can comfortably fixate (e.g. without blending effects). It is prevented that the patient follows the different illuminating light sources with eye movements through the instruction to fixate on the fixation target during the therapy. In the latter case, in particular the central part of the retina, the fovea, would be stimulated while the different part of the retina could be stimulated with a fixation target.

Figure 19:
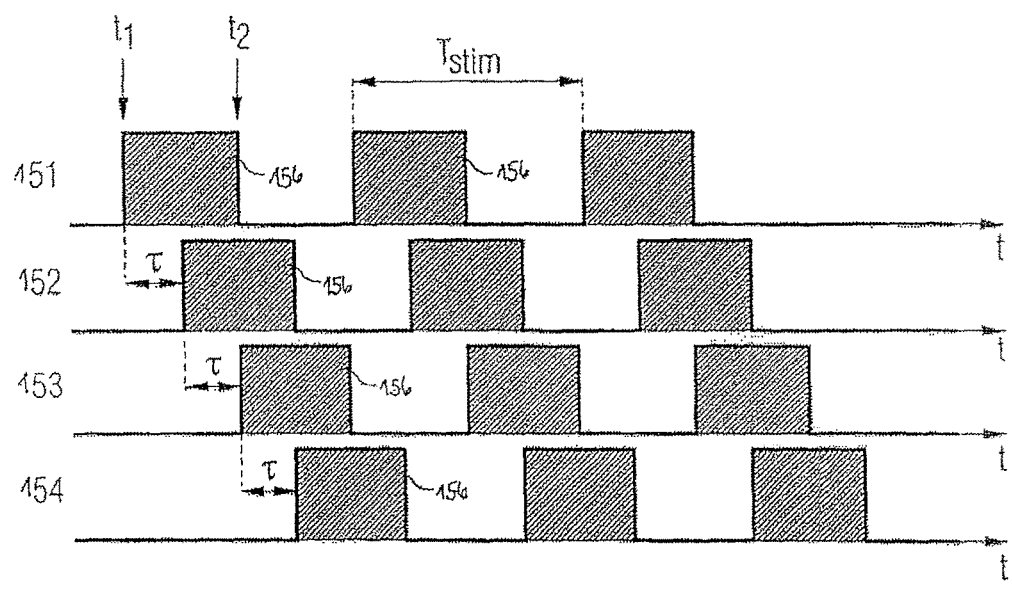
FIG. 19 a schematic illustration of specific optical stimuli generated by means of a light eyeglasses.

A stimulation method which can, for example, be carried out with the light eyeglasses 11 shown in FIGS. 17 and 18 is schematically illustrated in FIG. 19. The optical first stimuli 156 applied by the light sources 151 to 154 of the light eyeglasses 11 are applied beneath one another against the time t in FIG. 19.

The method illustrated in FIG. 19 substantially corresponds to the method shown in FIG. 13 for the transmission eyeglasses. In the method illustrated in FIG. 19 each of the light sources 151 to 154 periodically applies the stimuli 156. The frequency $f_{stim}=1/T_{stim}$ with which the stimulus 156 can be repeated per light source 151 to 154 can lie in the range of 1 to 30 Hz and, in particular in the range of 5 to 20 Hz, can, however, also take on smaller or larger values.

The stimulation method is only illustrated for four light sources 151 to 154 in FIG. 19 for the simplified illustration thereof. This method can, however, be extended in a corresponding manner to an arbitrary number of light sources.

On the generation of the stimuli 156 by means of light sources the concerned light sources are typically switched on at a point in time $t_1$ and are switched off at the point in time $t_2$. The maximum amplitude (brightness) of the individual light stimuli typically lies in a range of 1 to 20 cd/m$^2$.

Also smaller brightness values can be used during the stimulation, this means during the time span between $t_1$ and $t_2$.

All designs described in connection with FIGS. 13 to 16 can also be transferred in a corresponding manner to the stimulation by means of the light eyeglasses 11 shown in FIGS. 17 and 18.

Stimulation Units for the Generation of Specific Acoustic Stimuli:

The embodiments of the non-invasive first stimulation unit 11 for the generation of acoustic first stimuli will be described in the following. Such stimulation units can also be found in the German patent application no. 10 2008 015 259.5 having the title "Apparatus and method for auditory stimulation" which was filed at the German Patent and Trademark Office on Mar. 20, 2008. The overall content of disclosure of the German patent application no. 10 2008 015 0259.5 is hereby incorporated into the disclosure of the patent application.

In the following reference will only be made to the generation of acoustic first stimuli. It is naturally understood that these specific first stimuli are applied in combination with the non-specific second stimuli, like they are described above e.g. in accordance with FIGS. 1 to 5.

Figure 20:
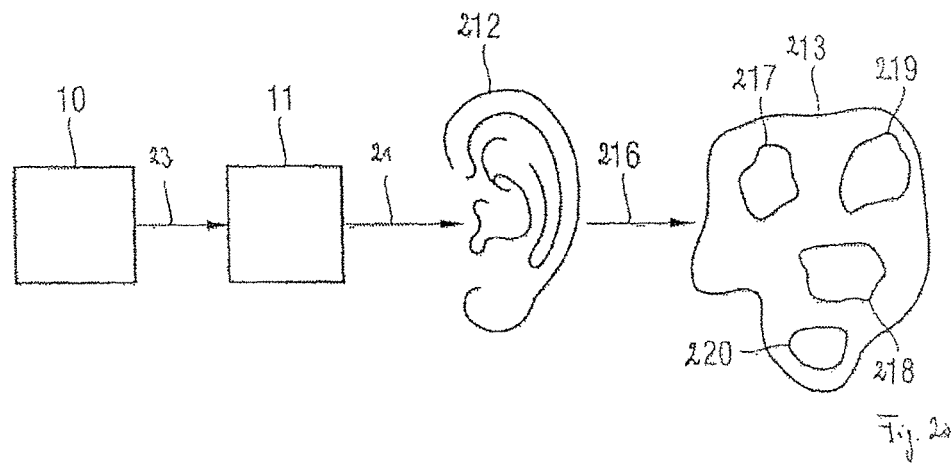
FIG. 20 a schematic illustration of a stimulation unit for the generation and application of specific acoustic stimuli in accordance with an embodiment.

FIG. 20 schematically shows an embodiment of the first stimulation unit 11 for the generation of acoustic first stimuli 21. The first stimulation unit 11 is controlled by the control unit 10 with control signals 23. An ear 212 of a patient as well as the auditory cortex 213 in the brain of the patient is moreover schematically illustrated in FIG. 20.

The frequency spectrum of the acoustic first stimuli 21 can completely lie or partially lie in the range audible for the human. The acoustic first stimuli 21 are received by the patient via one or both ears 212 and are guided to the neuron population in the brain via one or more acoustic nerves 216. The acoustic first stimuli 21 are designed such that they stimulate the neuron population in the auditory cortex 213. A first frequency $f_1$ and a second frequency $f_2$ are at least present in the frequency spectrum of the acoustic first stimuli 21. The acoustic first stimuli 21 can moreover also include further frequencies or mixed frequencies, in the embodiment shown in FIG. 20 these are a third frequency $f_3$ and a fourth frequency $f_4$.

The acoustic first stimuli 21 generated by the first stimulation unit 11 are transferred into nerve impulses in the inner ear and are guided to the auditory cortex 213 via the acoustic nerve 216. A certain part of the order auditory cortex 213 is activated on the acoustic stimulation of the inner ear with a certain frequency through the tonotopic arrangement of the auditory cortex 213. The tonotopic arrangement of the auditory cortex is, e.g. described in the following articles: "Tonotopic organization of the human auditory cortex as detected by BOLD-FMRI" by D. Bilecen, K. Scheffler, N. Schmid, K. Tschopp and J. Seelig (published in Hearing Reasearch 126, 1998, pages 19 to 27), "Representation of lateralization and tonotopy in primary versus secondary human auditory cortex" by D. R. M. Langers, W. H. Backes and P. van Dijk (published in NeuroImage 34, 2007, pages 264 to 273) and "Reorganization of auditory cortex in tinnitus" by W. Mühlnickel, T. Elbert, E. Taub and H. Flor (published in Proc. Natl. Acad. Sci. USA 95, 1998, pages 10340 to 10343).

The acoustic first stimuli 21 are designed so that a neuron population of the auditory cortex 213 having a pathological synchronous and oscillatory activity can be stimulated therewith in the example in accordance with FIG. 20. This neuron population can be divided before the start of the stimulation, at least in thought, for the different sub-populations, amongst other things, into the sub-populations 217, 218, 219 and 220 shown in FIG. 20. Before the start of the stimulation the neurons of all sub-populations 217 to 220 fire substantially synchronously and on average with the same pathological frequency. Due to the tonotopic organization of the auditory cortex 213 the first sub-population 217 is stimulated by means of the first frequency $f_1$, the second sub-population 218 is stimulated by means of the second frequency $f_2$, the third sub-population 219 is stimulated by means of third frequency $f_3$, and the fourth sub-population 220 is stimulated by means of the fourth frequency $f_4$. The stimulation with the acoustic first stimuli 21 brings about a reset into the respective sub-populations 217 to 220, a so-called setting back, of the phase of the neuronal activity of the stimulated neurons. The phase of the stimulated neurons is set to a certain phase value, e.g. of 0° through the reset independent of the actual phase value. Thus, the phase of the neuronal activity of the pathological sub-populations 217 to 220 is controlled by means of a targeted stimulation Due to the tonotopic arrangement of the auditory cortex 213 as well as of the plurality of frequencies $f_1$ to $f_4$, which are included in the acoustic first stimuli 21, it is possible to stimulate the pathological neuron population at different positions 217 to 220 in a targeted manner. This enables a reset of the phase of the neuronal activity of the pathological neuron population at the different stimulation points 217 to 220 to different points in time in that the Frequencies $f_1$ to $f_4$ are applied at different points in time. This thereby results in the pathological neuron population whose neurons were previously active synchronously and active at the same frequency and phase to split up into the sub-populations 217 to 220. The neurons are furthermore synchronous and also furthermore fire on average with the same pathological frequency within each of the sub-populations 217 to 220, however, each of the sub-populations 217 to 220 has the phase with regard to its neuronal activity which was forced thereupon through the stimulation stimulus with the associated frequency $f_1$ to $f_4$.

The state generated through the stimulation with at least two sub-populations is instable due to the pathological interaction between the neurons and the overall neuron population approximates quickly to a state of complete desynchronization in which the neurons fire in an uncorrelated manner. The desired state, this means the state of complete desynchronization, is thus not immediately present following the application of the acoustic first stimulation 21, but is typically set within a few periods or even in less than a period of the pathological activity.

In order to focally stimulate the auditory cortex 213 at different positions, e.g. the positions shown in FIG. 20 and/or the sub-populations 217 to 220 pure tones of the associated frequency $f_1$, $f_2$, $f_3$ and $f_4$ (with suitable shielding for the avoidance of clicking noises) must be administered. Different parts of the brain are stimulated through the simultaneous administration of the associated different pure tones $f_1$ to $f_4$, this means through the super-position of different sinusoidal oscillations as a result of the tonotopic arrangement of the auditory cortex 213. If the four different positions 217 to 220 should e.g. be stimulated at different times, the four different frequencies $f_1$ to $f_4$ are applied at the respective times. This is shown by way of example in FIG. 21. In this example sinusoidal oscillations having the frequencies $f_1=1000$ Hz, $f_2=800$ Hz, $f_3=600$ Hz and $f_4=400$ Hz are successively applied and applied in pulse-shape, which leads to a successive focal stimulation at the four different positions 217 to 220 of the auditory cortex 213. The strength of the stimulation generated through the respective sinusoidal oscillation of the respective area in the auditory cortex 213 corresponds to the amplitude of the respective sinusoidal oscillation.

Figure 21:
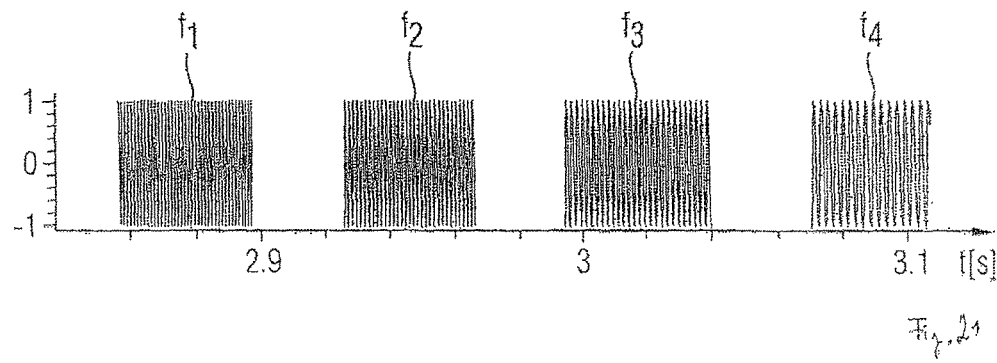
FIG. 21 an illustration of sinusoidal oscillations with different frequencies.
Figure 22:
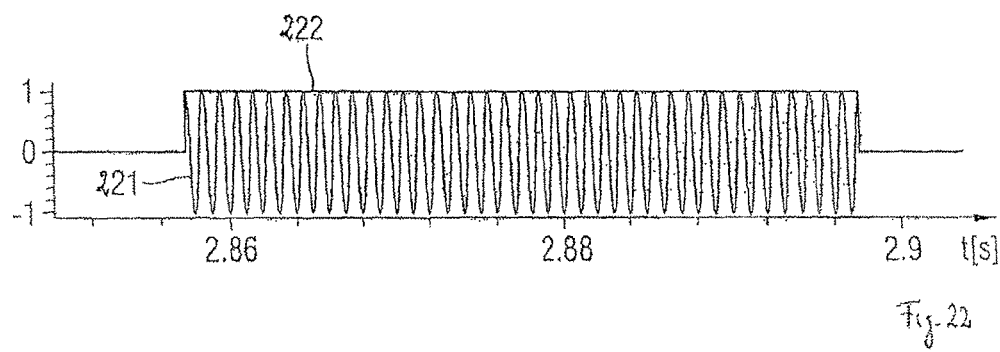
FIG. 22 an illustration of a sinusoidal oscillation amplitude modulated with a square wave function.

The generation of the pulse-shaped sinusoidal oscillation shown in FIG. 21 is illustrated by way of example in FIG. 22. There a sinusoidal oscillation 221 is multiplied with a square wave function 222 which can take on the values 0 or 1. At the points in time at which the square wave function 222 has the value 0 the associated stimulus is switched off and the stimulus is switched on during the time in which the square wave function 222 is equal to 1.

Instead of the square wave function 222 the sinusoidal oscillation 221 can be multiplied with any arbitrary different function. As a result this multiplication corresponds to an amplitude modulation of the sinusoidal oscillation 221. In order to avoid clicking sounds due to a sharp start and end of the tone a smoother extent can be selected rather than the square wave function 222, e.g. through multiplication of the sinusoidal oscillation 221 with a sinusoidal half oscillation of a suitable duration, e.g. the duration of a stimulus.

Also oscillating signals with a different signal shape, such as e.g. square wave signals, which oscillate with the corresponding base frequency can be utilized for the generation of the acoustic first stimuli 21 instead of the previously described sinusoidal oscillations.

As long as a few focal stimuli which activate larger parts of the auditory cortex 213 should be carried out rather than a focal stimulation, then mixed frequencies are applied, for example in pulse-shape rather than individual frequencies. All of the parts of the auditory cortex 213 are stimulated which are stimulated due to the frequencies between $f^{unten}$ and $f^{oben}$ by the tonotopic arrangement by means of a frequency mixture in the boundaries between a lower frequency $f^{unten}$ and a higher frequency $f^{oben}$. Should e.g. four different larger areas of the auditory cortex 213 be stimulated at different points in time, then the four associated frequency mixtures with the boundaries $f_j^{unten}$ and $f_j^{oben}$ (j=1, 2, 3, 4) are applied at the desired times.

Figure 23:
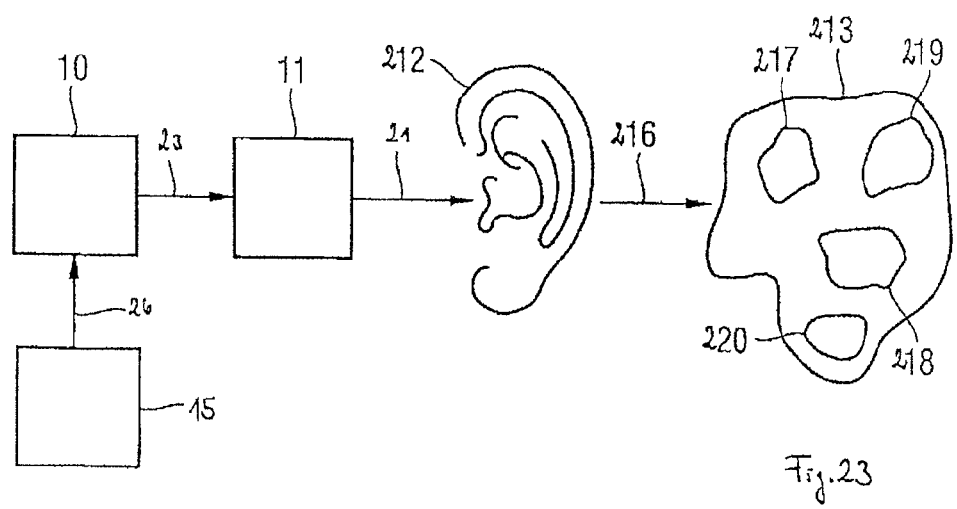
FIG. 23 a schematic illustration of a stimulation unit for the generation and application of specific acoustic stimuli in accordance with a further embodiment.

The first stimulation unit 11 can, for example be operated in a so-called "open loop"-mode in which the control unit 10 controls the stimulation unit 11 such that this generates the predetermined acoustic first stimuli 21 during a certain stimulation time (e.g. during several hours). Furthermore, the first stimulation unit 11 can be further developed together with the control unit 10 also to a "closed loop"-system as schematically illustrated in FIG. 23. In this embodiment a measurement unit 15 is additionally provided which provides measurement signals recorded at the patient and guides these to the control unit 10. The measurement unit 15 can be non-invasive sensors or invasive sensors (cf. the above description in connection with FIG. 3).

Different designs are plausible with regard to the cooperation of the control unit 10 with the measurement unit 15.

For example—as described above—a change can be made between the first mode of operation, the learning phase, and the second mode of operation, the actual stimulation phase on the basis of the measurement signals. Parameters of the acoustic first stimuli 21, such as for example, the amplitude of the respective sinusoidal oscillation or the pauses between stimulation sequences can moreover be set by the control unit on the basis of the extent of the pathological features.

It can furthermore be provided that the measurement signals recorded by the measurement unit 15 are directly converted or are converted possibly following one or more processing steps into acoustic first stimuli 21 and are applied by the first stimulation unit 11. For example, the measurement signals can be amplified and possibly introduced following a mathematical calculation (e.g. after mixing the measurement signals) with a time delay and linear and/or non-linear processing steps as control signals 23 into the control input of the first stimulation unit 11. The calculation mode is in this respect selected so that the pathological neuronal activity is counteracted and the acoustic first stimuli 21 likewise disappear with reducing pathological neuronal activity or are at least significantly reduced in their strength.

Figure 24:
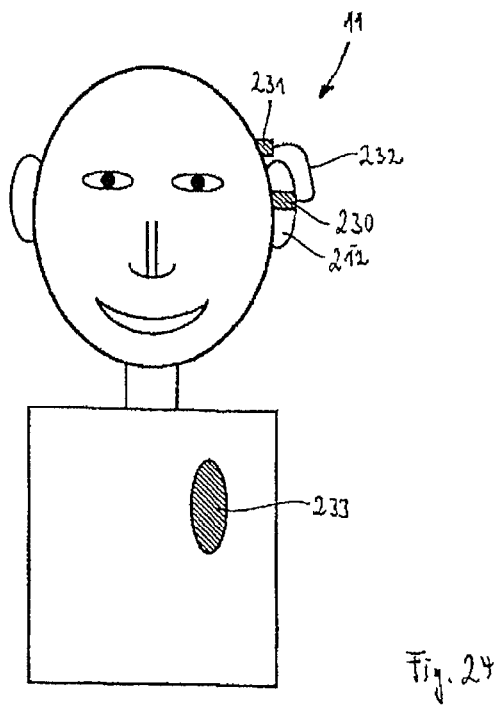
FIG. 24 a schematic illustration of a stimulation unit for the generation and application of specific acoustic stimuli in accordance with a further embodiment.

A design of the first stimulation unit 11 is schematically illustrated in FIG. 24 which design uses an acoustic generator (loudspeaker) which is introduced into an ear plug 230. The ear plug 230 is introduced into the outer auditory canal channel of an ear of the patient 212 and is attached there with or without the aid of a holder and/or a different suitable mechanical aid at the ear 212. The control unit 10 which controls the acoustic generator as well as a battery or a storage battery for the supply of current for the electrical components can be installed in one or more separate units 231. The unit 231 can be connected to the ear plug 230 by means of a mechanical support, e.g. a holder. A connection cable 232 connects the ear plug 230 to the control unit 10 and/or to the battery.

Alternatively also a headphone can be used instead of the ear plug 230 which headphone includes the control unit 10 and the battery. The apparatus shown in FIG. 24 can be switched on by the patient by means of an operating unit (e.g. switch-on button and/or rotary switch) which is either arranged at the unit 231 or directly at the ear plug 230. The maximum stimulation strength can be, for example, set with the rotary switch. A control medium 233 can be provided in addition to the previously mentioned components which control medium 233 is, for example, telemetrically connected to the control unit 10 (e.g. via radio communication) or is connected to the control unit 10 via connection cable. In the case of a connection via a cable, plug connections can be used for connecting and disconnecting.

Moreover, also a further control medium (not illustrated) can be provided which is to be operated e.g. by the doctor and which is connected to the control unit 10 by telemetry or via a connection cable. In the case of a connection via a cable, plug connectors can be used for connecting and/or disconnecting.

Figure 25:
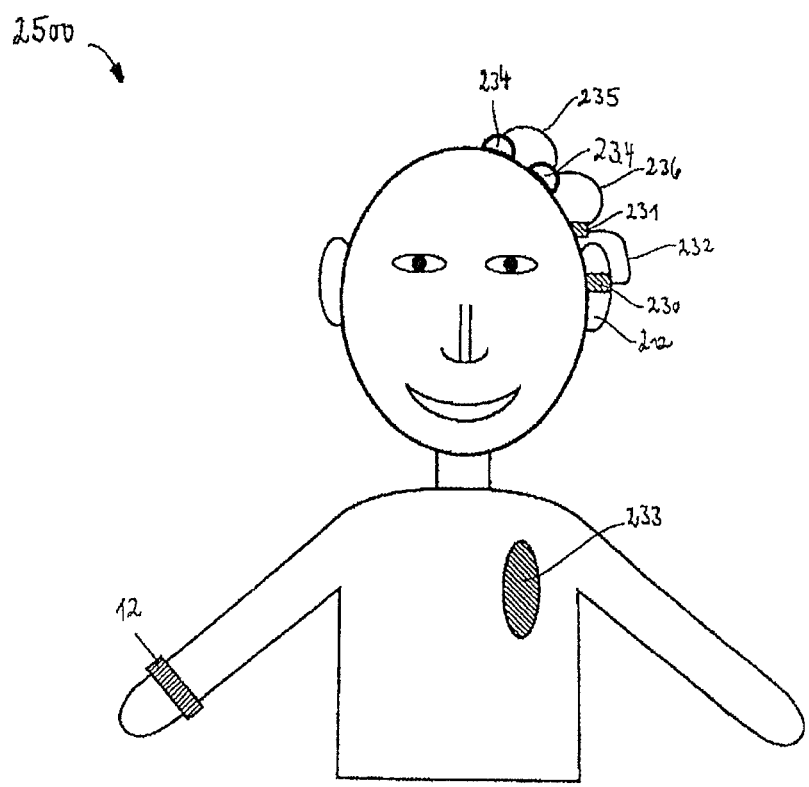
FIG. 25 a schematic illustration during the operation of an apparatus for the conditioned desynchronized non-invasive stimulation in accordance with a further embodiment.

FIG. 25 schematically shows an apparatus 2500 which has a first stimulation unit 11 adapted, like the one shown in FIG. 24, a measurement unit composed of EEG electrodes 234, as well as a second stimulation unit 12 for the application of the second non-specific stimuli. The EEG electrodes 234 are epicutaneous, this means that they are attached at the skin of the patient and are connected to the control unit 10 via connection cables 235, 236. The control unit 10 uses the measurement signals provided by the EEG electrodes, e.g. for the setting of the mode of operation. The control unit 10 can also amplify the potential difference measured by means of the EEG electrodes 234 and can use this signal following an optional linear or non-linear calculation for controlling the acoustic generator in ear plug 230. The EEG-electrodes 234 can also be wirelessly connected to the control unit 10, this means that they are connected to the control unit 10 by telemetry as an alternative to the connection cables 235, 236. This has the advantage that the patient is not hindered by connection cables and can e.g. not get stuck at barriers. The apparatus 2500 has the conditioning clock shown in FIGS. 4A and 4B as a second stimulation unit 12. The second non-specific stimuli can alternatively also be generated by means of a stimulation unit 12 of different design.

Figure 26:
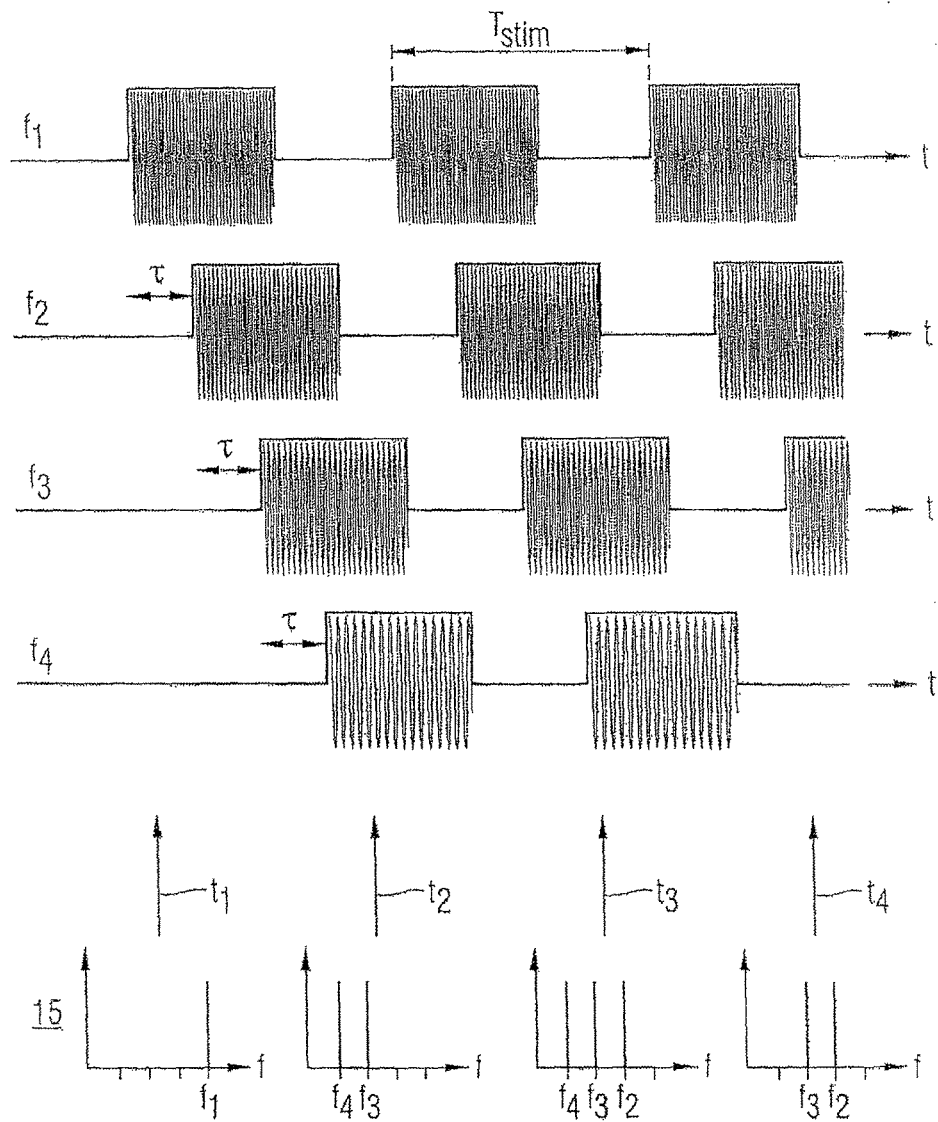

It shall be explained in the following by way of example how a desynchronization of the overall neuron population can be achieved through a time shifted reset of the phase of the neuronal activity of sub-populations of a pathological synchronous and oscillatory neuron population on the basis of the above-described mentioned four frequencies $f_1$ to $f_4$. The four frequencies $f_1$ to $f_4$ are to be understood merely by way of example, this means that an arbitrary number of frequencies or of frequency mixtures can be used for the purpose of stimulation. The frequencies $f_1$ to $f_4$ are selected so that specific regions 217 to 220 of the auditory cortex 213 can be respectively stimulated. This enables the above-described splitting up of a pathological neuron population into sub-populations 217 to 220. The frequencies $f_1$ to $f_4$ can be applied e.g. shifted in time, so that the sub-populations 217 to 220 have the different phases after the stimulation. A stimulation method suitable for the above-described purpose is schematically illustrated in FIG. 26. Four sinusoidal oscillations with the frequencies $f_1$, $f_2$, $f_3$, $f_4$ are applied against time t beneath one another in the upper four lines in FIG. 26. The acoustic first stimuli 21 are formed from the illustrated sinusoidal oscillations. For the generation of pulse-shaped sinusoidal oscillations, the four sinusoidal oscillations have been multiplied with square wave functions. Also smoother functions, such as e.g. sinusoidal half oscillations, can be used instead of the square wave function in order to avoid clicking sounds as was described above. Each sinusoidal pulse repeats itself periodically with a frequency $f_{stim}$. The frequency $f_{stim}=1/T_{stim}$ can lie in the range of 1 to 30 Hz and, in particular in the range of 5 to 20 Hz can, however, also take on smaller or larger values. Such sequences of pulse-shaped sinusoidal oscillation are suitable, when they are applied as an acoustic first stimuli 21, to reset the neuronal phase of the respective stimulated pathological neuron sub-population 217, 218, 219 and/or 220. The phase reset in this respect does not necessarily result already after one or a few pulses, but a certain number of the sinusoidal pulses shown in FIG. 26 may rather be required in order to reset the neuronal phase of the respective sub-population 217, 218, 219 and/or 220.

The frequency $f_{stim}$ can, for example, lie in the range of the mean frequency of the pathological rhythmic activity of the target network. For neurological and psychiatric illnesses the mean frequency typically lies in the range of 1 to 30 Hz can, however, also lie outside of this range. For tinnitus an excessive synchronous neuronal activity is found e.g. in the frequency range of 1.5 to 4 Hz. In this respect it should be noted that the frequency with which the pathological neurons synchronously fire is typically not constant, but can rather have variations and can furthermore show individual deviations for each patient.

For example, the mean peak frequency of the pathological rhythmic activity of the patient can be determined for determining the frequency $f_{stim}$. This peak frequency can then be used with a stimulation frequency $f_{stim}$ or can also be varied, for example, in a range of $f_{stim}$–3 Hz to $f_{stim}$+3 Hz. However, a frequency $f_{stim}$ in the range of 1 to 3 Hz can alternatively be selected without a prior measurement and this can, for example be varied during a stimulation until the frequency $f_{stim}$ is found with which the best stimulation results can be achieved. A literature value known for the respective illness can be utilized for the stimulation of frequency $f_{stim}$ as a further alternative. This value can possibly still be varied up until, for example, ideal stimulation results can be achieved.

The duration of a sinusoidal pulse, this means the time span in which the square wave function takes on the value 1 in the present design can, for example amount to $T_{stim}/2$. In this case the time span during which the respective frequency contributes to the stimulation and the subsequent stimulation pause are of equal length. However, it is also possible to select different durations of stimulation, for example, in the range of $T_{stim}/2-T_{stim}/10$ up until $T_{stim}/2+T_{stim}/10$. The duration of stimulation can, for example, be determined experimentally.

In accordance with the embodiment shown in FIG. 26 the administration of the individual frequencies $f_1$ to $f_4$ takes place with a time delay between the individual frequencies $f_1$ to $f_4$. For example, the start of pulses following one another in time and having different frequencies can be displaced by a time τ.

In the case of N frequencies, which are used for the stimulation, the delay in time τ between two pulses respectively following one another can, for example, lie in the range of an N-th of the period $T_{stim}=1/f_{stim}$. In the embodiment shown in FIG. 26 (N=4) the delay in time T correspondingly amounts to $T_{stim}/4$. It can be deviated from the provision that the delay in time π between two respective subsequent sinusoidal oscillation pulses amounts to $T_{stim}/N$ to a certain degree. For example, it can be deviated from the value $T_{stim}/N$ from the delay in time τ by up to ±5%, ±10%, ±20% or ±30%. Stimulation results were still achieved for such deviations, this means that a desynchronized effect could still be observed.

The acoustic first stimulus 21 is formed by superposition from the periodic sinusoidal oscillation pulses with the frequencies $f_1$ to $f_4$. The individual sinusoidal oscillation pulses can in this respect be combined with one another, for example linearly or non-linearly. This means that the sinusoidal oscillations of the individual frequencies $f_1$ to $f_4$ do not necessarily have to be combined with the same amplitudes to the acoustic first stimulus 21. The frequency spectrum of the acoustic first stimulus 21 is illustrated by way of example in the lowest line of FIG. 26 at the four points in time $t_1$, $t_2$, $t_3$ and $t_4$. The frequency spectra shown there, in particular the height and the shape of the frequency peaks, are to be understood merely by way of example and can also have completely different shapes. The following statements can be extracted from the the illustrated frequency spectra in detail: At the point in time $t_1$ merely the frequency $f_1$ is present in the acoustic first stimulus 21. At the point in time $t_2$, the frequencies $f_3$ as well as $f_4$ are present, at the point in time $t_3$ the frequencies $f_2$ to $f_4$ are present and at the point in time $t_4$ the frequencies $f_2$ and $f_3$ are present.

In accordance with an alternative embodiment four frequency mixtures with the boundaries $f_j^{unten}$ and $f_j^{oben}$ (j=1, 2, 3, 4) are used instead of the frequencies $f_1$ to $f_4$. In a frequency mixture j can be any arbitrary number of frequencies in the range of $f_j^{unten}$ to $f_j^{oben}$.

In accordance with a further alternative embodiment other functions are used for the amplitude modulations and the sinusoidal oscillation instead of the square wave function, e.g. sinusoidal half waves whose frequency is smaller than $f_1$ to $f_4$. It is moreover, for example, plausible that triangular shaped pulses are used as modulation functions. Such a pulse can have a jump-like onset (from 0 to 1) and then a decrease to 0, wherein the decrease can, for example be provided by a linear or exponential function. Through the modulation function the shape of the surrounding of the individual pulses is finally determined.

Figure 27:
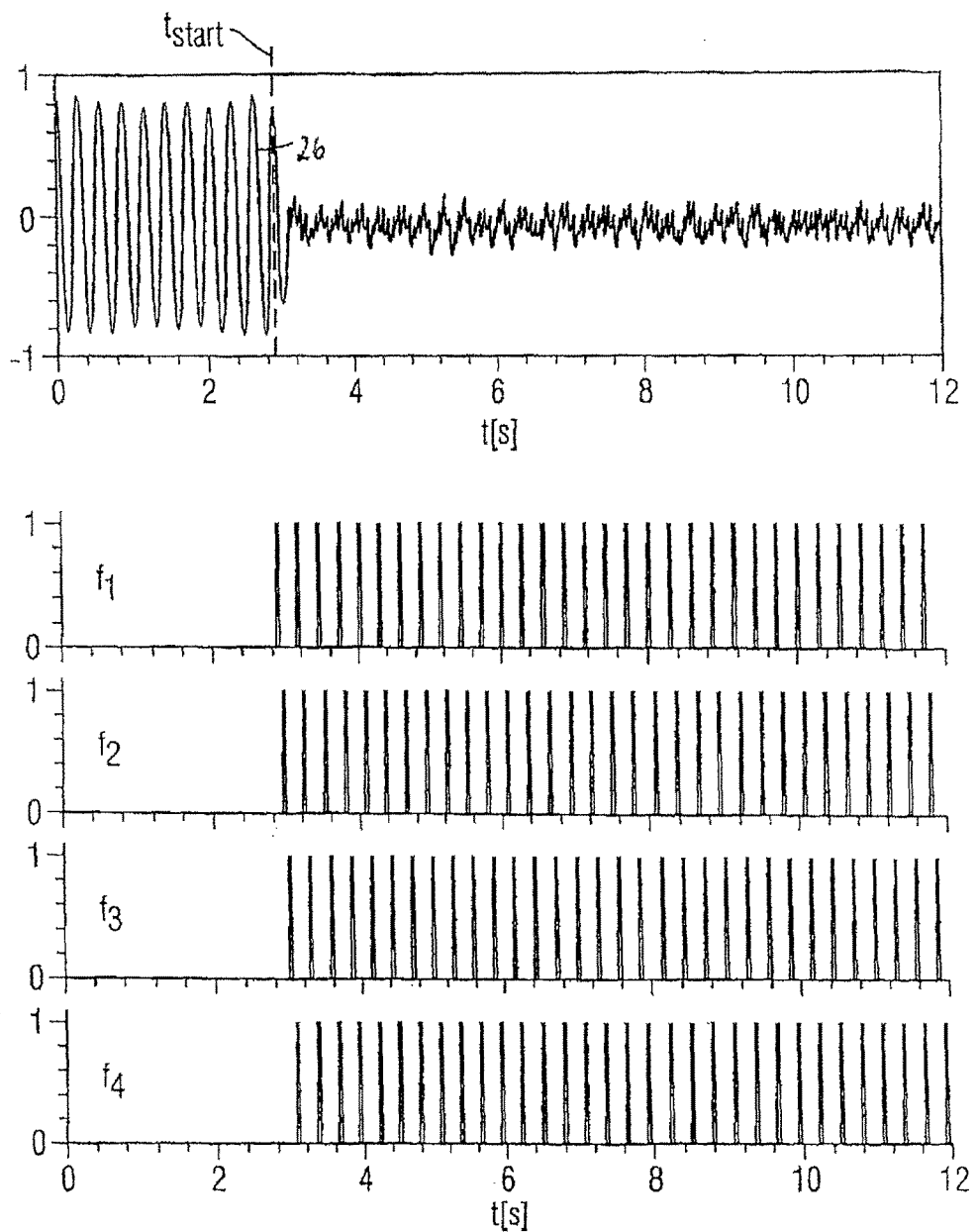

The stimulation already shown in FIG. 26 is illustrated over a longer period of time in FIG. 27. The individual sinusoidal oscillations with the frequencies $f_1$=1000 Hz, $f_2$=800 Hz, $f_3$=600 Hz and $f_4$=400 Hz are not shown in FIG. 27, but rather only the envelope of the respective square wave shape. Moreover, a measurement signal 26 recorded, for example, by the measurement unit 15 is illustrated in FIG. 27, which measurement signal represents the neuronal activity in the auditory cortex before and during the stimulation. The period $T_{stim}$ presently amounts to 1/(3.5 Hz)=0.29 s.

The stimulation is started at the point in time $t_{start}$. It can be seen for the measurement signal 26, which in the present example has been band pass filtered, that the neurons have a synchronous and oscillatory activity in the auditory cortex before the start of the stimulation. Shortly after the start of the stimulation the pathological synchronous neuronal activity is already suppressed in the target region.

It can be deviated from the strongly periodic stimulation pattern shown in FIGS. 26 and 27 in different ways and manners. For example, the delay in time τ between two sinusoidal oscillations following one another need not necessarily be of equal size. It can be provided that the spacing in time between the individual sinusoidal oscillation pulses is selected differently. Moreover, the delay times can also be varied during the treatment of a patient. The delay times can also be adjusted with regard to the psychological signal running times.

Furthermore, pauses can be provided during the application of the acoustic first stimuli 21, during which pauses no stimulation takes place. The pauses can be selected of arbitrary length and can, in particular amount to an integer multiple of the period $T_{stim}$. The pauses can be maintained in accordance with an arbitrary number of stimulations. E.g. a stimulation can be carried out during N periods of the length $T_{stim}$ following one another and a stimulation pause can subsequently be maintained during M periods of the length $T_{stim}$, wherein N and M are small integers, e.g. in the range of 1 to 15. This scheme can either be periodically continued or be modified stochastically and/or deterministically, for example, chaotically.

Figure 28:
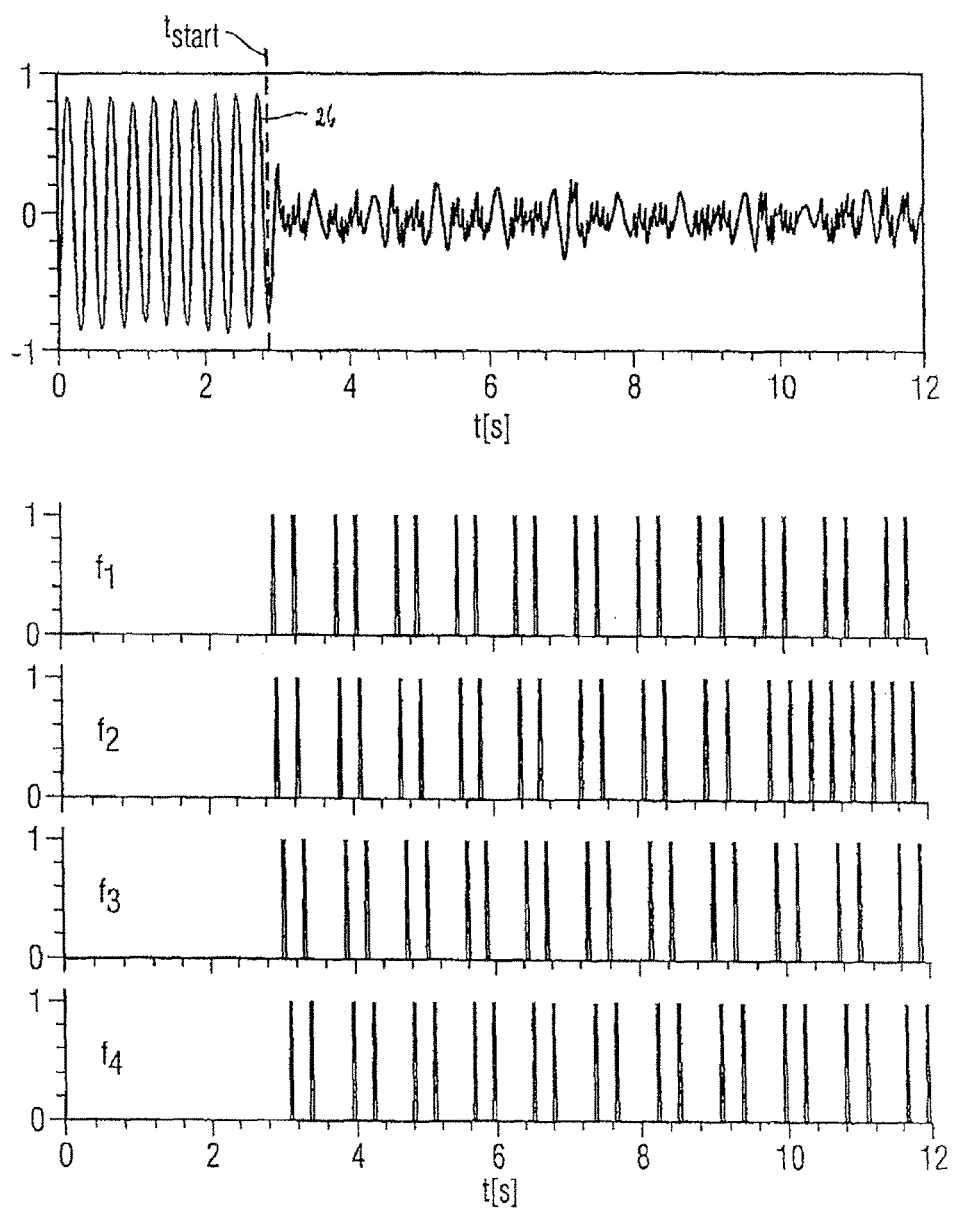
Figure 23:
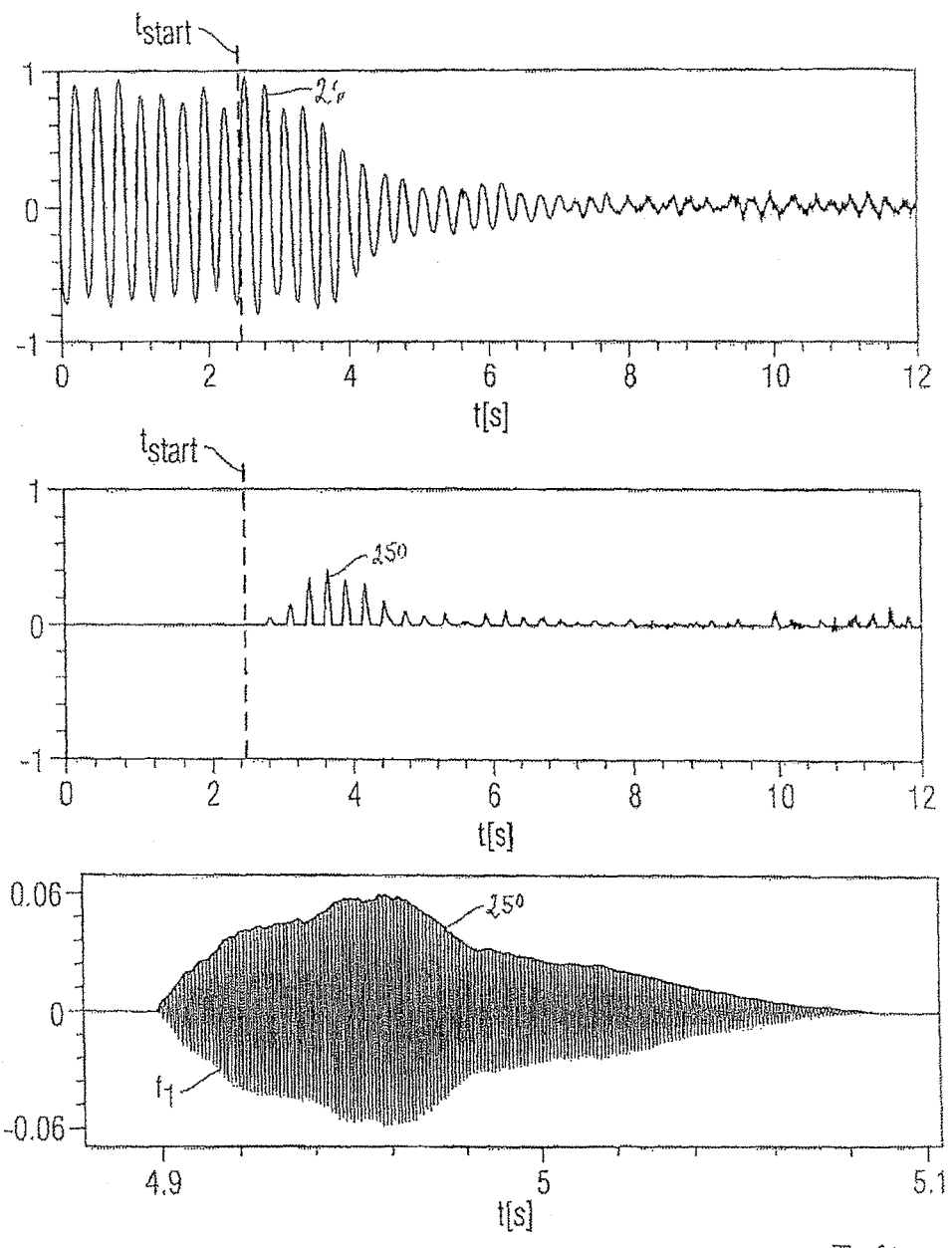

Such a stimulation is shown in FIG. 28. In this example N=2 and M=1. Otherwise, the stimulation corresponds to the stimulation shown in FIG. 27.

A further possibility of deviating from the strongly periodic stimulation pattern shown in FIG. 26 consists therein in varying the spacing in time between pulses of a frequency $f_1$ or of a frequency mixture with the boundaries $f_j^{unten}$ and $f_j^{oben}$ (j=1, 2, 3, 4) following one another stochastically or deterministically or mixed stochastic-deterministically.

Furthermore, the sequence in which the concerned frequencies f or the frequency mixtures with the boundaries $f_j^{unten}$ and $f_j^{oben}$ are applied can be varied per period $T_{stim}$ (or in different time steps). This variation can take place stochastically or deterministically or mixed stochastic-deterministically.

Moreover, only a certain number of the frequencies $f_j$ or of the frequency mixtures having the boundaries $f_j^{unten}$ and $f_j^{oben}$ can be applied per period $T_{stim}$ (or in a different time interval) and the frequencies $f_j$ or the frequency mixtures with the boundaries $f_j^{unten}$ and $f_j^{oben}$ associated with the stimulation can be varied in each time interval. Also this variation can take place stochastically or deterministically or mixed stochastic-deterministically.

The previously described stimulation signals bring about a reset of the phase of the neuronal activity of the pathological neuron population the different stimulation points is reset at different points in time. Thereby the pathological neuron population, whose neurons were previously active synchronously and active with the same frequency and phase, is split up into several sub-populations which finally leads to a desynchronization.

In the following further embodiments of the "closed loop" stimulation are described which can, for example, be carried out by means of the apparatus 2500 shown in FIG. 25. As was already described above, the measurement signal 26 recorded by the measurement unit 15 can be used to generate a control signal 23 with which the first stimulation unit 11 can be controlled. In this respect the measurement signal 26 can be transformed either directly or possibly following one or more processing steps into the acoustic first stimuli 21 and can be applied by the first stimulation unit 11. The calculation mode is in this respect selected so that the pathological neuronal activity is counteracted and the acoustic first stimuli 21 likewise diminish with the decreasing pathological neuronal activity or are at least strongly reduced in their strength.

Before the measurement signal 26 is introduced into the control input of the stimulation unit 11 the measurement signal 26 can be processed linearly or non-linearly. The measurement signal 26 can, for example, be filtered and/or amplified and/or a time delay can be applied and/or be mixed with a different measurement signal 26. The amplitude of a sinusoidal oscillation having a frequency in the audible range can moreover be modulated with the measurement signal 26 or with the processed measurement signal 26 and the amplitude modulated sinusoidal oscillation can then be applied by means of the acoustic generator as an acoustic first stimulus 21 or as a part thereof.

The complete measurement signal 26 need not necessarily be utilized for the amplitude modulation of a sinusoidal oscillation or of a different oscillating oscillation. It can e.g. be provided that only a part of the measurement signal 26 or of the measurement signal 26 to be processed can be used, for example, the part which lies above or below a certain threshold value. Such an amplitude modulation is illustrated by way of example in FIG. 29. The band pass filtered measurement signal 26 is applied against the time t in the upper graph of FIG. 29, moreover the start point in time $t_{start}$ of the stimulation is provided. The modulation signal 250 obtained from the measurement signal 26 is illustrated in the middle graph. The measurement signal 26 has been non-linearly processed and all measurement values of the measurement signal 26 and/or or of the processed measurement signal 26 have been set to zero for the generation of the modulation signal 250. The modulation signal 250 has moreover been delayed with regard to the measurement signal 26. Subsequently, the thereby obtained half wave signal 250 was multiplied with a sinusoidal oscillation of the frequency $f_1=1000$ Hz. The modulation signal 250 represents the envelope of the sinusoidal oscillation, as is shown in the lowest graph of FIG. 29 for a small section of time. The thereby obtained amplitude modulated sinusoidal oscillation is subsequently coupled back into the first stimulation unit 11 in order to be transformed by the acoustic generator into the acoustic first stimuli 21.

Instead of a sinusoidal oscillation with a single frequency, the modulation signal 250 can also be multiplied with an arbitrary mixture of sinusoidal oscillations (or other oscillations) in the audible frequency range, in dependence on where the desynchronization should take place at which points of the auditory cortex.

It can be seen from the extent of the measurement signal 26 illustrated in FIG. 29 that the acoustic non-linear time delayed half wave stimulation leads to a robust suppression of the pathological synchronous neuronal activity. The effective mechanism of this stimulation differs, however, from the effective mechanism of the stimulation method shown e.g. in FIG. 26. For the stimulation illustrated in FIG. 29 the phase of the neuronal activity is not reset into the respective stimulated sub-populations, rather the synchronization is suppressed in the pathologically active neuron population in that the saturation process of the synchronization is influenced.

In the following it will be explained with reference to an example how a measurement signal 26 obtained from the measurement unit 15 can be subjected to a non-linear processing before it is used as a control signal of the first stimulation unit 11.

Starting point is an equation for the control signal S(t):

$$S(t)=K\cdot Z^2(t)\cdot Z^*(t-\tau) \tag{1}$$

In equation (1) K is an amplification factor which can be suitably selected and Z(t) is a mean state variable of the measurement signal 26. Z(t) is a complex variable and can be illustrated as follows:

$$Z(t)=X(t)+iY(t), \tag{2}$$

wherein X(t), can e.g. correspond to the neurological measurement signal 26. Since the considered frequencies lie in the range of 10 Hz=1/100 ms=1/$T_\alpha$, the imaginary part Y(t) can be approximated through $X(t-\tau_\alpha)$, wherein for example, $\tau_\alpha=T_\alpha/4$ is true. Thus the following results:

$$S(t)=K\cdot[X(t)+iX(t-\tau_\alpha)]^2\cdot[X(t-\tau)-iX(t-\tau-\tau_\alpha)] \tag{3}$$

Equation (3) can be transformed as follows:

$$S(t)=K\cdot[X(t)^2\cdot X(t-\tau)+i2X(t)\cdot X(t-\tau_\alpha)\cdot X(t-\tau)-X(t-\tau_\alpha)\cdot X(t-\tau)-iX(t-\tau-\tau_\alpha)\cdot X(t)^2+2X(t)\cdot X(t-\tau_a)\cdot X(t-\tau-\tau_\alpha)+iX(t-\tau-\tau_\alpha)\cdot X(t-\tau_\alpha)] \tag{4}$$

The real part of the equation (4) is used as a control signal for the stimulation unit 11:

$$\mathrm{real}[S(t)]=K\cdot[X(t)^2\cdot X(t-\tau)-X(t-\tau_\alpha)\cdot X(t-\tau)+2X(t)\cdot X(t-\tau_a)\cdot X(t-\tau-\tau_\alpha)] \tag{5}$$

The auditory cortex can further be stimulated at different points in a targeted manner with the feedback coupled and possibly further processed measurement signal 26. In the case of the above-described four different frequencies $f_1$ to $f_4$ the possibly further processed measurement signal 26 is subjected to a corresponding time delay and is multiplied with the frequencies $f_1$ to $f_4$. As long as the stimulation should be less focal, but should rather be carried out more expanded, four different frequency mixtures with the boundaries $f_j^{unten}$ and $f_j^{oben}$ (j=1, 2, 3, 4) are used rather than the pure sinusoidal oscillations of the frequencies $f_1$ to $f_4$.

Figure 30:
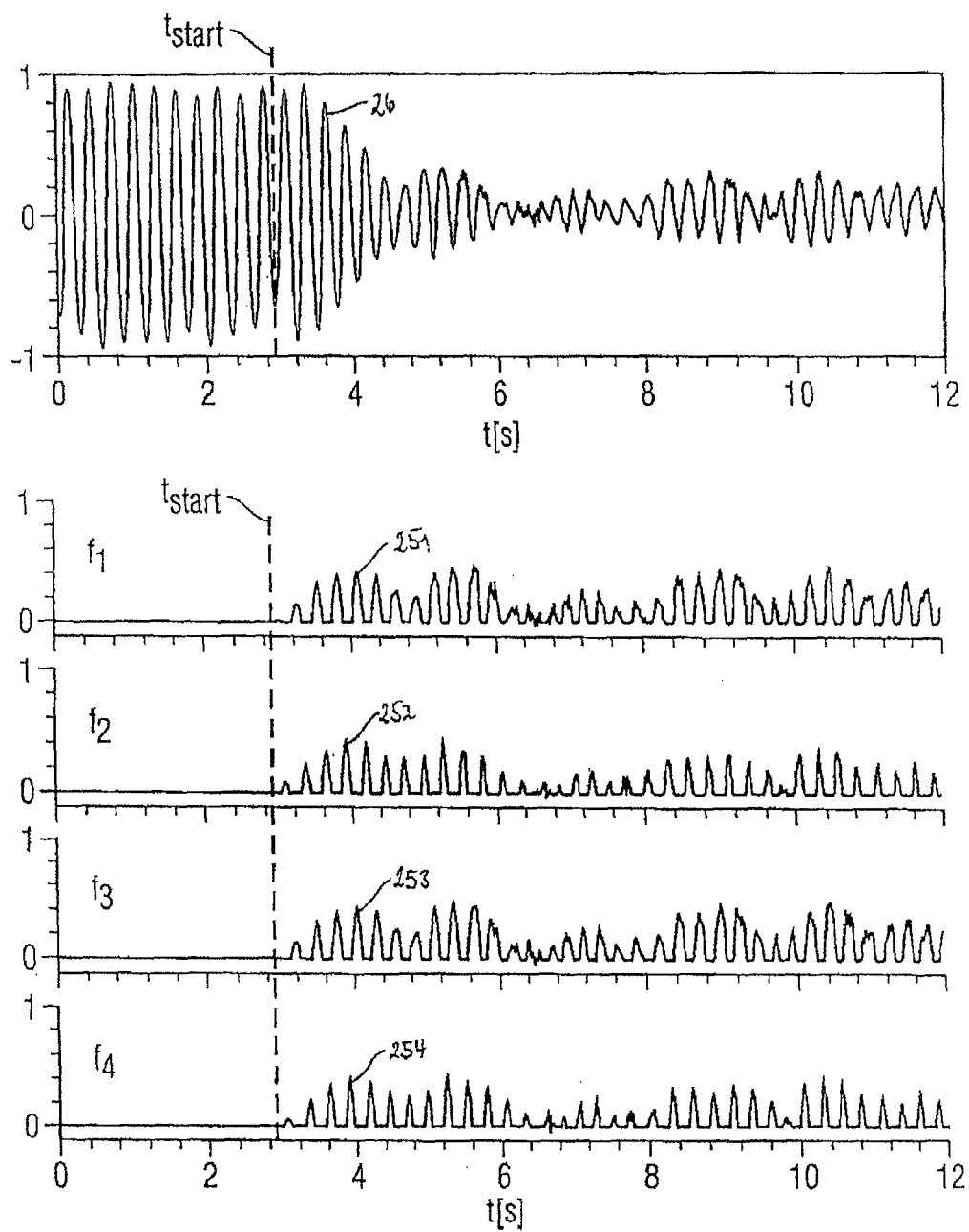

Such a stimulation is illustrated by way of example in FIG. 30. The modulation signals 251, 252, 253 and 254 with which the amplitude modulation of the frequency $f_1$ to $f_4$ should be carried out are obtained through linear processing steps from the band pass filtered measurement signal 26 in this example. The control signal 23 has been generated through the superposition of the modulated sinusoidal oscillations which control signal has been transformed into the acoustic first stimuli 21 by the acoustic generator 11.

In the following it will be explained by way of example with reference to FIGS. 31A and 31B how the modulation signals 251 to 254 can be obtained from the measurement signal 26. For this purpose initially a delay time τ is determined which in the present example has been set to $\tau=T_{stim}/2$ (other values such as e.g. $\tau=T_{stim}$ or $\tau=3T_{stim}/2$ are likewise possible). The frequency $f_{stim}=1/T_{stim}$ can, for example, lie in the range of the mean frequency of the measurement signal 26, e.g. in the range of 1 to 30 Hz in particular in the range of 5 to 20 Hz. Specific delay times $\tau_1$, $\tau_2$, $\tau_3$ and $\tau_4$ can be calculated for each of the modulation signals 251 to 254 on the basis of the delay time τ, for example, with reference to the following equation:

$$\tau_j=\tau\cdot 11-2\cdot(j-1)/8 \; mit=1,2,3,4 \tag{6}$$

The modulation signals 251 to 254 can, for example, be obtained from the measurement signal 26 in that the measurement signal 26 is respectively delayed by the delay times $\tau_1$, $\tau_2$, $\tau_3$ and/or $\tau_4$:

$$S_j(t)=K\cdot Z(t-\tau_j) \tag{7}$$

In equation (7), $S_1(t)$, $S_2(t)$, $S_3(t)$ and $S_4(t)$ represent the modulation signals 251 to 254 and Z(t) represents the measurement signal 26. K is an amplification factor which can be suitably selected. All negative values (or all values above or below a certain threshold value) of the modulation signals $S_1(t)$ to $S_4(t)$ can moreover be set to zero.

Figure 31A:
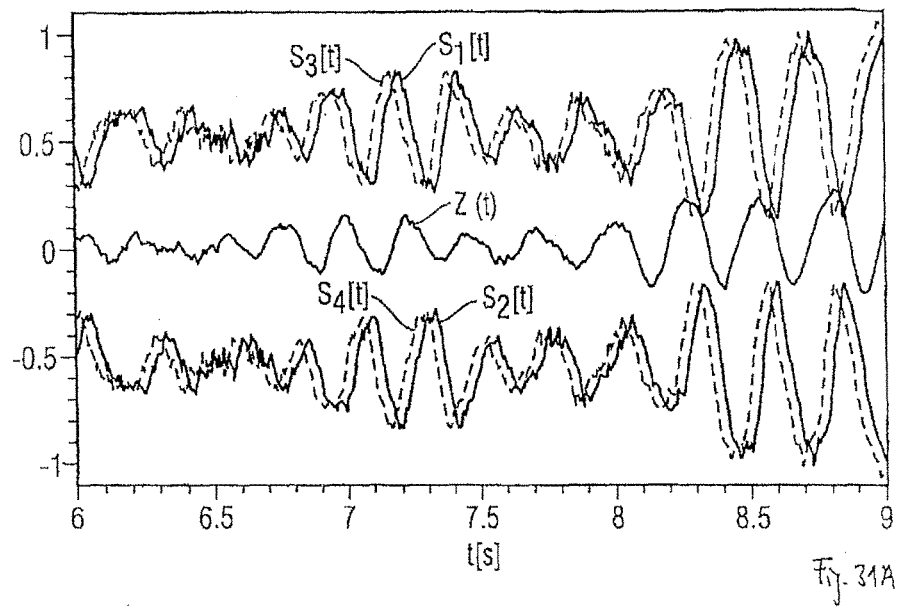
FIGS. 31A and 31B schematic illustrations of the generation of modulation signals.
Figure 31B:
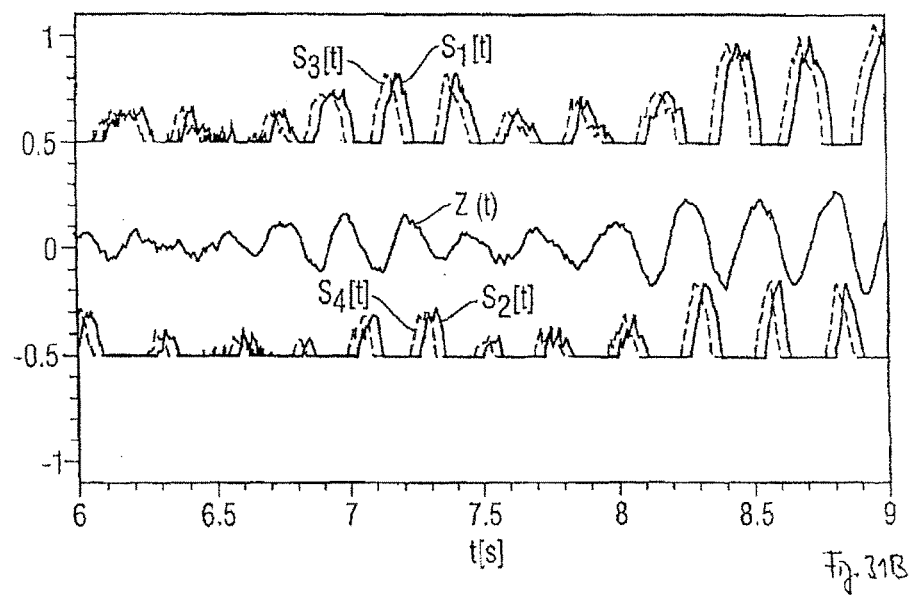

In accordance with an embodiment illustrated in the FIGS. 31A to 31B, the modulation signals $S_1(t)$ to $S_4(t)$ are only calculated from the delay times $\tau_1$ and $\tau_2$ when the modulation signals $S_1(t)$ and $S_2(t)$ and/or $S_3(t)$ and $S_4(t)$ respectively have different polarities:

$$S_1(t)=K\cdot Z(t-\tau_1) \quad (8)$$

$$S_2(t)=-K\cdot Z(t-\tau_1) \quad (9)$$

$$S_3(t)=K\cdot Z(t-\tau_2) \quad (10)$$

$$S_4(t)=-K\cdot Z(t-\tau_2) \quad (11)$$

For a clearer illustration, the modulation signals $S_1(t)$ and $S_3(t)$ are displaced by the value 0.5 towards the top and the modulation signals $S_2(t)$ and $S_4(t)$ are displaced by the value 0.5 to the bottom in the FIGS. 31A and 31B.

All negative values (or all values above or below a certain threshold value) of the modulation signals $S_1(t)$ to $S_4(t)$ can be set to zero as is shown in FIG. 31B. The generation of the modulation signals 251 to 254 shown in FIG. 30 corresponds to the generation of the modulation signals $S_1(t)$ to $S_4(t)$ shown in the FIGS. 31A and 31B.

Stimulation Units for the Generation of Specific Tactile, Vibratory and/or Thermal Stimuli:

Embodiments of the non-invasive first stimulation unit 11 for the generation of tactile, vibratory and/or thermal first stimuli 21 will be described in the following. Such stimulation units can also be found in the German patent application no. 10 2010 000 390.5 having the title "Apparatus and method for the treatment of a patient with vibration stimuli, touch stimuli or thermo stimuli" which was filed at the German Patent and Trademark Office on Feb. 11, 2010. The overall contents of disclosure the German patent application no. 10 2010 000 390.5 is hereby incorporated into the disclosure of the present patent application.

In the following reference will only be made to the generation of the tactile, vibratory and thermal first stimuli 21. It is naturally understood that these specific first stimuli 21 can be applied in combination with the non-specific second stimuli 22, like they were described above e.g. in connection with the FIGS. 1 to 5.

Figure 32:
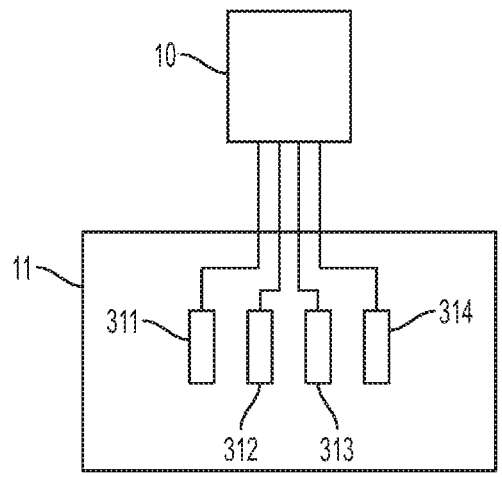
FIG. 32 a schematic illustration of a stimulation unit for the generation and application of specific tactile, vibratory and/or thermal stimuli in accordance with an embodiment.

FIG. 32 schematically shows an embodiment of the first stimulation unit 11 which includes a plurality of stimulation elements. In the present embodiment the first stimulation unit 11 has four stimulation elements 311, 312, 313, 314 which are controlled by the control unit 10. The design shown in FIG. 32 is to be understood merely by way of example. As an alternative to this design the first stimulation unit 11 can include an arbitrary number N (N=2, 3, 4, 5, 6, 7, 8, 9, 10, 11, 12, . . . ) of stimulation elements.

The stimulation elements 311 to 314 are designed such that they can be placed onto the skin of the patient. Depending on the illness and/or of the concerned body parts, the stimulation elements 311 to 314 can be attached to the skin of the patient in a suitable arrangement, for example, at an arm, at a leg, at the hand and/or at a foot of the patient. Tactile, vibratory and/or thermal first stimuli 21 can be administered at the skin either individually or in combination in dependence on the type of illness.

The plurality of stimulation elements 311 to 314 enable a stimulation of different receptive regions of the skin to take place in a manner coordinated in time and space via the individual stimulation elements 311 to 314. The stimulation elements 311 to 314 can be arranged on the skin of a patient so that the stimuli applied at the skin tissue are guided to different target regions via nerve lines, which e.g. lie in the spinal cord and/or in the brain. Consequently, different target regions can be stimulated in the spinal cord and/or in the brain during the same stimulation period with possibly different stimuli and/or time shifted stimuli.

Figure 33:
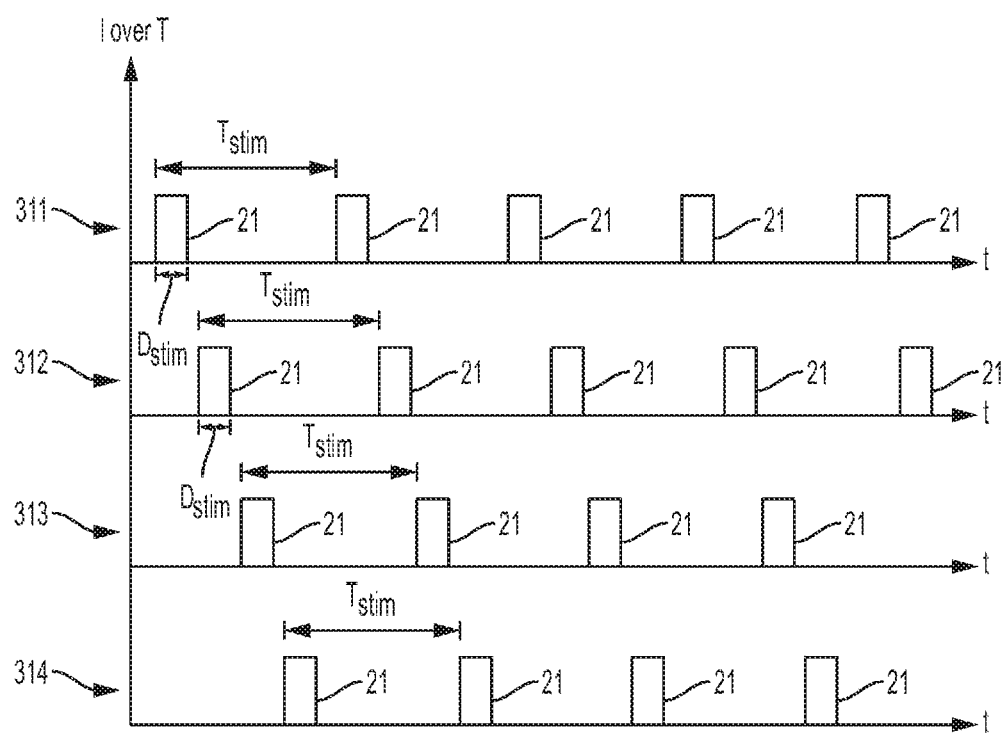
FIG. 33 a schematic illustration of a tactile, vibratory and/or thermal stimulation method.

A stimulation method which can be carried out with the first stimulation unit 11 shown in FIG. 32 is schematically illustrated in FIG. 33. In FIG. 33 the first stimuli 21 applied via the stimulation elements 311 to 314 are shown beneath one another applied against the time t.

Each of the stimulation elements 311 to 314 applies the first stimulus 21 periodically to the respective receptive region of the skin at which the stimulation elements 311 to 314 is attached in the method illustrated in FIG. 33. The frequency $f_{stim}=1/T_{stim}$ ($T_{stim}$=duration of period) with which the first stimuli 21 can be repeated which are generated by each of the stimulation elements 311 to 314 can lie in the range of 1 to 60 Hz and in particular in the range of 30 to 60 Hz or can lie in the range of 1 to 30 Hz or in the range of 1 to 20 Hz or in the range of 5 to 20 Hz can, however, also take on smaller or larger values. The duration $D_{stim}$ of an individual first stimulus 21 can in particular depend on the type of stimulation. The ordinate shown in FIG. 33 likewise depends on the type of the first stimulus 21. For a vibration stimulus or a touch stimulus the deflection 1 of a stimulation element can, for example, be applied against the time t; for a thermo stimulus a temperature T can be illustrated. The first stimuli applied by the different stimulation elements 311 to 314 can be identically or can also be different.

Figure 34A:
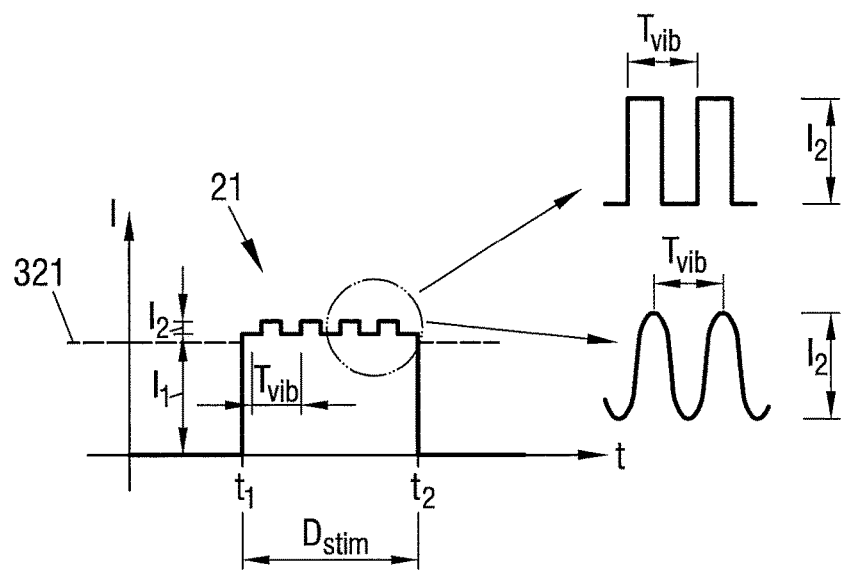
FIGS. 34A to 34D schematic illustrations of specific vibratory stimuli.

Different embodiments of individual vibratory first stimuli 21 are illustrated in FIGS. 34A, 34B, 34C and 34D. There the deflection 1 of the stimulation element is applied against the time t. In FIG. 34A the stimulation element is deflected from its rest position and is pressed into the skin of a patient at the time $t_1$. The position of the skin surface is illustrated by a dotted line 321. Once the stimulation element has come into contact with the skin a periodic vibration stimulus with a frequency of $f_{vib}=1/T_{vib}$ in the range of 30 to 300 Hz is applied ($T_{vib}$=duration of period of the vibration stimulus). The stimulation element can exert a force of approximately 2 N at a frequency $f_{vib}$ of 300 Hz. The duration $D_{stim}$ of the vibration stimulus 20 can lie in the range of 10 to 500 ms. In particular the duration of stimulation $D_{stim}$ lies in the region of $$0<D_{stim}<T_{stim}/N, \quad (12)$$

wherein N is the number of stimulation elements. E.g. a range of 10 to 250 ms results for $T_{stim}=1$ Hz and N=4 for the duration of stimulation $D_{stim}$. However, also stimuli overlapping in time can be used.

At the time $t_2$ the stimulation element is again brought into its rest position where it has no contact with the skin. As is shown in FIG. 34A, the vibratory first stimulus 21 can be a square wave shaped stimulus or a sinusoidal shaped stimulus, however, it can also have a different shape. The deflection $l_1$ shown in FIG. 34A for the depression of the stimulation element into the skin can lie in the range of 0.5 to 3 mm. The deflection $l_2$ of the stimulation element during the vibration can amount to between 0.1 and 0.5 mm.

Figure 34B:
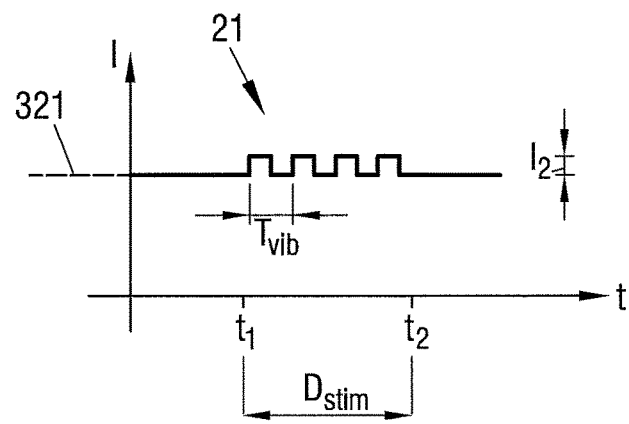

A variation of the vibratory first stimulus 21 illustrated in FIG. 34A is shown in FIG. 34B. For the embodiment shown in FIG. 34B the stimulation element is constantly in contact with the skin of the patient. During the stimulation period of time $D_{stim}$ a vibratory first stimulus 21 is applied as described above.

Figure 34C:
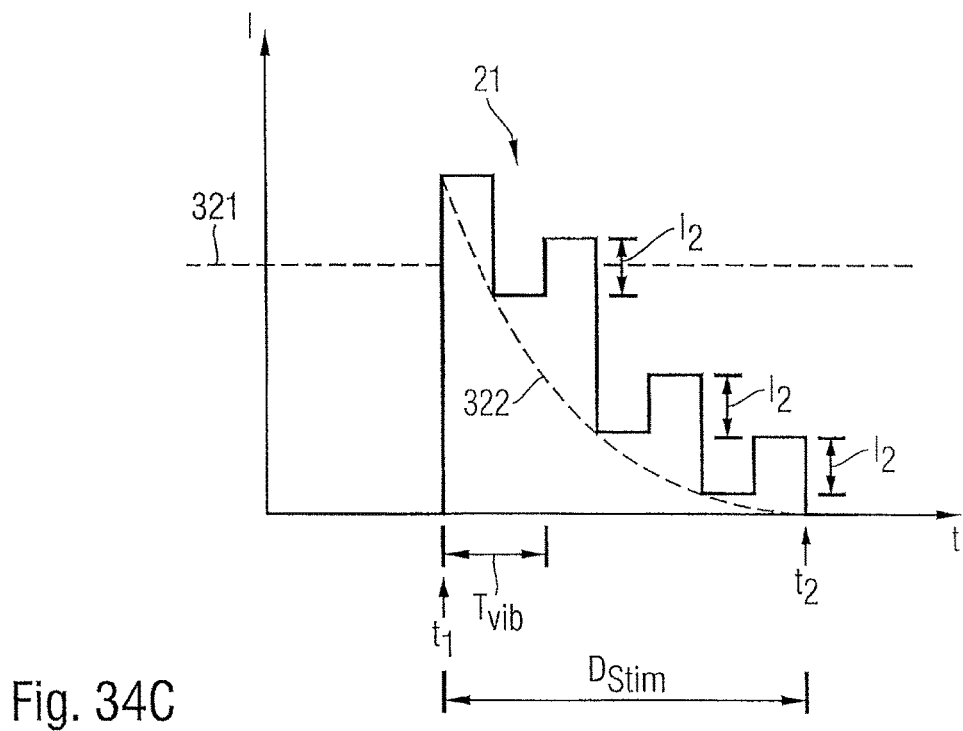

A further variation of the vibratory first stimulus 21 is illustrated in FIG. 34C. In contrast to the vibratory first stimulus 21 of FIG. 34A the stimulation element is retracted already during the stimulation period $D_{stim}$ so that the vibration presses less into the skin with increasing duration of time and the stimulation element is finally completely released from the skin. The retraction of the stimulation element can, for example, take place along a linear or nonlinear, e.g. exponential curve 322 onto which the vibrations $f_{vib}$ of the stimulation elements are overlapped. In the example shown in FIG. 34C, the trailing edge of each of the pulses reaches down to the curve 322. The pulse subsequent thereto has a fixedly predetermined height $l_2$ this means that the leading edge of each pulse has a height $l_2$.

Figure 34D:
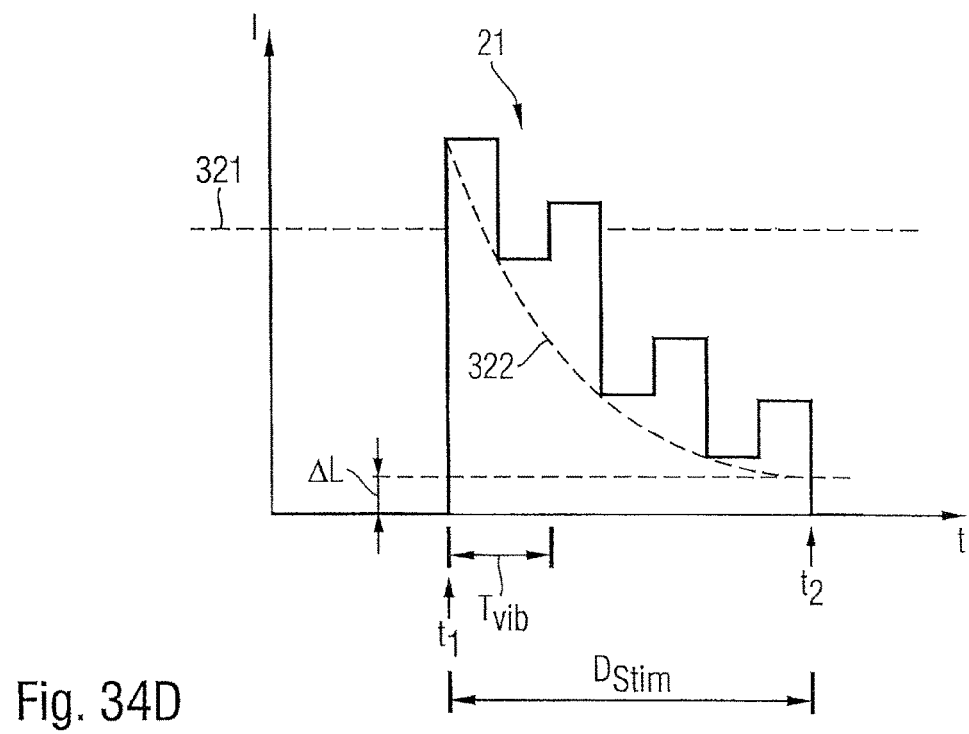

A variation of the vibratory first stimulus 21 of FIG. 34C is illustrated in FIG. 34D. There the curve 322 does not go back to the zero line (l=0) but rather has a fixedly predetermined offset ΔL from the zero line.

Figure 35:
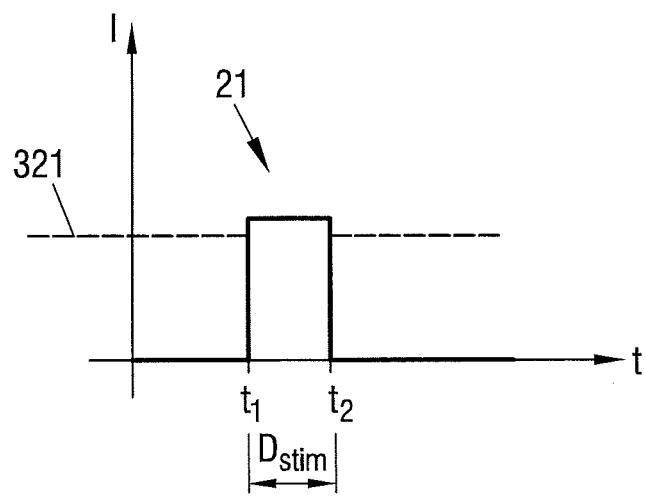
FIG. 35 a schematic illustration of a specific tactile stimulus.

An embodiment of a tactile first stimulus 21 is shown in FIG. 35. The stimulation element is pressed into the skin of the patient at the time $t_1$, remains there for the duration of stimulation $D_{stim}$ and is retracted again at the time $t_2$. The duration of stimulation $D_{stim}$ lies in the range of 10 to 500 ms for a tactile first stimulus 21. The duration of stimulation $D_{stim}$ in particular lies in the range provided above at (12), however, also stimuli overlapping in time can be used.

Figure 36A:
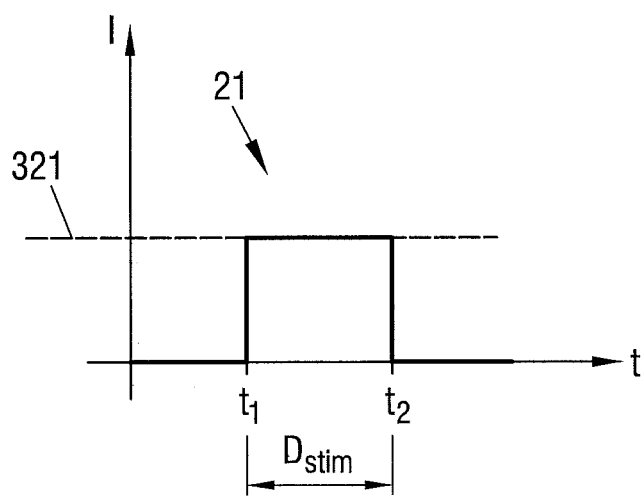
FIGS. 36A to 36C schematic illustrations of specific thermal stimuli.
Figure 36B:
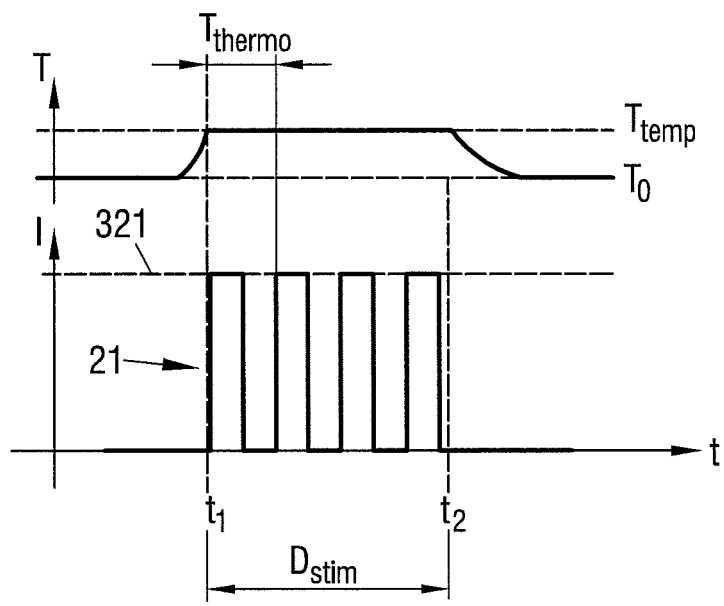
Figure 36C:
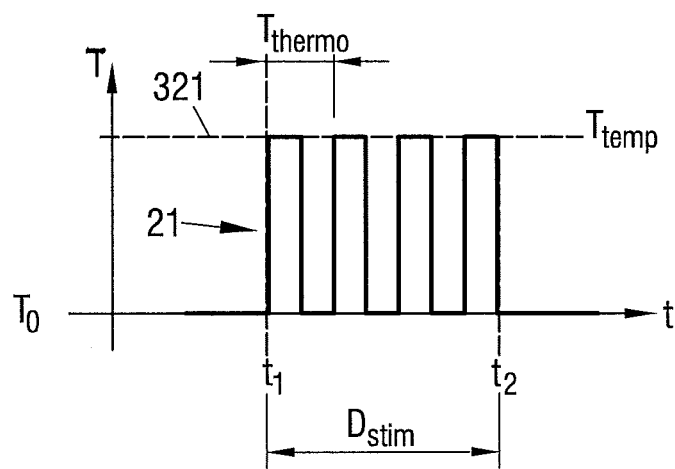

Different embodiments of individual thermal first stimuli 21 are illustrated in FIGS. 36A, 36B and 36C. For the embodiments shown in the FIGS. 36A and 36B a stimulation element is heated or cooled to a temperature $T_{temp}$. As is shown in FIG. 36B, the temperature $T_{temp}$ can be generated just before the application of the thermal first stimulus 21. In this case the stimulation element has a temperature $T_0$, which e.g. corresponds to the room temperature, during the stimulation pauses. Alternatively, the stimulation element can be maintained at a constant temperature $T_{temp}$.

In the embodiment in accordance with FIG. 36A the heated or cooled stimulation element is brought to the skin of the patient at the time $t_1$ and remains there for the overall duration of stimulation $D_{stim}$. In contrast to this the stimulation element is brought to the skin and removed again during the stimulation period $D_{stim}$ periodically with a frequency $f_{thermo}$ in the embodiment in accordance with FIG. 36B. The frequency $f_{thermo}=1/T_{thermo}$ can lie in the range of 1 to 10 Hz ($T_{thermo}$=duration of the period of the thermo stimulus).

The thermal first stimulus 21 shown in FIG. 36C substantially corresponds to the thermo stimulus 21 of FIG. 36B. The difference is that the thermo stimulus 21 of FIG. 36C is generated in a contact-free manner. In this example the stimulation temperature $T_{temp}$ is generated through electromagnetic radiation, for example infrared light. The electromagnetic radiation is moreover varied periodically with the frequency $f_{thermo}=1/T_{thermo}$ (e.g. through a switching on and a switching off of an infrared radiator).

The stimulation period $D_{stim}$ lies in the range of 10 to 500 ms for thermal first stimuli 21. The duration of stimulation $D_{stim}$ in particular lies in the range provided above in (12); however, stimuli overlapping in time can also be used. The temperature $T_{temp}$ can amount to from 22 to 42° C. The temperature $T_0$ is generally the body temperature of the patient. The frequency $f_{thermo}$ can lie between 1 and 10 Hz can, however, also lie outside of this range.

It is also plausible that an individual first stimulus 21 comprises a plurality of types of stimuli. For example, the vibratory first stimulus 21 illustrated in FIG. 34A can simultaneously be a thermo stimulus, as long as the stimulation element carrying out the stimulus is correspondingly heated or cooled. The vibratory first stimulus 21 of FIG. 34A is simultaneously also a touch stimulus (touch receptors are activated through the contacting of the stimulation element at the skin).

First stimuli 21 applied by the stimulation units 311 to 314 are received by receptors lying in or beneath the skin and are guided to the nerve system. These receptors include, for example Merkel cells, Ruffini bodies, Meissner bodies and hair follicle receptors, which in particular act as receptors for the tactile first stimuli 21. The vibratory first stimuli 21 generally target the depth sensibility. The vibratory first stimuli 21 can be received by receptors lying in the skin, in the muscles, in the subcutaneous tissue and/or in the tendons of the patient. The Vater-Pacini bodies should be mentioned by way of example as receptors for the vibratory first stimuli 21 which convey vibratory sensations and accelerations. The thermal first stimuli 21 are received by the thermo receptors of the skin. These are heat receptors (also referred to as warm receptors, heat sensors or warm sensors) and cooling sensors (also referred to as cool sensors, cooling receptors or cool receptors). The cooling sensors lie towards the surface in the skin of the patient, the heat receptors a little deeper.

The first stimuli 21 generated by the stimulation elements 311 to 314 are designed such that a reset of the phase of the neuronal activity of the stimulated neuron can be brought about in the neuron population when they are received by the corresponding receptors and they are guided to a neuron population in the brain or in the spinal cord having a pathological synchronous and oscillatory activity via the nerve paths. Through the reset the phase of the stimulated neurons is set independent of the actual phase value to a certain phase value, e.g. of 0°. Thus, the phase of the neuronal activity of the pathological neuron population is controlled by means of a targeted stimulation.

It is moreover possible to stimulate the pathological neuron population at different positions on the basis of the plurality of stimulation elements. The first stimuli 21 applied at different positions of the skin are namely guided to different parts in the brain or the spinal cord. This enables a reset of the phase of the neuronal activity of the pathological neuron population at the different stimulation points at different points in time. As a result the pathological neuron population whose neurons were previously synchronous and active with the same frequency and phase are thereby divided into several sub-populations. Within one sub-population the neurons are still synchronous and also still fire with the same pathological frequency, however, each of the sub-populations has the phase with regard to its neuronal activity which was forced thereupon through the stimulation stimulus.

The state with at least two sub-populations generated by the stimulation is instable due to the pathological interaction between the neurons and the overall neuron population approximates quickly to a state of complete desynchronization in which the neurons fire in an uncorrelated manner. The desired state, this means the state of complete desynchronization, is thus not immediately present following the application of the first stimuli 21, but is set typically within a few periods or even less than a period of the pathological activity.

Figure 37:
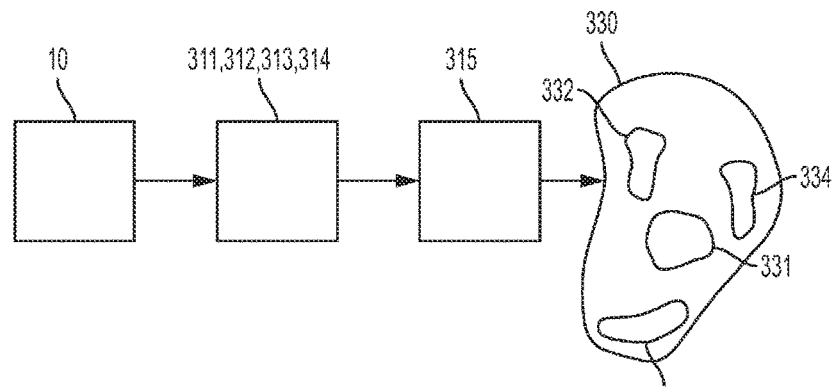
FIG. 37 a schematic illustration of a stimulation unit for the generation and application of specific tactile, vibratory and/or thermal stimuli in accordance with an embodiment.

The stimulation of a plurality of sub-populations of a pathologically active neuron population 330 with the aid of the first stimulation unit 11 is schematically illustrated in FIG. 37. The first respective receptors are stimulated with tactile first stimuli 21 and/or with vibratory first stimuli 21 and/or with thermal first stimuli 21 by the stimulation elements 311 to 314 of the first stimulation unit 11 at different points of the skin 315. The first stimuli 21 applied by the stimulation elements 311, 312, 313 and 314 are guided to different sub-populations 331, 332, 333 and/or 334 of the neuron population 330 (stimuli of stimulation element 311 to sub-population 331, stimuli of stimulation elements 312 to sub-population 332, stimuli of stimulation element 313 to sub-population 333 and stimuli of stimulation element 314 to sub-population 334) and reset the phases of the sub-population to respectively different points in time, whereby a desynchronization of the overall neuron population 330 is achieved.

The targeted stimulation of certain regions of the brain or of the spinal cord is enabled through the somatopic association of body regions to these regions. For example, the stimulation elements 311 to 314 can be applied at the foot, at the lower leg, and at the upper leg or also at the hand, at the lower arm and at the upper arm of the patients. Different neurons are stimulated through the stimuli applied at the respective points due to the somatopic structure of the nerve conductor paths. The somatopic association of skin parts to regions of the brains is, for example, illustrated in A. Benninghoff et al.: "Lehrbuch der Anatomie des Menschen. Dargestellt unter Bevorzugung funktioneller Zusammenhänge. 3. Bd. Nervensystem, Haut and Sinnesorgane ("Textbook of the anatomy of the human. Illustrated on the preferred functional composition. 3rd Edition nervous sysem, skin and sensory organs"), published by Urban and Schwarzenberg, Munich 1964.

In order to achieve a desynchronization of the overall neuron population 330 through a time-displaced reset of the phases of the subpopulations 331 to 314 of the pathologically synchronous neuron population 330 one can proceed in different ways and manners. For example, the first stimuli 21, which bring about a reset of the phase of the neurons, can be provided to the respective receptive fields of the skin via the different stimulation elements 311 to 314. Furthermore, the stimuli can be applied e.g. phase-shifted or with different polarities, so that they also result in a time-shifted reset of the phases of the different sub-populations 331 to 334.

Figure 38:
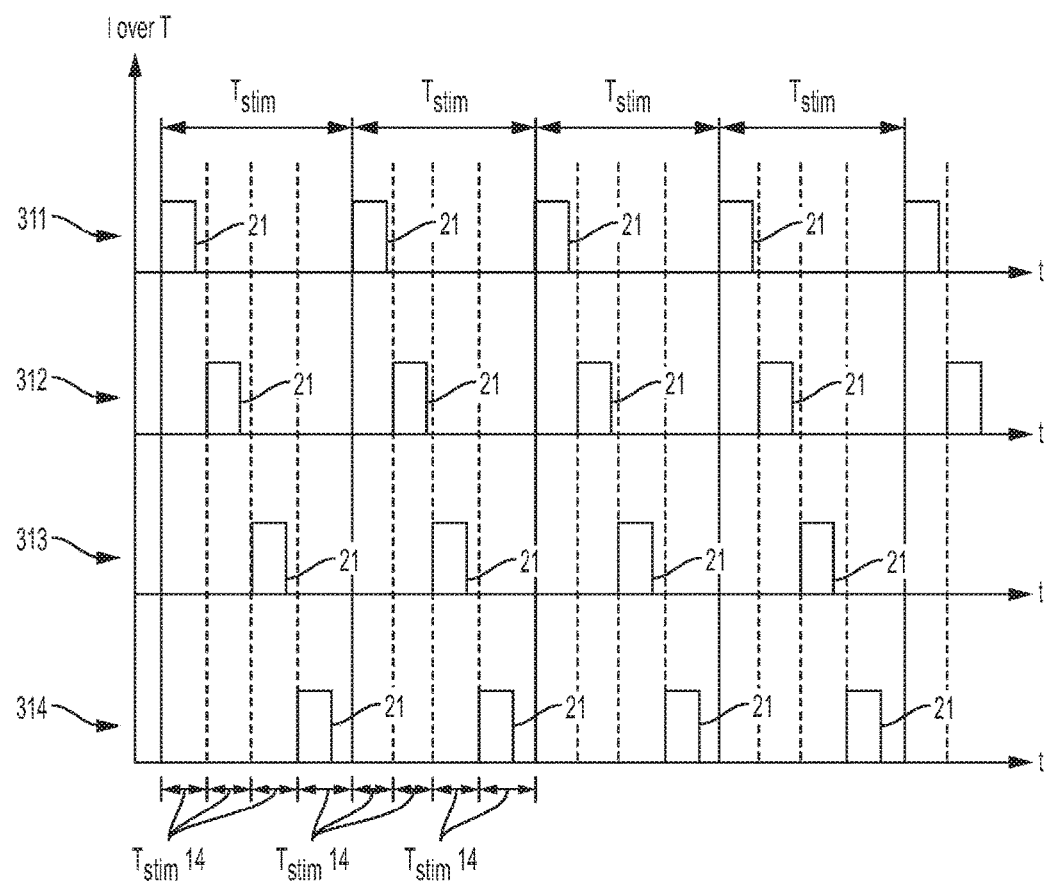
FIGS. 38 to 40 schematic illustrations of tactile, vibratory and/or thermal stimulation methods.

A stimulation method suitable for the above-described purpose is schematically illustrated in FIG. 38. The first stimuli 21 applied via the stimulation elements 311 to 314 are applied beneath one another against the time t in FIG. 38. For example, the vibration stimuli, the touch stimuli and the thermo stimuli illustrated in FIGS. 34A to 36C can be used as first stimuli 21. The diagram shown in FIG. 38 is divided into periodically repeating first sections of time of the length $T_{stim}$. The frequency $f_{stim}=1/T_{stim}$ with which the first sections of time of the length $T_{stim}$ are repeated can lie in the range of 1 to 60 Hz and in particular in the range of 30 to 60 Hz or in the range of 1 to 30 Hz or in the range of 1 to 20 Hz or in the range of 5 to 20 Hz can, however, also take on smaller or larger values.

The first sections of time of the length $T_{stim}$ are moreover divided into two sections of time of the length $T_{stim}/4$. For a stimulation over N stimulation units the first sections of time can be divided into N second sections of time of the length $T_{stim}/N$.

In accordance with an embodiment each of the stimulation elements 311 to 314 generates no more than one first stimulus 21 within a first section of time. First stimuli 21 can be generated by different stimulation elements 311 to 314 in second sections of time following one another.

For the embodiment illustrated in FIG. 38 each of the stimulation elements 311 to 314 applies a first stimulus 21 strongly periodically with the frequency $f_{stim}$. The administration of the first stimuli 21 via different stimulation elements 311 to 314 takes place with a delay in time between the individual stimulation elements 311 to 314 by about $T_{stim}/4$.

In the case of N stimulation elements the delay in time between two first stimuli respectively substantially following one another can, for example, lie in the range of an N-th of the period $1/f_{stim}$, this means that $1/(N \times f_{stim})=T_{stim}/N$, this means that in particular the time $T_{stim}/N$ passes between the start points in time of two first stimuli 21 following one another.

The frequency $f_{stim}$ can, for example, lie in the range of the mean frequency of the pathological rhythmic activity of the target network. For illnesses, in which an increased neuronal synchronization is present the mean frequency typically lies in the range of 1 to 30 Hz can, however, also lie outside of this region. In this context, it should be noted that the frequency with which the concerned neurons fire synchronously is typically not constant, but can rather more have variations and moreover have individual deviations for each patient.

It can be deviated from the strongly periodic stimulation pattern shown in FIG. 38 in the most different kinds and manner. For example, the time delay $T_{stim}$ of two first stimuli 21 following one another generated by the same stimulation element does not have to be of equal size, but can rather vary in the range of ±10% or ±5% or ±3% about $T_{stim}$. Moreover, also the distance in time between two first stimuli 21 following one another generated by different stimulation elements can vary in the range of ±10% or ±5% or ±3% about $T_{stim}/N$. It can by all means be provided that the separation in time between the individual first stimuli 21 is selected differently. Moreover, the delay times can also be varied during the treatment of a patient. The delay times can also be adjusted with regard to the physiological signal running times.

Furthermore, pauses can be provided during the application of the first stimuli 21 during which pauses no stimulation takes place. Such a pause is shown by way of example in FIG. 39. The pauses can be selected of arbitrary length and, in particular amount to an integer multiple of the period $T_{stim}$. Moreover, the pauses can be maintained after an arbitrary number of stimulations. For example, a stimulation can be carried out during N periods of the length $T_{stim}$ following one another and a pause can subsequently be maintained during M periods of the length $T_{stim}$ without stimulation, in which N and M are small integers, e.g. in the range of 1 to 10. This scheme can either be periodically continued or be modified stochastically and/or deterministically or mixed stochastic-deterministically.

A further possibility of deviating from the strongly periodic stimulation pattern shown in FIG. 38 consists therein in varying the sequence in time of the individual first stimuli 21 stochastically or deterministically or mixed stochastic-deterministically.

Figure 40:
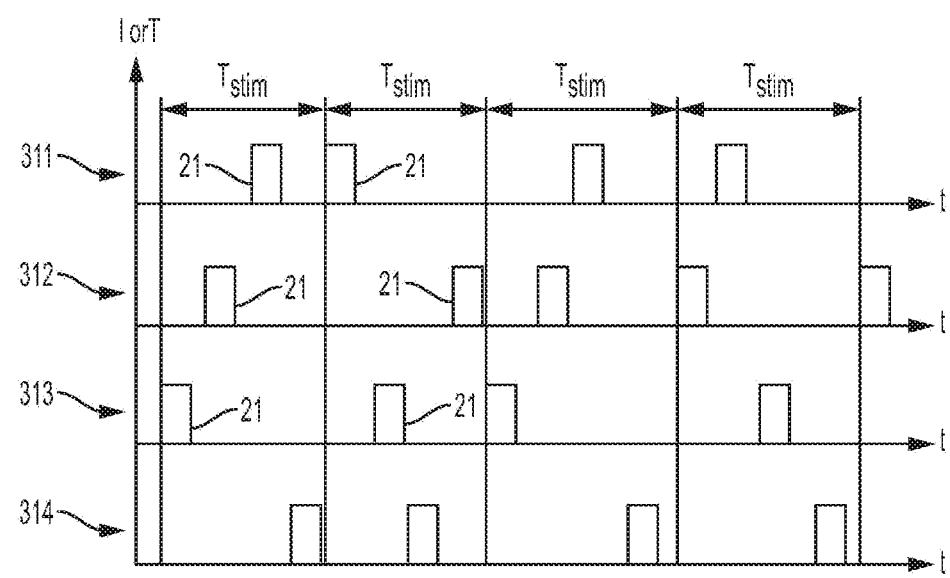

Furthermore, the sequence in which the stimulation elements 311 to 314 apply the first stimuli 21 can be varied per period $T_{stim}$ (or also in other time steps) as is shown by way of example in FIG. 40. This randomization can take place stochastically or deterministically or mixed stochastic-deterministically.

Figure 39:
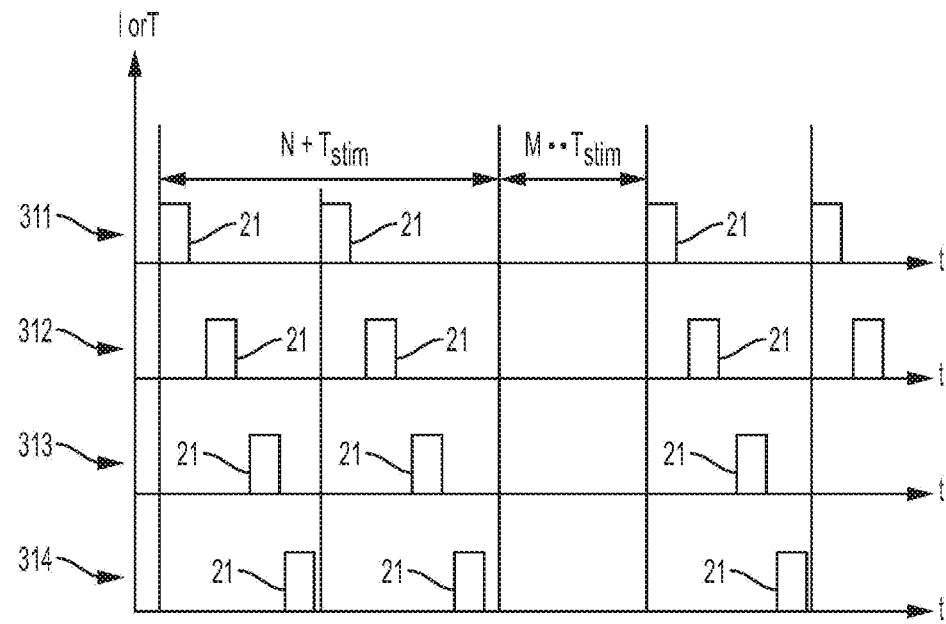

The randomization shown in FIG. 40 can be combined with the stimulation pattern shown in FIG. 39. For example, the length $T_{stim}$ of a repeated randomization can be carried out in each of the N stimulation sections of time following one another or, however, a randomization takes place after each pause of the length $M \times T_{stim}$ and the sequence in which the stimulation elements 311 to 314 apply the first stimuli 21 remains constant in the subsequently following N stimulation sections of time.

Moreover, only a certain number of stimulation elements 311 to 314 can be utilized for the stimulation per period $T_{stim}$ (or in any other time interval) and the stimulation elements associated with the stimulation can be varied in each time interval. This variation can also take place stochastically or deterministically or mixed stochastic-deterministically.

Figure 41:
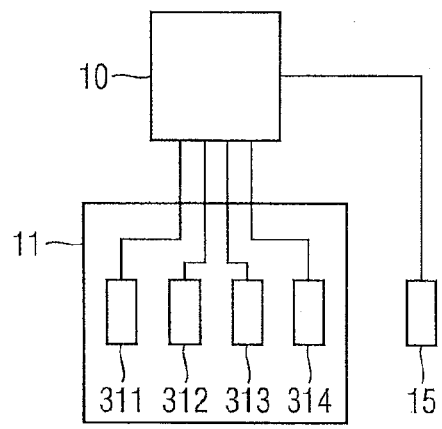
FIG. 41 a schematic illustration of a stimulation unit for the generation and application of specific tactile, vibratory and/or thermal stimuli in accordance with a further embodiment.

The first stimulation unit 11 can, for example, be operated in an "open loop"-mode in which the control unit 10 controls the stimulation elements 311 to 314 such that these generate the predefined first stimuli 21 which are provided to the skin tissue. Furthermore, the first stimulation unit 11 can be further developed together with the control unit 10 also to a "closed loop"-system schematically illustrated in FIG. 41. In this embodiment a measurement unit 15 is additionally provided which provides measurement signals recorded at the patient and guides these to the control unit 10. The measurement unit 15 can be non-invasive sensors or invasive sensors (cf. the above description in connection with FIG. 3).

Different embodiments are plausible with regard to the cooperation of the control unit 10 with the measurement unit 15.

For example,—as described above—a change can be made between the first mode of operation, the learning phase and the second mode of operation, the actual stimulation phase, on the basis of the measurement signals. Moreover, parameters of the first stimuli 21, e.g. a certain frequency $f_{vib}$ or an indentation depth 12 in the case of vibration stimuli, can be set by the control unit 10 on the basis of the extent of the pathological features.

Furthermore, it can be provided that the measurement signals recorded by the measurement unit 15 can be transformed directly or possibly following one or more processing steps into tactile first stimuli 21, vibratory first stimuli 2 land/or thermal first stimuli 21 and can be applied by the first stimulation unit 11. The measurement signals can, for example, be amplified and possibly following a mathematical calculation (e.g. after mixing of the measurement signals) can be introduced as control signals 23 into the control input of the first stimulation unit 11 with a time delay and linear and/or nonlinear calculation steps. The calculation mode is hereby selected so that the pathological neuronal activity is counteracted and the tactile first stimuli 21, vibratory first stimuli 2 land/or thermal first stimuli 21 likewise disappear with a reducing pathological neuronal activity or are at least significantly reduced in their strength.

Figure 42A:
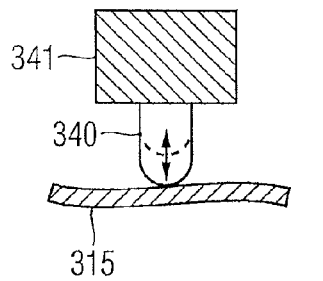
FIGS. 42A to 44C schematic illustrations of a stimulation element for the generation and application of specific tactile and/or vibratory stimuli.
Figure 42B:
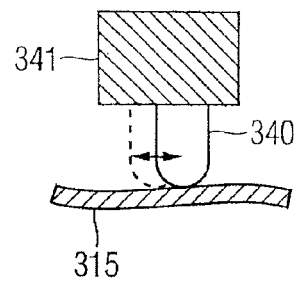
Figure 42C:
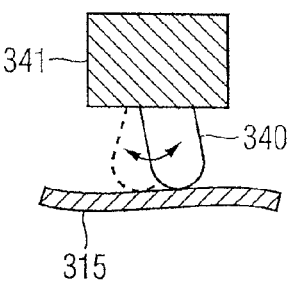

FIGS. 42A to 42C schematically show different possibilities for realizing a stimulation element for the generation of tactile and/or vibratory first stimuli 21 as are shown in the FIGS. 34A to 35. For example, the stimulation element can be designed as a rod 340 (or any other body) one end of which stimulates the skin 315 of the patient. The stimulation element 340 is driven by an electro-mechanic transformer 341 (or actor or actuator), which converts electrical energy into a movement of the stimulation element 340. For example, equal current motors, voice coils, piezo-electric transducers, or transformers built up of electro-active polymers (EAP) which change their shape on the application of an electric current are suitable as electro-mechanical transformers 341.

The electro-mechanic transformers 341 can be designed so that the stimulation element 340 is deflected perpendicular to the skin surface (cf. FIG. 42A) or parallel thereto (cf. FIG. 42B). The movement of the stimulation element 340 can, however, also take place on arbitrary different paths. A pendulum-shaped deflection of the stimulation element 340 is illustrated as an example of this in FIG. 42C.

Figure 43A:
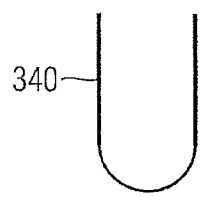
Figure 43B:
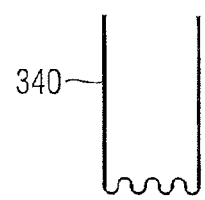

The end of the stimulation element 340 which comes into contact with the skin surface and which finally generates the stimuli can, for example, substantially have the shape of a half sphere (cf. FIG. 43A) or a pimple-like surface (cf. FIG. 43B) or any different suitable form.

Figure 44A:
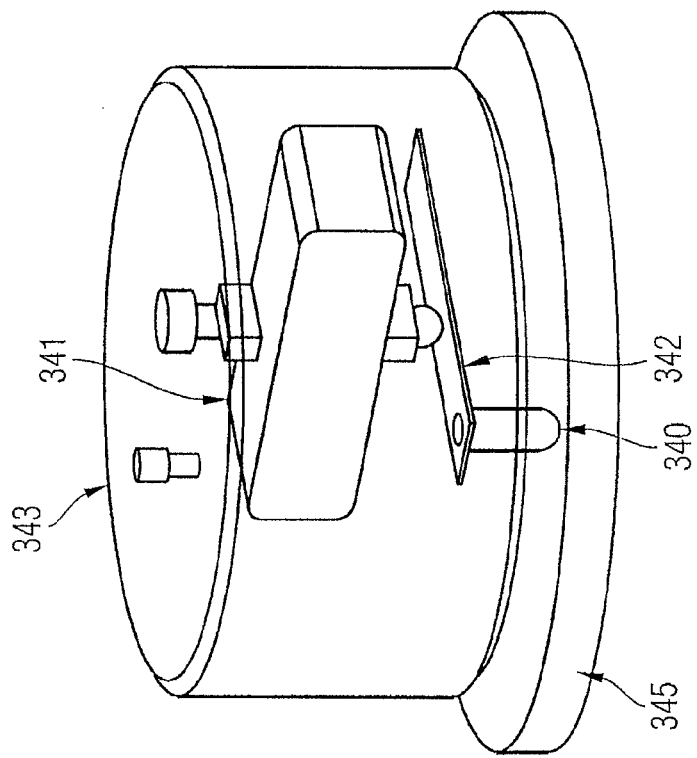
Figure 44C:
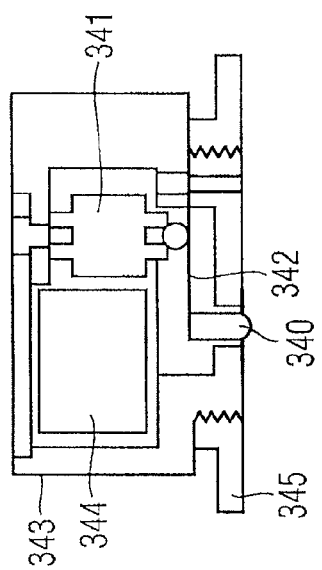
Figure 44B:
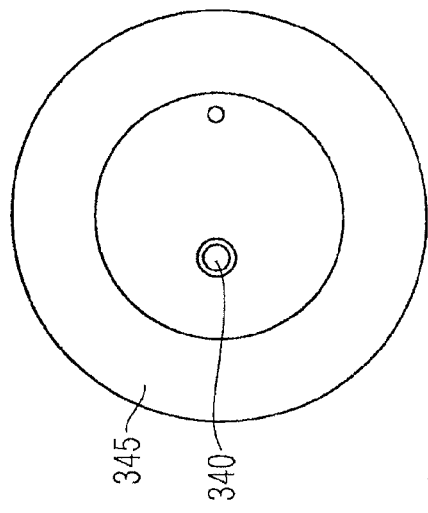

An embodiment of a stimulation element for the application of tactile and/or vibratory first stimuli 21 is shown in FIGS. 44A to 44C, in a phantom view (cf. FIG. 44A), a view from below (cf. FIG. 44B) and in cross-section (cf. FIG. 44C). The present stimulation element includes a piezo-actuator 341 as an electro-mechanic transformer. Since the deflection of the piezo-actuator 341 is not sufficient for the envisaged task a mechanism can be provided for the amplification of the deflection of the piezo-actuator 341. For example, a lever arm 342 is shown in this context which amplifies the movement of the piezo-actuator 341. The lever arm in the present example is a elongate flexible spring 342 which is attached at its one end at its housing 343 of the stimulation element and at its other end is attached at the stimulation element 340. The piezo-actuator 341 presses onto the upper side of the flexible spring 342 and the stimulation element 340 attached at the underside of the flexible spring 342 follows the deflection of the piezo-actuator 341 with an amplitude amplified due to the geometric arrangement and applies the vibration stimuli and/or touch stimuli at the skin of the patient. The underside of the stimulation element 340 which comes into contact with the skin can have different geometries and dimensions. For example, the stimulation element 340 can be flat, round or of unequal shape at its underside.

Moreover, a space 344 for electronics and connection connectors can be provided in the housing 343 of the stimulation element which housing houses the piezo-actuator 341 and the amplification mechanism. Moreover, a displacement ring 345 is attached at the underside of the housing 343 which is connected to the housing 343 via a threaded connection and enables a setting of the height about which the stimulation element 340 projects from the underside of the stimulation unit in its rest position. The stimulation element sits with its underside on the skin of the patient during the operation and is, for example, attached at the body of the patient with a suitable sleeve. In addition to the sleeve or as an alternative to the sleeve the stimulation element could also be attached with a one-sided or double-sided medical adhesive tape at the skin of the patient. The housing 343 protects the patient from possible dangers such as e.g. electrical voltage.

Figure 45A:
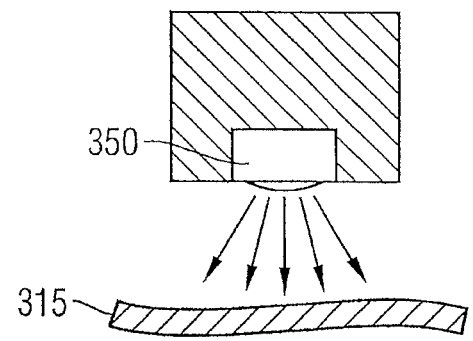
FIGS. 45A to 46C schematic illustrations of a stimulation element for the generation and application of specific thermal stimuli.
Figure 45B:
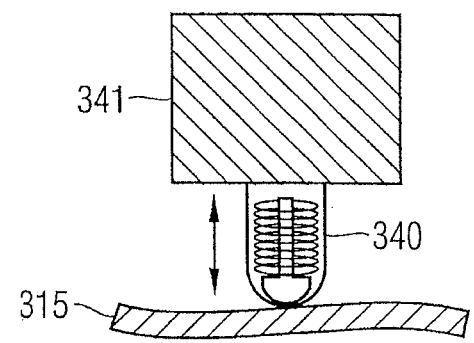
Figure 45C:
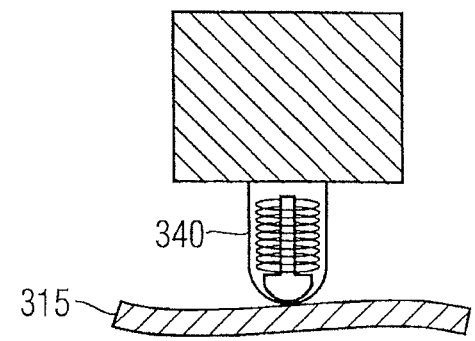

FIGS. 45A to 45C schematically show differently designed stimulation elements for the generation of thermal first stimuli 21 likewise are illustrated in FIGS. 36A to 36C. The stimulation unit illustrated in FIG. 45A works contact-less and brings about a heating of the skin through the light of an infrared LED 350.

Stimulation elements which apply thermal stimuli through contact of the skin surface are shown in FIGS. 45B and 45C. The stimulation element shown in FIG. 45B having an electro-mechanic transformer 341 and a rod-like stimulation elements 340 substantially includes the same components like the stimulation element of FIG. 42A. The stimulation element of FIG. 45B additionally includes a heating and/or cooling element (e.g. in the form of a heating coil) which heats or cools the stimulation elements. The thermal first stimuli 21 are generated through the movement of the stimulation element 341 in which the stimulation element 341 is repeatedly brought into contact with the skin 315 and is removed again. The temperature of the stimulation element 340 can be constant during the overall stimulation.

Alternatively, the heatable and/or coolable stimulation element 341 can be in contact with the skin 315 of the patient during the overall stimulation period in time as shown in FIG. 45C. The thermal stimuli are in this case generated through a timely variation of the temperature of the stimulation element 340. An electro-mechanic transformer is not necessarily required for this embodiment.

Figure 46A:
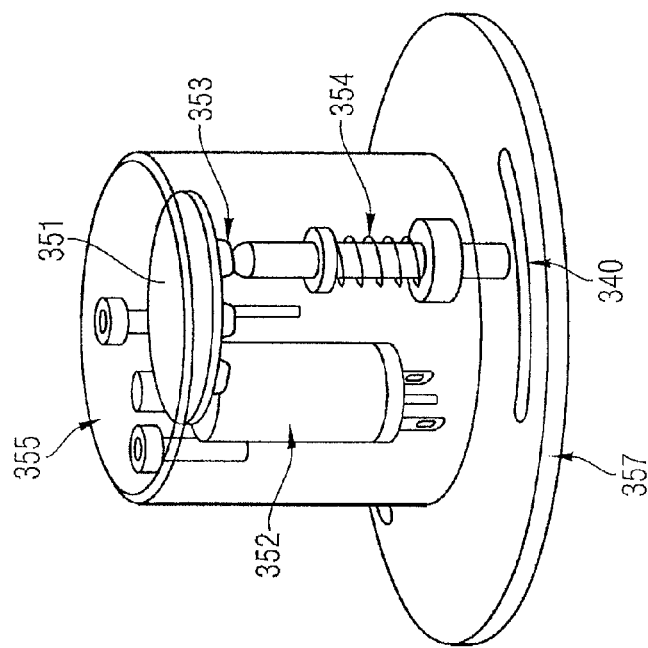
Figure 46C:
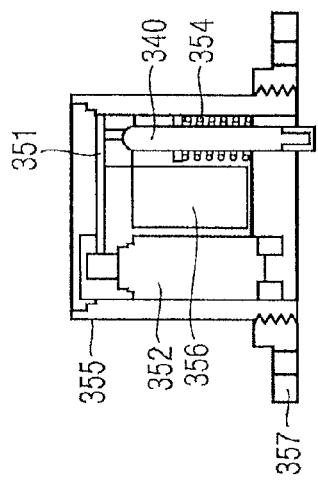
Figure 46B:
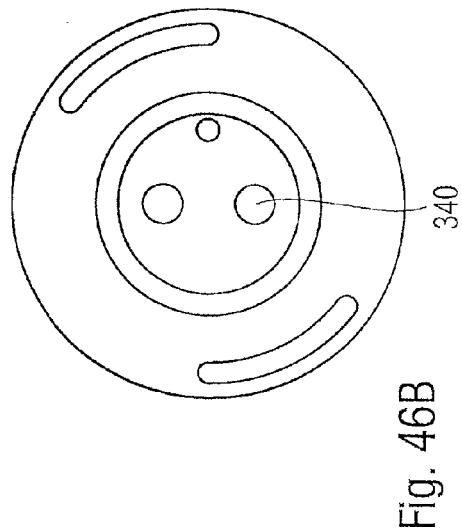

A design of a stimulation element for the application of thermal first stimuli 21 is shown in FIGS. 46A to 46C, in a phantom view (cf. FIG. 46A), a view from below (cf. FIG. 46B) and in cross-section (cf. FIG. 46C). The stimulation element includes a rod-shaped stimulation element 340 whose lower end is heatable and/or coolable. The stimulation element 340 is driven by a cam disc 341 at its upper end. An equal current motor 342 sets the cam disk 341 into rotation during the stimulation. The stimulation element 341 is deflected towards the bottom through the cams 353 attached at the underside of the cam disk 351. A retention spring 354 ensures that the stimulation element 340 subsequently returns again into its starting position. Through this mechanism the rotational movement of the cam disk 351 is transformed into a linear movement of the stimulation element 340. As described above, the stimulation element 340 can either come into contact with the skin of the patient for a certain time or, however, the stimulation element 340 is brought into contact with the skin and is removed again cyclically through a rotation of the cam disk 351.

The components of the stimulation element can be installed in a housing 355. A space 356 for electronics and connection connectors can be provided in the housing 355. Moreover, a displacement ring 357 can be attached at the underside of the housing 355 which is connected to the housing 355 via a threaded connection and enables a setting of the height at which the stimulation element 340 projects from the underside of the stimulation element in its rest position (the stimulation element 340 can also completely lie above the underside of the displacement ring due to the displacement ring in its rest position). The stimulation element sits with its underside at the skin of the patient during the operation and is, for example, attached with a suitable sleeve at the body of the patient. In addition to the sleeve, or as an alternative to the sleeve, the stimulation element could also be attached at the skin of the patient with a one-sided or double-sided medical adhesive tape. The housing 355 protects the patient of possible dangers, such as e.g. electrical voltage.

Figure 47:
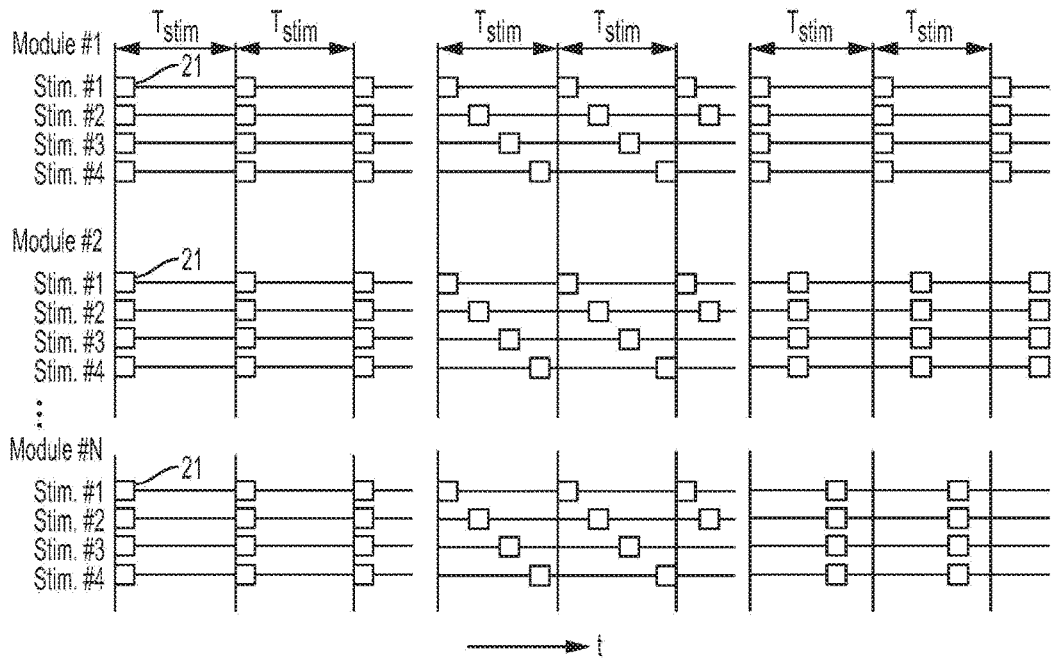
FIGS. 47 and 48 schematic illustrations of specific tactile, vibratory and/or thermal stimulation methods.

The stimulation elements described in this application can be individually attached at the patient or a plurality thereof can also be integrated into a module. A module can, for example, comprise a sleeve having a plurality of stimulation elements attached therein. The sleeve can then be attached at an arm or T a leg of the patient. FIG. 47 shows how stimulation methods can be carried out with a total of N modules which each include e.g. four stimulation elements. During the stimulation method illustrated on the very left of FIG. 47 all stimulation elements apply a tactile, vibratory or thermal first stimulus 21 at the start of a stimulation period $T_{stim}$. For the stimulation method shown in the middle of FIG. 47 the first stimuli 21 of the four different stimulation elements of a module are respectively displaced with regard to one another by $T_{stim}/4$. In this case precisely one stimulation element of each module applies a first stimulus 21 in each section of time of the length $T_{stim}/r$. For the stimulation method shown on the very right in FIG. 47 the four stimulation elements of a module simultaneously generate their first stimuli 21, however, the first stimuli 21 of different modules are displaced with regard to one another.

Arbitrary pauses can also be maintained during the stimulation for all the stimulation methods shown in FIG. 47. Typically, the stimulation pauses have the length of one or more stimulation periods $T_{stim}$. This is shown by way of example in FIG. 48. For the stimulation method illustrated there a stimulation is carried out during two stimulation periods $T_{stim}$ following one another, thereafter a stimulation pause is maintained during a stimulation period $T_{stim}$. This pattern repeats itself periodically.

Figure 48:
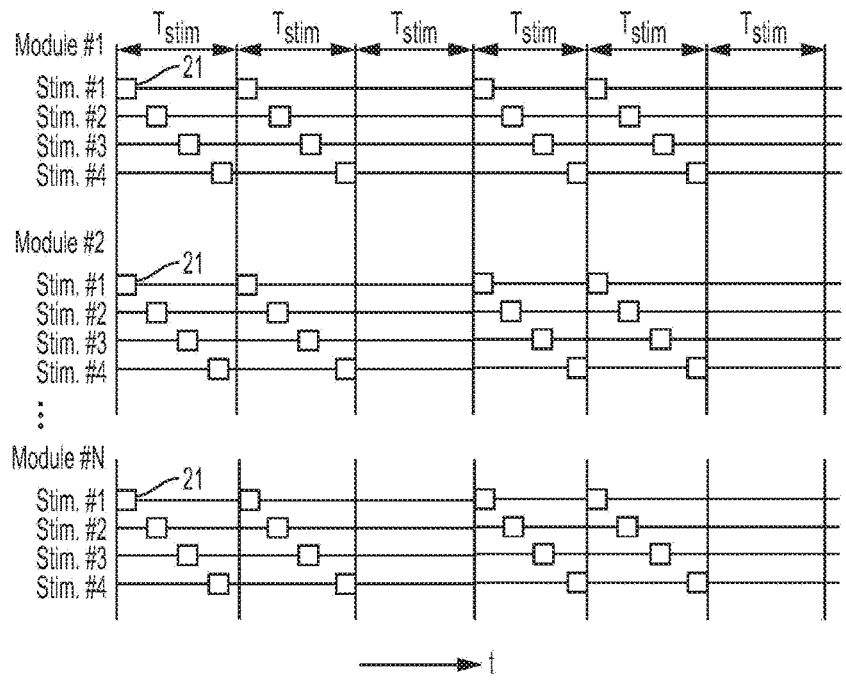

Furthermore, a randomization of the sequence in which the individual stimulation units generate the first stimuli 21 can be added to the stimulation methods shown in FIGS. 47 and 48, in which, amongst other things, the following randomizations are plausible.

1. Randomization of the stimuli sequences for each stimulation period $T_{stim}$ coherently over all modules, this means that a sequence is determined at the start of the stimulation period $T_{stim}$ in which the stimulation elements generate the first stimuli 21 (e.g. the sequence Stim. #4, Stim. #2, Stim. #3, Stim. #1) and this sequence is true for all modules.

2. Randomization of the stimuli sequences for a block of stimulation periods $T_{stim}$ following one after the other coherently over all modules, this means that a sequence is determined at the start of a block of stimulation periods $T_{stim}$ (and/or after a stimulation pause) following one another shown in FIG. 48, in which the stimulation elements generate the first stimuli 21 (e.g. the sequence Stim. #4, Stim. #2, Stim. #3, Stim. #1) and the sequence is true for all modules of the stimulation block up until the next pause.

3. Randomization of the stimuli sequences is not coherent over all modules, but is only coherently varied over the sub-group of all modules, this means that only for a certain module (e.g. the module #2) is a randomization in accordance with the aforementioned item 1. or item 2. carried out, the remaining modules behave as shown in FIG. 47.

4. Randomization of the stimuli sequences is not coherent over all modules but coherently varied over more than one sub-group of all modules, this means that a randomization is carried out for only two or more modules (e.g. the modules #2 and #4) in accordance with the aforementioned items 1. or 2., the remaining modules behave as shown in FIG. 47.

5. Randomization of the stimuli sequences is uncorrelated between different modules, this means that a sequence determined for each module independent of the other modules in which the stimulation element generate the first stimuli 21 over each stimulation period $T_{stim}$ or for each block of stimulation periods $T_{stim}$ following one another between two pauses.

Figure 49:
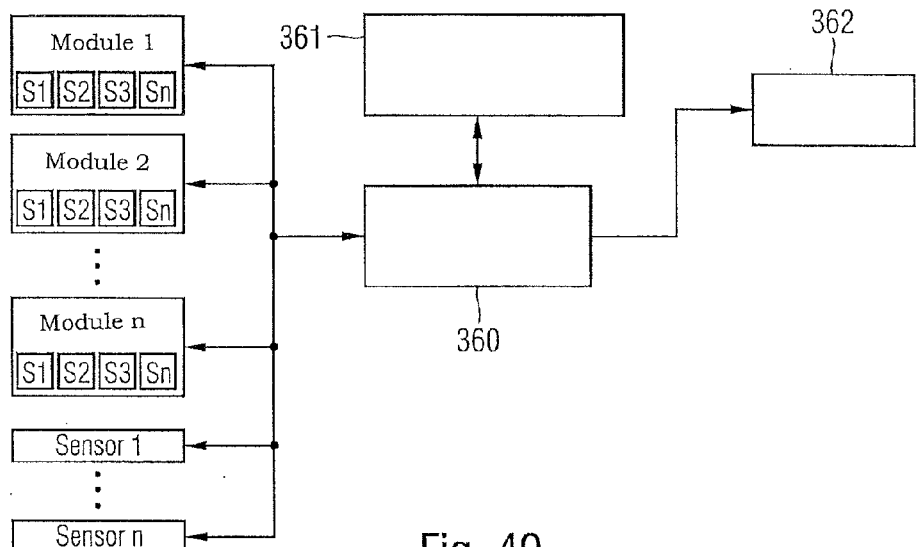
FIGS. 49 to 50C schematic illustrations of a stimulation unit for the generation and application of specific tactile, vibratory and/or thermal stimuli in accordance with a further embodiment.

The block circuit diagram of an apparatus for the generation of tactile, vibratory and/or thermo first stimuli 21 is schematically illustrated in FIG. 49. The apparatus includes n modules each with n stimulation elements as well as n sensors. The modules and sensors are in contact with a connection module 360 via connection lines or via radio communication (e.g. a WPAN (Wireless Personal Area Network)) which in turn can be connected to a computer 361, e.g. a laptop, and external apparatuses 362. Not all modules and sensors must necessarily be simultaneously used, depending on the type of stimulation also only a partial amount thereof can be used. The modules and/or sensors can be supplied with current through batteries or storage batteries so that they are independent of a central current supply. The user, for example a doctor, can select a stimulation method by means of a suitable software stored on the computer 361 and can set the parameters of this stimulation method.

Figures 50A, 50B:
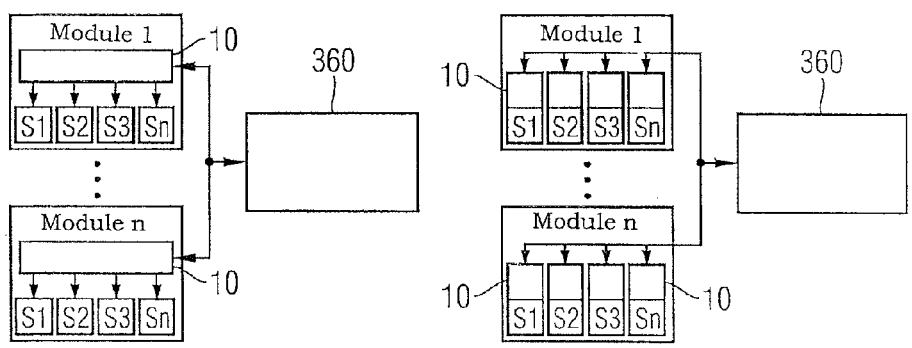
Figure 50C:
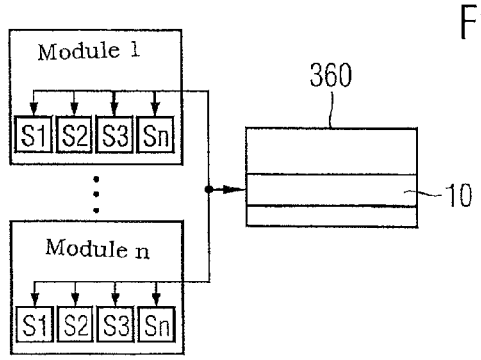

The control of the stimulation units integrated in the module can be effected via the computer 361. A control unit 10 (cf. FIG. 50A) can be integrated into each module as an alternative which is responsible for the control of the stimulation element of the respective module. This enables a substantially independent operation of the module. Moreover, an own control unit 10 can be provided for each stimulation element (cf. FIG. 50B). This enables the largest versatility on operation of the stimulation elements, however, the weight and the dimensions of the modules are increased thereby. As a further alternative, the control unit 10 can be placed centrally into the connection module 360 (cf. FIG. 50C). The low weight and size of the module as well as a cost-effective manufacture are advantages thereof. However, the modules cannot be operated independent of the connection module 360 in this embodiment.

FIG. 51 schematically shows an apparatus 5100 which has a first stimulation unit with stimulation elements 311 to 314 for the application of specific tactile, vibratory and/or thermal first stimuli 21, as e.g. described above, and has a second stimulation unit 12 for the application of the second, non-specific stimuli. The patient carries the stimulation elements 311 to 314 in the region of the concerned body part, e.g. for internal organs at the associated "Head zone". In the present embodiment the stimulation elements 311 to 314 are attached at the arm of a patient. The apparatus 5100 has the conditioning clock shown in FIGS. 4A and 4B as a second stimulation unit 12. The second non-specific stimuli can alternatively also be generated by means of a second stimulation unit 12 of different design.

The invention claimed is:

1. An apparatus comprising:
a first non-invasive stimulation unit configured to generate first stimuli during first periods of time, which, on administration to a patient, suppress a pathologically synchronous activity of neurons in at least one of the brain and the spinal cord of the patient;
a second non-invasive stimulation unit configured to generate at least one of optical, acoustic, tactile, vibratory, and thermal second stimuli during second periods of time;
a measurement unit configured to record measurement signals that reproduce the pathologically synchronous activity of the neurons; and
a control unit configured to:
control the first and second stimulation units to generate the first and second stimuli selectively in a first and a second mode of operation with the second mode of operation being subsequent to the first mode of operation,
control the first and second stimulation units such that at least 60% of the second periods of time of the second stimuli overlap in time with the first periods of time of the first stimuli in the first mode of operation, and such that at least 60% of the second periods of time of the second stimuli do not overlap with the first periods of time of the first stimuli in the second mode of operation,
increase a number of the first stimuli, during the second mode of operation, that overlap the generation of the second stimuli if the measurement signals exceed a predetermined first threshold value,
change from the second mode of operation to the first mode of operation if the measurement signals exceed a predetermined second threshold value being greater than the predetermined first threshold value.

2. The apparatus in accordance with claim 1, wherein the first stimuli are at least one of optical, acoustic, tactile, vibratory, and thermal stimuli.

3. The apparatus in accordance with claim 1, wherein at least 80% of the second periods of time of the second stimuli overlap with the first periods of time of the first stimuli in the first mode of operation, and at least 80% of the second periods of time of the second stimuli do not overlap with the first periods of time of the first stimuli in the second mode of operation.

4. The apparatus in accordance with claim 1, wherein the second stimuli are intentionally perceptible by the patient.

5. The apparatus in accordance with claim 1, wherein the first stimulation unit comprises at least one of transmission eyeglasses, eyeglasses having a plurality of light sources, a sound generator, a direct current motor, an oscillator coil, a piezoelectric transducer, an electroactive polymer, a heating element, a cooling element, and an infrared light source.

6. The apparatus in accordance with claim 1, wherein the first stimulation unit is further configured to one of convert the measurement signals into the first stimuli and convert the measurement signals into the first stimuli following a further processing thereof.

7. The apparatus in accordance with claim 1, wherein the overlap in time of one of the first periods of time with one of the second periods of time amounts to at least 10% of the duration in time of the second period of time.

8. The apparatus in accordance with claim 1, wherein the first stimulation unit comprises a plurality of stimulation elements configured to administer the first stimuli to the patient and the first stimuli are adapted such that they reset the phase of oscillating activity of a neuron population on stimulation of a neuron population which has a pathologically synchronous and oscillating activity.

9. The apparatus in accordance with claim 1, wherein the apparatus comprises a programming device by means of which the patient can bring about a change from the second mode of operation into the first mode of operation.

10. An apparatus comprising:
a non-invasive first stimulation unit configured to generate at least one of optical, acoustic, tactile, vibratory, and thermal first stimuli during first periods of time, which, when administered to a patient, suppress a pathologically synchronous activity of neurons in at least one of the brain and the spinal cord of the patient;
a non-invasive second stimulation unit configured to generate at least one of optical, acoustic, tactile, vibratory, and thermal second stimuli during second periods of time, the second stimuli being intentionally perceptible by the patient; and
a measurement unit configured to record measurement signals that reproduce the pathologically synchronous activity of the neurons,
wherein:
the non-invasive first and second stimulation units are configured to operate in a learning phase such that the first and second stimuli are administered to the patient with at least 60% of the second periods of time of the second stimuli overlapping in time with the first periods of time of the first stimuli to condition the nervous system of the patient such that, on an administration of the second stimuli without the first stimuli, the nervous system reacts as on an administration of the first stimuli, the non-invasive first and second stimulation units are configured to operate in a stimulation phase, subsequent to the learning phase, such that the second stimuli are administered to the patient with at least 60% of the second periods of time of the second stimuli not overlapping in time with the first periods of time of the first stimuli at least partly without the first stimuli, a number of the first stimuli during the stimulation phase that overlaps the generation of the second stimuli is increased if the measurement signals exceed a predetermined first threshold value, and the non-invasive first and second stimulation units switch from operating in the stimulation phase to the learning phase if the measurement signals exceed a predetermined second threshold value being greater than the predetermined first threshold value.

11. An apparatus comprising:

a non-invasive first stimulation unit configured to generate at least one of optical, acoustic, tactile, vibratory, and thermal first stimuli which, when administered to a patient, suppress a pathologically synchronous activity of neurons in at least one of the brain and the spinal cord of the patient;

a non-invasive second stimulation unit configured to generate at least one of optical, acoustic, tactile, vibratory, and thermal second stimuli; and a measurement unit configured to record measurement signals that reproduce the pathologically synchronous activity of the neurons, wherein:
the generation of the first stimuli takes place in first periods of time, and generation of the second stimuli takes place in second periods of time, the non-invasive first and second stimulation units generate the first and second stimuli selectively in first and second modes of operation with the second mode of operation being subsequent to the first mode of operation, at least 60% of the second periods of time respectively at least overlap in time with one of the first periods of time in the first mode of operation and at least 60% of the second periods of time have no overlap with the first period of time in the second mode of operation, a number of the first stimuli, during the second mode of operation, that overlap the generation of the second stimuli is increased if the measurement signals exceed a predetermined first threshold value, and the non-invasive first and second stimulation units switch from the second mode of operation to the first mode of operation if the measurement signals exceed a predetermined second threshold value being greater than the predetermined first threshold value.

12. A method comprising:

administering first stimuli in first periods of time to a patient in a non-invasive manner, wherein the first stimuli suppress a pathologically synchronous activity of neurons in at least one of the brain and the spinal cord of the patient;

administering at least one of optical, acoustic, tactile, vibratory, and thermal second stimuli in second periods of time to the patient in a non-invasive manner;

administering the first and second stimuli selectively in a first and a second mode of operation with the second mode of operation being administered subsequent to the first mode of operation, and wherein the first and second stimuli are administered such that at least 60% of the second periods of time of the second stimuli overlap in time with the first periods of time of the first stimuli in the first mode of operation, and at least 60% of the second periods of time of the second stimuli do not overlap with the first periods of time of the first stimuli in the second mode of operation.

13. The method in accordance with claim 12, wherein the first stimuli are at least one of optical, acoustic, tactile, vibratory, and thermal stimuli.

14. The method in accordance with claim 12, wherein at least 80% of the second periods of time of the second stimuli overlap with the first periods of time of the first stimuli in the first mode of operation, and at least 80% of the second periods of time of the second stimuli do not overlap with the first periods of time of the first stimuli in the second mode of operation.

15. The method in accordance with claim 12, further comprising recording measurement signals that reproduce the pathologically synchronous activity of the neurons.

16. The method in accordance with claim 15, further comprising increasing a number of first stimuli whose administration overlaps with the administration of the second stimuli if the measurement signals exceed a predetermined first threshold value in the second mode of operation.

17. The method in accordance with claim 16, further comprising changing from the second mode of operation into the first mode of operation if the measurement signals exceed a predetermined second threshold value.

* * * * *